US010829549B2

(12) United States Patent
Boakye et al.

(10) Patent No.: US 10,829,549 B2
(45) Date of Patent: Nov. 10, 2020

(54) ANTI-CCL17 ANTIBODIES

(71) Applicant: Jannsen Biotech, Inc., Horsham, PA (US)

(72) Inventors: Ken Boakye, Spring House, PA (US); Alfred Del Vecchio, Spring House, PA (US); John Kehoe, Spring House, PA (US); Eilyn Lacy, Spring House, PA (US); Lynne Murray, Melbourn (GB); Mary Ryan, Spring House, PA (US); Sandra Santulli-Marotto, Spring House, PA (US); John Wheeler, Spring House, PA (US); Brian Whitaker, Spring House, PA (US); Alexey Teplyakov, Spring House, PA (US)

(73) Assignee: Jannsen Biotech, Inc., Horsham, PA (US)

( * ) Notice: Subject to any disclaimer, the term of this patent is extended or adjusted under 35 U.S.C. 154(b) by 0 days.

(21) Appl. No.: 15/835,529

(22) Filed: Dec. 8, 2017

(65) Prior Publication Data
US 2018/0171007 A1 Jun. 21, 2018

Related U.S. Application Data

(62) Division of application No. 14/534,525, filed on Nov. 6, 2014, now Pat. No. 9,944,697.

(60) Provisional application No. 61/900,596, filed on Nov. 6, 2013.

(51) Int. Cl.
A61K 39/00 (2006.01)
C07K 16/24 (2006.01)

(52) U.S. Cl.
CPC .............. C07K 16/24 (2013.01); A61K 39/00 (2013.01); A61K 2039/55522 (2013.01); C07K 2317/56 (2013.01); C07K 2317/565 (2013.01); C07K 2317/76 (2013.01); C07K 2317/92 (2013.01)

(58) Field of Classification Search
None
See application file for complete search history.

(56) References Cited

U.S. PATENT DOCUMENTS

| 4,683,985 | A  | 7/1987  | Mullis et al. |
|-----------|----|---------|-----------------|
| 5,223,409 | A  | 6/1993  | Ladner et al. |
| 5,225,539 | A  | 7/1993  | Winter |
| 5,403,484 | A  | 4/1995  | Ladner et al. |
| 5,427,908 | A  | 6/1995  | Dower et al. |
| 5,565,332 | A  | 10/1996 | Hoogenboom et al. |
| 5,571,698 | A  | 11/1996 | Ladner et al. |
| 5,580,717 | A  | 12/1996 | Dower et al. |
| 5,869,620 | A  | 2/1999  | Whitlow et al. |
| 5,885,793 | A  | 3/1999  | Griffiths et al. |
| 5,932,448 | A  | 8/1999  | Tso et al. |
| 5,969,108 | A  | 10/1999 | McCafferty et al. |
| 6,150,584 | A  | 11/2000 | Kucherlapati et al. |
| 6,172,197 | B1 | 1/2001  | McCafferty et al. |
| 6,521,404 | B1 | 2/2003  | Griffiths et al. |
| 6,544,731 | B1 | 4/2003  | Griffiths et al. |
| 6,555,313 | B1 | 4/2003  | Griffiths et al. |
| 6,593,081 | B1 | 7/2003  | Griffiths et al. |
| 6,737,056 | B1 | 5/2004  | Presta |
| 6,818,749 | B1 | 11/2004 | Kashmiri et al. |
| 6,833,441 | B2 | 12/2004 | Wang et al. |
| 7,695,936 | B2 | 4/2010  | Carter et al. |
| 7,709,226 | B2 | 5/2010  | Foote |
| 2007/0287170 | A1 | 12/2007 | Davis et al. |
| 2009/0118127 | A1 | 5/2009  | Raghunathan |
| 2010/0015133 | A1 | 1/2010  | Igawa et al. |
| 2010/0021477 | A1 | 1/2010  | Tsui et al. |
| 2010/0261620 | A1 | 10/2010 | Almagro et al. |
| 2010/0278844 | A1 | 11/2010 | Balkwill et al. |
| 2010/0286374 | A1 | 11/2010 | Kannan et al. |
| 2011/0123532 | A1 | 5/2011  | Gurney et al. |
| 2011/0206672 | A1 | 8/2011  | Little et al. |
| 2012/0082622 | A1 | 4/2012  | Naso et al. |
| 2012/0108795 | A1 | 5/2012  | Kehoe et al. |
| 2012/0149876 | A1 | 6/2012  | Von Kreudenstein et al. |
| 2012/0156198 | A1 | 6/2012  | Brandt et al. |
| 2013/0171659 | A1 | 7/2013  | Morota et al. |

FOREIGN PATENT DOCUMENTS

| WO | WO 88/01649 A1 | 3/1988 |
|----|----------------|--------|
| WO | WO 90/04036 A1 | 4/1990 |
| WO | WO 90/07861 A1 | 7/1990 |
| WO | WO 92/01047 A1 | 1/1992 |
| WO | WO 92/22653 A1 | 1/1992 |
| WO | WO 94/13804 A1 | 6/1994 |
| WO | WO 95/15388 A1 | 6/1995 |
| WO | WO 97/14719 A1 | 4/1997 |

(Continued)

OTHER PUBLICATIONS

Holm et al. Pharmacological evaluation of the SCID T cell transfer model of colitis. Journal of Crohn's and Colitis, vol. 6, Supp. SUPPL. 1, pp. S16. Abstract No. P014 (Feb. 2012). (Year: 2012).*
Wauwe J V. Interleukin-5 as a potential target for asthma treatment. Drug News & Perspectives. ABSTRACT vol. 13, No. 4, pp. 197-205 (May 2000). (Year: 2000).*
Kasaian et al. The efficacy of IL-13 neutralization in a sheep model of experimental asthma. Am J Respir Cell Mol Biol vol. 36. pp. 368-376 (2007) (Year: 2007).*
Ismailoglu et al. The effects of targeting CCL17 and CCL22 in bleomycin induced murine fibrosis model. American Journal of Respiratory and Critical Care Medicine, vol. 183, No. 1, Supp. Abstract No. A4286; (May 2011). (Year: 2011).*

(Continued)

Primary Examiner — Elizabeth C. Kemmerer
Assistant Examiner — Regina M DeBerry
(74) Attorney, Agent, or Firm — Finnegan, Henderson, Farabow, Garrett & Dunner, LLP

(57) ABSTRACT

The present invention relates to antibodies specifically binding CCL17, polynucleotides encoding the antibodies or fragments, and methods of making and using the foregoing.

7 Claims, 16 Drawing Sheets

Specification includes a Sequence Listing.

(56) References Cited

FOREIGN PATENT DOCUMENTS

| WO | WO 1997/29192 A1 | 8/1997 |
|---|---|---|
| WO | WO 98/44001 A1 | 10/1998 |
| WO | WO 99/45962 A1 | 9/1999 |
| WO | WO 99/57150 A2 | 11/1999 |
| WO | WO 02/43478 A2 | 6/2002 |
| WO | WO 02/06630 A1 | 8/2002 |
| WO | WO 2004/111233 A1 | 12/2004 |
| WO | WO 2008/119353 A1 | 10/2008 |
| WO | WO2009/037454 A2 | 3/2009 |
| WO | WO 2009/085462 A1 | 7/2009 |
| WO | WO 2009/120922 A2 | 10/2009 |
| WO | WO 2009/134776 A2 | 11/2009 |
| WO | WO 2011/036460 A1 | 3/2011 |
| WO | WO 2011/056997 A1 | 5/2011 |
| WO | WO 2011/066501 A1 | 6/2011 |
| WO | WO 2011/131746 A2 | 10/2011 |
| WO | WO 2011/143545 A1 | 11/2011 |
| WO | WO 2012/022811 A1 | 2/2012 |
| WO | WO 2012/047584 A2 | 4/2012 |

OTHER PUBLICATIONS

Saldanha, J. "Molecular Engineering I: Humanization," Handbook of Therapeutic Antibodies 119-121 (2007).

Alferink, et al., "Compartmentalized Production of CCL 17 In Vivo: Strong Inducibility in Peripheral Dendritic Dells Contrasts Selective Absence from the Spleen," The Journal of Experimental Medicine, 197(5): 585-599 (2003).

Algerian Patent Application No. 160267, by Janssen Biotech, Inc.: Office Action dated Jun. 15, 2017 (1 page).

Al-Lazikani, et al., "Standard Conformations for the Canonical Structures of Immunoglobulins," Journal of Molecular Biology, 273: 927-948 (1997).

Allen, et al., "Chemokine: Receptor Structure, Interactions, and Antagonism," Annual Review of Immunology, 25: 787-820 (2007).

Angal et al. A single amino acid substitution abolishes the heterogeneity of chimeric mouse/human (IgG4) antibody. Molecular Immunology, vol. 30/1:105-108 (Jan. 1993).

Baatar, et al., "CCR4-Expressing T Cell Tumors Can Be Specifically Controlled via Delivery of toxins to Chemokine Receptors," The Journal of Immunology, 179: 1996-2004 (2007).

Bedu-Addo, "Use of Biophysical Characterization in Preformulation Development of a Heavy-Chain Fragment of Botulinum Serotype B: Evaluation of Suitable Purification Process Conditions," Pharmaceutical Research, 21(8): 1353-1361 (2004).

Belperio, et al., "The Role of the Th2 CC Chemokine Ligand CCL17 in Pulmonary Fibrosis," The Journal of Immunology, 173: 4692-4698 (2004).

Berin, et al., "Regulated Production of the T Helper 2-Type T-Cell Chemoattractant TARC by Human Bronchial Epithelial Cells In Vitro and in Human Lung Xenografts," American Journal of Respiratory and Cellular and Molecular Biology, 24: 382-389 (2000).

Brüggemann, et al., "Human antibody production in transgenic mice: expression from 100kb of the human IgH locus," European Journal of Immunology, 21: 1323-1326 (1991).

Brüggemann, et al., "Production of human antibody repertoires in transgenic mice," Current Opinion in Biotechnology, 8: 455-458 (1997).

Carpenter, et al., "Immunosuppressive Effects of CCL17 on Pulmonary Antifungal Responses during Pulmonary Invasive Aspergillosis," Infection and Immunity, 73(11): 7198-7207 (2005).

Casset et al. A peptide mimetic of an anti-CD4 monoclonal antibody by rational design. Biochem Biophys Res Comm. vol. 307:198-205 (2003).

Chothia, et al., "Canonical Structures of the Hypervariable Regions of Immunoglobulins," Journal of Molecular Biology, 196: 901-917 (1987).

Christophi, et al., "Immune Markers and Differential Signaling Networks in Ulcerative colitis and Crohn's Disease," Inflammatory Bowel Disease, 18: 2342-2356 (2012).

PCT International Search Report dated Feb. 26, 2016.

Dall' Acqua, et al., "Properties of Human IgG 1s Engineered for Enhanced Binding to the Neonatal Fe Receptor (FeRN)," The Journal of Biological Chemistry, 281(33): 23514-23524 (2006).

D'ambrosio, et al., "Quantitative Differences in Chemokine Receptor Engagement Generate Diversity in Integrin-Dependent Lymphocyte Adhesion," The Journal of Immunology, 169: 2303-2312 (2002).

Eduardo A. Padlan, A Possible Procedure for Reducing the Immunogenicity of Antibody Variable Domains While PreseiVing their Ligand-binding Properties, Molecular Immunology, 28(4/5): 489-499 (1991).

European Patent Application No. 14860331.9, by Janssen Biotech, Inc.: Supplementary European Search Report dated May 23, 2017 (11 pages).

Fahy, et al, "Reactive Airways Disease," American Journal of Respiratory and Critical Care Medicine, 163: 822-823 (2001).

Fishwild, et al., "High-avidity human IgGK monoclonal antibodies from a novel strain of minilocus transgenic mice," Nature Biotechnology, 14: 845-851 (1996).

Frans son, et al., "Human Framework Adaptation of a Mouse Anti-Human IL-13 Antibody," Journal of Molecular Biology, 398: 214-231 (2010).

Godiska, et al., "Human macrophage-derived Chemokine (MDC), a Novel Chemoattractant for Monocyte-derived Dendritic Cells, and Natural Killer Cells," Journal of Experimental Medicine, 185(9): 1595-1604 (1997).

Gooding, "Production of monoclonal Antibodies," Monoclonal Antibodies: Principles and Practice, Academic Press, 59-103 (1986).

Green, et al., "Antigen-specific human monoclonal antibodies from mice engineered with human Ig heavy and light chain YACs," Nature Genetics, 7: 13-21 (1994).

Green, et al., "Regulation ofB Cell Development by Variable Gene Complexity in Mice Reconstituted with Human Immunoglobulin Yeast Artificial Chromosomes," Journal of Experimental Medicine, 188(3): 483-495 (1998).

Gupta, et al., "Development of a Multidose Formulation for a Humanized Monoclonal Antibody using Experimental Design Techniques," AAPS Pharmaceutical Science, 5(2): 1-9 (2003).

Gustchina, et al, "Structural Basis of HIV-1 Neutralization by Affinity Matured Fabs Directed against the Internal Trimeric Coiled-Coil of gp41," PLOS Pathogens, 6(11): e1001182 (2010).

Haenel, et al., "Characterization of high-affinity antibodies by electrochemiluminescence-based equilibrium titration," Analytical Biochemistry, 339: 182-184 (2005).

Heiseke, et al., "CCL 17 Promotes Intestinal Inflammation in Mice and Counteracts Regulatory T Cell-Mediated protection From Colitis," Gastroenterology, 142: 335-345 (2012).

Hessel, et al., "Bronchoconstriction and airway hyperresponsiveness after ovalbumin inhalation in sensitized mice," European Journal of Pharmacology, 293: 401-412 (1995).

Hogaboam, et al., "*Aspergillus* and asthma—any link?" Medical Mycology Supplement, 43: 5197-5202 (2005).

Hoogenboom, et al., "By-passing Immunisation Human Antibodies from Synthetic Repertoires of Germline VH Gene Segments Rearranged in Vitro,"Journal of Molecular Biology, 227: 381-388 (1992).

Imai, et al., "Macrophage-derived chemokine Is a Functional Ligand for the CC Chemokine Receptor 4," The Journal of Biological Chemistry, 273: 3: 1764-1768 (1998).

Imai, et al., "Molecular cloning of a Novel T Cell-directed CC Chemokine Expressed in Thymus by Signal Sequence Trap Using Epstein-Barr Virus Vector," The Journal of Biological Chemistry, 271(35): 21514-21521 (1996).

Inoue et al., "CCL22 and CCL17 in rat radiation pneumonitis and in human idiopathic pulmonary fibrosis," European Respiratory Journal, 24: 49-56, 2004.

Ismailoglu et al., "Therapeutic targeting of CCL17 Via the Systemic Administration of a Monoclonal Antibody Ameliorates Experimental Fungal Asthma," American Journal of Respiratory and Critical Care Medicine, 183: A4504 (2011). Abstract only.

(56) References Cited

OTHER PUBLICATIONS

Jakubzick et al., "Role of CCR4 Ligands, CCL17 and CCL22, During Schistosoma mansoni Egg-Induced Pulmonary Granuloma Formation in Mice," American Journal of Pathology, 165(4):1211-122, 2004.
Juan C. Almagro, "Identification of differences in the specificity-determining residues of antibodies that recognize antigens of different size: implications for the rational design of antibody repertoires," Journal of Molecular Recognition, 17: 132-142=3 (2004).
Kakinuma et al., "Thymus and activation-regulated chemokine in atopic dermatitis: Serum thymus and activation-regulated chemokine level is closely related with disease activity," Journal of Allergy and Clinical Immunology, 107: 535-541,2001.
Kawasaki et al., "Intervention of thymus and Activation-Regulated Chemokine Attenuates the Development of Allergic Airway Inflammation and Hyperresponsiveness in Mice," Journal of Immunology, 166:2055-2062,2001.
Kehoe et al., "Isolation and optimization for affinity and biophysical characteristics of anti-CCL17 antibodies from the $V_H$ I-69 germline gene," *Protein Engineering, Design and Selection*, 27(6): 199-206 (2014).
Knappik et al., "Fully Synthetic Human Combinatorial Antibody Libraries (HuCAL) Based on Modular Consensus Frameworks and CDRs Randomized with Trinucleotides," Journal of Molecular Biology, 296:57-86, (2000).
Knight et al., Pharmacodynamic enhancements of the anti-platelet antibody Fab abciximab by site-specific pegylation, Platelets 15(7):409-418, (2004).
Kohler, et al., "Continuous cultures of fused cells secreting antibody of predefined specificity," Nature 256:495, (1975).
Krebs et al., "High-throughput generation and engineering of recombinant human antibodies," Journal of Immunological Methods, 254:67-84, (2001).
La Porte et al, "Generation of a high-fidelity antibody against nerve growth factor using library scanning mutagenesis and validation with structures of the initial and optimized Fab-antigen complexes," MAbs 6:1059-1068 (2014).
Larry L. Green, "Antibody engineering via genetic engineering of the mouse: XenoMouse strains are a vehicle for the facile generation of therapeutic human monoclonal antibodies," Journal of Immunological Methods, 231: 11-23 (1999).
Lefranc et al., "ImGT unique numbering for immunoglobulin and T cell receptor variable domains and Ig superfamily V-like domains," Developmental & Comparative Immunology, 27:55-77, (2003).
Leong et al., "Adapting Pharmacokinetic Properties of a Humanized Anti-Interleukin-8 Antibody for therapeutic Applications Using Site-Specific Pegylation," Cytokine 16(3): 106-119 (2001).
Linden et al., "Airway neutrophils and interleukin-17," European Respiratory Journal, 15:973-977 (2000).
Lonberg, et al., "Antigen-specific human antibodies from mice comprising four distinct genetic modification," Nature 368:856-859 (1994).
Lonberg, et al., "Human Antibodies from Transgenic Mice," International Review of Immunology, 13:65-93, 1995.
Maa, et al., "Aggregation of recombinant human growth hormone induced by phenolic compounds," International Journal of Pharmaceutics, 140: 15 5-168 ( 1996).
MacCallum et al. Antibody-antigen interactions: Contact analysis and binding site topography. J Mol Bioi. vol. 262:732-745 (1996).
Mariani et al., "Dominance of CCL22 over CCL 17 in induction of chemokine receptor CCR4 desensitization and internalization on human Th2 cells," European Journal of Immunology, 34:231-240 (2004).
Marks et al., "By-passing Immunization Human Antibodies from V-gene Libraries Displayed on Phage," Journal of molecular Biology, 222: 581-597 (1991).
Matsukawa et al., "Chemokines and Innate immunity," Review of Immunogenetics, 2: 339-358 (2000).
Matsukawa et al., Pivotal Role of the CC Chemokine, Macrophage-Derived chemokine, in the Innate Immune Response, The Journal of Immunology, 164: 5362-5368 (2000).
Mendez et al., "Functional transplant of megabase human immunoglobulin loci recapitulates human antibody response in mice," Nature Genetics, 15:146-156 (1997).
Montane et al., "Prevention of murine autoimmune diabetes by CCL22-mediated Treg recruitment to the pancreatic islets," Journal of Clinical Investigations, 121:3024-30 (2011).
Morris, Glenn E., "Epitope Mapping of Protein Antigens by Competition ELISA," *The Protein Protocols Handbook*, pp. 595-600 (1996).
Ngo et al. (Computational Complexity, Protein Structure Prediction and the Levinthal Paradox. The Protein Folding Problem and Tertiary Structure Prediction, pp. 433-440 and 492-495 (1994).
Osborn et al., From rodent reagents to human therapeutics using antibody guided selection, Methods 36:61-68 (2005).
Paul, W.E. Fundamental Immunology, Third Edition Textbook, "Fv Structure and Diversity in Three Dimensions" pp. 292-295; Raven Press, New York (1993).
Rahman et al., "IL-17R activation of human airway smooth muscle cells induces CXCL-8 production via a transcriptional-dependent mechanism," Clinical Immunology, 115:268-276 (2005).
Remmele et al., "Interleukin-1 Receptor (IL-1R) Liquid Formulation Development Using Differential Scanning Calorimetry," Pharmaceutical Research, 15:200-208 (1997).
Saeki, et al. "Thymus and activation regulated chemokine (TARC)/CCL 17 and skin diseases," Journal of Dermatological Science, 43: 75-84 (2006).
Santulli-Marotto et al., "Engagement of Two Distinct Binding Domains on CCL17 is Required for Signaling through CCR4 and Establishment of Localized Inflammatory Conditions in the Lung," *PLOS ONE*, 8(12): 1-13 (Dec. 2013).
Santulli-Marotto et al., "Surrogate Antibodies That Specifically Bind and Neutralize CCL17 But Not CCL22," *Monoclonal Antibodies in Immunodiagnosis and Immunotherapy*, 32(3): (2013).
Sheets et al., "Efficient construction of a large nonimmune phage antibody library: The production of high-affinity human single-chain antibodies to protein antigens," Proceedings of the National Academy of Science USA, 95:6157-6162 (1998).
Shi et al., "De Novo Selection of High-Affinity antibodies from synthetic Fab Libraries Displayed on Phage as piX Fusion Proteins," Journal of Molecular Biology, 397:385-396 (2010).
Singapore Patent Application No. 11201603231X, by Janssen Biotech, Inc.: Search Report dated May 5, 2017 (2 pages).
Singapore Patent Application No. 11201603231X, by Janssen Biotech, Inc.: Written Opinion dated May 5, 2017 (6 pages).
Tamaki et al., "Serum levels of CCL17 /TARC in various skin diseases," Journal of Dermatology, 33: 300-302 (2006).
Tokuriki et al., Stability effects of mutations and protein evolvability; Current Opinion in Structural Biology, 19:596-604 (2009).
Vafa et al., "An engineered Fc variant of an IgG eliminates all immune effector functions via structural perturbations," *Methods*, 65: 114-126 (2014).
Vaughan et al., "Human Antibodies with Sub-nanomolar Affinities Isolated from a Large Nonimmunized Phage Display Library," Nature Biotechnology 14:309-314 (1996).
Ward et al., "Binding activities of a repertoire of single immunoglobulin variable domains secreted from *Escherichia coli*," Nature 341:544-546 (1989).
Weber et al., "CCL17-expressing dendritic cells drive atherosclerosis by restraining regulatory T cell homeostasis in mice," Journal of Clinical Investigation, 121:2898-2910 (2011).
Wells, J.A., "Additivity of Mutational Effects in Proteins. Biochemistry," 29:8509-8517 (1990).
Worn, et al., "Stability Engineering of Antibody Single-chain Fv Fragments," Journal of Molecular Biology, 305:989-1010 (2001).
Wu, et al., "An Analysis of the Sequences of the Variable Regions of Bence Jones Proteins and Myeloma Light Chains and their Implications for Anti-Body Complementarity," Journal of Experimental Medicine, 132:211-250, 1970.

(56) References Cited

OTHER PUBLICATIONS

Yang et al., "Eradication of Established Tumors by a Fully Human monoclonal Antibody to the Epidermal Growth Factor Receptor without Concomitant Chemotherapy," Cancer Research, 59: 1236-1243 (1999).
Yang et al., "Tailoring structure-function and pharmacokinetic properties of single-chain Fv proteins by site-specific PEGylation," Protein Engineering, 16(10): 761-770 (2003).
Yasui et al., "Effects of substitutions of amino acids on the thermal stability of the Fv fragments of antibodies," FEBS Lett 353:143-146 (1994).
Yoneyama et al., "Pivotal Role of TARC, a CC Chemokine, in Bacteria-induced Fulminant Hepatic Failure in Mice," Journal of Clinical Investigation, 102:1933-1941 (1998).
Zhang et al., "Mechanism for Benzyl Alcohol-Induced Aggregation of Recombinant Human Interleukin-1 Receptor Antagonist in Aqueous Solution," Journal of Pharmaceutical Science, 93:3076-3089 (2004).
Sela-Culang et al., "The structural basis of antibody-antigen recognition," Frontiers in Immunology, vol. 4, Article 302, pp. 1-13, Oct. 2013.

\* cited by examiner

Figure 3.

```
              1                            30
C17B234_VH_45 EVQLVQSGAEVKKPGESLKISCKGSGYSFT
C17B235_VH_45 EVQLVQSGAEVKKPGESLKISCKGSGYSFT
C17B236_VH_45 EVQLVQSGAEVKKPGESLKISCKGSGYSFT
C17B239_VH_45 EVQLVQSGAEVKKPGESLKISCKGSGYSFT
C17B240_VH_45 EVQLVQSGAEVKKPGESLKISCKGSGYSFT
C17B241_VH_45 EVQLVQSGAEVKKPGESLKISCKGSGYSFT
C17B243_VH_45 EVQLVQSGAEVKKPGESLKISCKGSGYSFT
C17B244_VH_45 EVQLVQSGAEVKKPGESLKISCKGSGYSFT
C17B293_VH_46 EVQLVQSGAEVKKPGESLKISCKGSGYSFT
C17B294_VH_47 EVQLVQSGAEVKKPGESLKISCKGSGYSFT
              ******************************

31                           60
C17B234_VH_45 SYWIGWVRQMPGKGLEWMGIIDPSDSDTRY
C17B235_VH_45 SYWIGWVRQMPGKGLEWMGIIDPSDSDTRY
C17B236_VH_45 SYWIGWVRQMPGKGLEWMGIIDPSDSDTRY
C17B239_VH_45 SYWIGWVRQMPGKGLEWMGIIDPSDSDTRY
C17B240_VH_45 SYWIGWVRQMPGKGLEWMGIIDPSDSDTRY
C17B241_VH_45 SYWIGWVRQMPGKGLEWMGIIDPSDSDTRY
C17B243_VH_45 SYWIGWVRQMPGKGLEWMGIIDPSDSDTRY
C17B244_VH_45 SYWIGWVRQMPGKGLEWMGIIDPSDSDTRY
C17B293_VH_46 SYWIGWVRQMPGKGLEWMGIIDPSDSDTRY
C17B294_VH_47 SYWIGWVRQMPGKGLEWMGIIDPSDSDTRY
              ******************************
```

Figure 3 cont'd.

```
                      61                            90
C17B234_VH_45         SPSFQGQVTISADKSISTAYLQWSSLKASD
C17B235_VH_45         SPSFQGQVTISADKSISTAYLQWSSLKASD
C17B236_VH_45         SPSFQGQVTISADKSISTAYLQWSSLKASD
C17B239_VH_45         SPSFQGQVTISADKSISTAYLQWSSLKASD
C17B240_VH_45         SPSFQGQVTISADKSISTAYLQWSSLKASD
C17B241_VH_45         SPSFQGQVTISADKSISTAYLQWSSLKASD
C17B243_VH_45         SPSFQGQVTISADKSISTAYLQWSSLKASD
C17B244_VH_45         SPSFQGQVTISADKSISTAYLQWSSLKASD
C17B293_VH_46         SPSFQGQVTISADKSISTAYLQWSSLKASD
C17B294_VH_47         SPSFQGQVTISADKSISTAYLQWSSLKASD
                      ******************************

91                                  121
C17B234_VH_45         TAMYYCARVGPADVWDSFDYWGQGTLVTVSS
C17B235_VH_45         TAMYYCARVGPADVWDSFDYWGQGTLVTVSS
C17B236_VH_45         TAMYYCARVGPADVWDSFDYWGQGTLVTVSS
C17B239_VH_45         TAMYYCARVGPADVWDSFDYWGQGTLVTVSS
C17B240_VH_45         TAMYYCARVGPADVWDSFDYWGQGTLVTVSS
C17B241_VH_45         TAMYYCARVGPADVWDSFDYWGQGTLVTVSS
C17B243_VH_45         TAMYYCARVGPADVWDSFDYWGQGTLVTVSS
C17B244_VH_45         TAMYYCARVGPADVWDSFDYWGQGTLVTVSS
C17B293_VH_46         TAMYYCARVGPADVWDAFDYWGQGTLVTVSS
C17B294_VH_47         TAMYYCARVGPADVWDTFDYWGQGTLVTVSS
                      ***************:***************
```

Figure 4.

VH consensus sequence (SEQ ID NO: 75)
EVQLVQSGAEVKKPGESLKISCKGSGYSFTSYWIGWVRQMPGKGLEWMGIIDPSDSDT
RYSPSFQGQVTISADKSISTAYLQWSSLKASDTAMYYCARVGPADVWDX$_1$FDYWGQGT
LVTVSS
    wherein
    X$_1$ is S, A or T HCDR1 squence
SYWIG (SEQ ID NO: 4)

HCDR2 sequence
IIDPSDSDTRYSPSFQG (SEQ ID NO: 5)

HCDR3 consensus sequence
VGPADVWDX$_1$FDY (SEQ ID NO: 71),
    wherein
    X$_1$ is S, A or T

Figure 5.

```
                          1                              30
C17B234_VL_50    DIVMTQSPDSLAVSLGERATINCKSSQSVL
C17B235_VL_51    DIVMTQSPDSLAVSLGERATINCKSSQSVL
C17B236_VL_52    DIVMTQSPDSLAVSLGERATINCKSSQSVL
C17B239_VL_55    DIVMTQSPDSLAVSLGERATINCKSSQSVL
C17B240_VL_56    DIVMTQSPDSLAVSLGERATINCKSSQSVL
C17B241_VL_57    DIVMTQSPDSLAVSLGERATINCKSSQSVL
C17B243_VL_59    DIVMTQSPDSLAVSLGERATINCKSSQSVL
C17B244_VL_60    DIVMTQSPDSLAVSLGERATINCKSSQSVL
C17B293_VL_62    DIVMTQSPDSLAVSLGERATINCKSSQSVL
C17B294_VL_62    DIVMTQSPDSLAVSLGERATINCKSSQSVL
                 ******************************

31                             60
C17B234_VL_50    LSFDNINKLAWYQQKPGQPPKLLIYNASTR
C17B235_VL_51    YSFYNFNALAWYQQKPGQPPKLLIYHASTR
C17B236_VL_52    LSPWNSNQLAWYQQKPGQPPKLLIYGASTR
C17B239_VL_55    SSFTNTNTLAWYQQKPGQPPKLLIYHASTR
C17B240_VL_56    YSHVNYNALAWYQQKPGQPPKLLIYNASTR
C17B241_VL_57    NSFTNNNALAWYQQKPGQPPKLLIYEASTR
C17B243_VL_59    NSFDNKNDLAWYQQKPGQPPKLLIYEASTR
C17B244_VL_60    SSITNVNDLAWYQQKPGQPPKLLIYTASTR
C17B293_VL_62    LSFDNINKLAWYQQKPGQPPKLLIYDASTR
C17B294_VL_62    LSFDNINKLAWYQQKPGQPPKLLIYDASTR
                 *  *  *  ****************  ****
```

Figure 5 cont'd.

```
                       61                                    90
C17B234_VL_50          ESGVPDRFSGSGSGTDFTLTISSLQAEDVA
C17B235_VL_51          ESGVPDRFSGSGSGTDFTLTISSLQAEDVA
C17B236_VL_52          ESGVPDRFSGSGSGTDFTLTISSLQAEDVA
C17B239_VL_55          ESGVPDRFSGSGSGTDFTLTISSLQAEDVA
C17B240_VL_56          ESGVPDRFSGSGSGTDFTLTISSLQAEDVA
C17B241_VL_57          ESGVPDRFSGSGSGTDFTLTISSLQAEDVA
C17B243_VL_59          ESGVPDRFSGSGSGTDFTLTISSLQAEDVA
C17B244_VL_60          ESGVPDRFSGSGSGTDFTLTISSLQAEDVA
C17B293_VL_62          ESGVPDRFSGSGSGTDFTLTISSLQAEDVA
C17B294_VL_62          ESGVPDRFSGSGSGTDFTLTISSLQAEDVA
                       ******************************

91                    113
C17B234_VL_50          VYYCQQFYSVPSTFGQGTKVEIK
C17B235_VL_51          VYYCQQFYATPFTFGQGTKVEIK
C17B236_VL_52          VYYCQQYYLIPSTFGQGTKVEIK
C17B239_VL_55          VYYCQQYLIYPSTFGQGTKVEIK
C17B240_VL_56          VYYCQQYYTLPATFGQGTKVEIK
C17B241_VL_57          VYYCQQTNSIPLTFGQGTKVEIK
C17B243_VL_59          VYYCQQHWQTPLTFGQGTKVEIK
C17B244_VL_60          VYYCQQYYHDPFTFGQGTKVEIK
C17B293_VL_62          VYYCQQFYSVPSTFGQGTKVEIK
C17B294_VL_62          VYYCQQFYSVPSTFGQGTKVEIK
                       ******    * **********
```

Figure 6A.

VL consensus sequence (SEQ ID NO: 76):
DIVMTQSPDSLAVSLGERATINCKSSQSVLX$_1$SX$_2$X$_3$NX$_4$NX$_5$LAWYQQKPGQPPKLLIY X$_6$ASTRESGVPDRFSGSGSGTDFTLTISSLQAEDVAVYYCQQX$_7$X$_8$X$_9$X$_{10}$PX$_{11}$TFGQGT KVEIK; wherein X$_1$ is L, Y, S or N;

X$_2$ is F, P, H or I;

X$_3$ is D, Y, W, T or V;

X$_4$ is I, F, S, T, Y, N, K or V;

X$_5$ is K, A, Q, T or D;

X$_6$ is N, H, G, E, T or D;

X$_7$ is F, Y, T or H;

X$_8$ is Y, L, N or W;

X$_9$ is S, A, L, I, T, Q or H;

X$_{10}$ is V, T, I, Y, L or D; and

LCDR1 consensus sequence:
KSSQSVLX$_1$SX$_2$X$_3$NX$_4$NX$_5$LA (SEQ ID NO: 72),
    wherein
    X$_1$ is L, Y, S or N;
    X$_2$ is F, P, H or I;
    X$_3$ is D, Y, W, T or V;
    X$_4$ is I, F, S, T, Y, N, K or V; and
    X$_5$ is K, A, Q, T or D.

LCDR2 consensus sequence:
X$_1$ASTRE (SEQ ID NO: 73),
    wherein
    X$_1$ is N, H, G, E, T or D.

LCDR3 consensus sequence
QQX$_1$X$_2$X$_3$X$_4$PX$_5$T (SEQ ID NO: 74);
    wherein
    X$_1$ is F, Y, T or H;
    X$_2$ is Y, L, N or W;
    X$_3$ is S, A, L, I, T, Q or H;
    X$_4$ is V, T, I, Y, L or D; and
    X$_5$ is S, F, A or L.

SEQUENCE LISTING

<160> NUMBER OF SEQ ID NOS: 76

<210> SEQ ID NO 1
<211> LENGTH: 71
<212> TYPE: PRT
<213> ORGANISM: Homo sapiens

<400> SEQUENCE: 1

Ala Arg Gly Thr Asn Val Gly Arg Glu Cys Cys Leu Glu Tyr Phe Lys
1               5                   10                  15

Gly Ala Ile Pro Leu Arg Lys Leu Lys Thr Trp Tyr Gln Thr Ser Glu
            20                  25                  30

Asp Cys Ser Arg Asp Ala Ile Val Phe Val Thr Val Gln Gly Arg Ala
        35                  40                  45

Ile Cys Ser Asp Pro Asn Asn Lys Arg Val Lys Asn Ala Val Lys Tyr
    50                  55                  60

```
Leu Gln Ser Leu Glu Arg Ser
 65                  70

<210> SEQ ID NO 2
<211> LENGTH: 72
<212> TYPE: PRT
<213> ORGANISM: Macaca fascicularis

<400> SEQUENCE: 2

Met Ala Arg Gly Thr Asn Val Gly Arg Glu Cys Cys Leu Lys Tyr Phe
 1               5                  10                  15

Lys Gly Ala Ile Pro Leu Arg Lys Leu Lys Thr Trp Tyr Gln Thr Ser
             20                  25                  30

Glu Asp Cys Ser Arg Asp Ala Ile Val Phe Val Thr Val Gln Asn Lys
         35                  40                  45

Ala Ile Cys Ser Asp Pro Asn Asp Lys Lys Val Lys Lys Ala Leu Lys
     50                  55                  60

Tyr Leu Gln Ser Leu Glu Arg Ser
 65                  70

<210> SEQ ID NO 3
<211> LENGTH: 69
<212> TYPE: PRT
<213> ORGANISM: Macaca fascicularis

<400> SEQUENCE: 3

Gly Pro Tyr Gly Ala Asn Met Glu Asp Ser Val Cys Cys Arg Asp Tyr
 1               5                  10                  15

Val Arg Tyr Arg Met Pro Leu Arg Val Val Lys His Phe Tyr Trp Thr
             20                  25                  30

Ser Asp Ser Cys Pro Arg Pro Gly Val Val Leu Leu Thr Ser Arg Asp
         35                  40                  45

Lys Glu Ile Cys Ala Asp Pro Arg Val Pro Trp Val Lys Met Ile Leu
     50                  55                  60

Asn Lys Leu Ser Gln
 65

<210> SEQ ID NO 4
<211> LENGTH: 5
<212> TYPE: PRT
<213> ORGANISM: Artificial sequence
<220> FEATURE:
<223> OTHER INFORMATION: HCDR1 of C17F24

<400> SEQUENCE: 4

Ser Tyr Trp Ile Gly
 1               5

<210> SEQ ID NO 5
<211> LENGTH: 17
<212> TYPE: PRT
<213> ORGANISM: Artificial sequence
<220> FEATURE:
<223> OTHER INFORMATION: HCDR2 of C17F24

<400> SEQUENCE: 5

Ile Ile Asp Pro Ser Asp Ser Asp Thr Arg Tyr Ser Pro Ser Phe Gln
 1               5                  10                  15

Gly

<210> SEQ ID NO 6
```

```
<211> LENGTH: 12
<212> TYPE: PRT
<213> ORGANISM: Artificial sequence
<220> FEATURE:
<223> OTHER INFORMATION: HCDR3 of C17F24

<400> SEQUENCE: 6

Val Gly Pro Ala Asp Val Trp Asp Ser Phe Asp Tyr
1               5                   10

<210> SEQ ID NO 7
<211> LENGTH: 17
<212> TYPE: PRT
<213> ORGANISM: Artificial sequence
<220> FEATURE:
<223> OTHER INFORMATION: LCDR1 of C17F24

<400> SEQUENCE: 7

Lys Ser Ser Gln Ser Val Leu Tyr Ser Ser Asn Asn Lys Asn Tyr Leu
1               5                   10                  15

Ala

<210> SEQ ID NO 8
<211> LENGTH: 17
<212> TYPE: PRT
<213> ORGANISM: Artificial sequence
<220> FEATURE:
<223> OTHER INFORMATION: LCDR1 of C17B234

<400> SEQUENCE: 8

Lys Ser Ser Gln Ser Val Leu Leu Ser Phe Asp Asn Ile Asn Lys Leu
1               5                   10                  15

Ala

<210> SEQ ID NO 9
<211> LENGTH: 17
<212> TYPE: PRT
<213> ORGANISM: Artificial sequence
<220> FEATURE:
<223> OTHER INFORMATION: LCDR1 fo C17B235

<400> SEQUENCE: 9

Lys Ser Ser Gln Ser Val Leu Tyr Ser Phe Tyr Asn Phe Asn Ala Leu
1               5                   10                  15

Ala

<210> SEQ ID NO 10
<211> LENGTH: 17
<212> TYPE: PRT
<213> ORGANISM: Artificial sequence
<220> FEATURE:
<223> OTHER INFORMATION: LCDR1 of C17B236

<400> SEQUENCE: 10

Lys Ser Ser Gln Ser Val Leu Leu Ser Pro Trp Asn Ser Asn Gln Leu
1               5                   10                  15

Ala

<210> SEQ ID NO 11
<211> LENGTH: 17
<212> TYPE: PRT
<213> ORGANISM: Artificial sequence
<220> FEATURE:
<223> OTHER INFORMATION: LCDR1 of C17B237
```

```
<400> SEQUENCE: 11

Lys Ser Ser Gln Ser Val Leu Thr Ser Tyr Asn Asn Ser Asn Tyr Leu
1               5                   10                  15
Ala

<210> SEQ ID NO 12
<211> LENGTH: 17
<212> TYPE: PRT
<213> ORGANISM: Artificial sequence
<220> FEATURE:
<223> OTHER INFORMATION: LCDR1 of C17B238

<400> SEQUENCE: 12

Lys Ser Ser Gln Ser Val Leu Ile Ser Ala Phe Asn Gln Asn Pro Leu
1               5                   10                  15
Ala

<210> SEQ ID NO 13
<211> LENGTH: 17
<212> TYPE: PRT
<213> ORGANISM: Artificial sequence
<220> FEATURE:
<223> OTHER INFORMATION: LCDR1 of C17B239

<400> SEQUENCE: 13

Lys Ser Ser Gln Ser Val Leu Ser Ser Phe Thr Asn Thr Asn Thr Leu
1               5                   10                  15
Ala

<210> SEQ ID NO 14
<211> LENGTH: 17
<212> TYPE: PRT
<213> ORGANISM: Artificial sequence
<220> FEATURE:
<223> OTHER INFORMATION: LCDR1 of C17B240

<400> SEQUENCE: 14

Lys Ser Ser Gln Ser Val Leu Tyr Ser His Val Asn Tyr Asn Ala Leu
1               5                   10                  15
Ala

<210> SEQ ID NO 15
<211> LENGTH: 17
<212> TYPE: PRT
<213> ORGANISM: Artificial sequence
<220> FEATURE:
<223> OTHER INFORMATION: LCDR1 of C17B241

<400> SEQUENCE: 15

Lys Ser Ser Gln Ser Val Leu Asn Ser Phe Thr Asn Asn Asn Ala Leu
1               5                   10                  15
Ala

<210> SEQ ID NO 16
<211> LENGTH: 17
<212> TYPE: PRT
<213> ORGANISM: Artificial sequence
<220> FEATURE:
<223> OTHER INFORMATION: LCDR1 of C17B242

<400> SEQUENCE: 16

Lys Ser Ser Gln Ser Val Leu Phe Ser His Asp Asn Leu Asn Thr Leu
1               5                   10                  15
```

Ala

<210> SEQ ID NO 17
<211> LENGTH: 17
<212> TYPE: PRT
<213> ORGANISM: Artificial sequence
<220> FEATURE:
<223> OTHER INFORMATION: LCDR1 of C17B243

<400> SEQUENCE: 17

Lys Ser Ser Gln Ser Val Leu Asn Ser Phe Asp Asn Lys Asn Asp Leu
1               5                   10                  15
Ala

<210> SEQ ID NO 18
<211> LENGTH: 17
<212> TYPE: PRT
<213> ORGANISM: Artificial sequence
<220> FEATURE:
<223> OTHER INFORMATION: LCDR1 of C17B244

<400> SEQUENCE: 18

Lys Ser Ser Gln Ser Val Leu Ser Ser Ile Thr Asn Val Asn Asp Leu
1               5                   10                  15
Ala

<210> SEQ ID NO 19
<211> LENGTH: 7
<212> TYPE: PRT
<213> ORGANISM: Artificial sequence
<220> FEATURE:
<223> OTHER INFORMATION: LCDR2 fo C17F24

<400> SEQUENCE: 19

Trp Ala Ser Thr Arg Glu Ser
1               5

<210> SEQ ID NO 20
<211> LENGTH: 7
<212> TYPE: PRT
<213> ORGANISM: Artificial sequence
<220> FEATURE:
<223> OTHER INFORMATION: LCDR2 of C17B234

<400> SEQUENCE: 20

Asn Ala Ser Thr Arg Glu Ser
1               5

<210> SEQ ID NO 21
<211> LENGTH: 7
<212> TYPE: PRT
<213> ORGANISM: Artificial sequence
<220> FEATURE:
<223> OTHER INFORMATION: LCDR2 fo C17B235

<400> SEQUENCE: 21

His Ala Ser Thr Arg Glu Ser
1               5

<210> SEQ ID NO 22
<211> LENGTH: 7
<212> TYPE: PRT
<213> ORGANISM: Artificial sequence
<220> FEATURE:
<223> OTHER INFORMATION: LCDR2 of C17B236

```
<400> SEQUENCE: 22

Gly Ala Ser Thr Arg Glu Ser
1               5

<210> SEQ ID NO 23
<211> LENGTH: 7
<212> TYPE: PRT
<213> ORGANISM: Artificial sequence
<220> FEATURE:
<223> OTHER INFORMATION: LCDR2 of C17B237

<400> SEQUENCE: 23

Leu Ala Ser Thr Arg Glu Ser
1               5

<210> SEQ ID NO 24
<211> LENGTH: 7
<212> TYPE: PRT
<213> ORGANISM: Artificial sequence
<220> FEATURE:
<223> OTHER INFORMATION: LCDR2 of C17B238

<400> SEQUENCE: 24

Asp Ala Ser Thr Arg Glu Ser
1               5

<210> SEQ ID NO 25
<211> LENGTH: 7
<212> TYPE: PRT
<213> ORGANISM: Artificial sequence
<220> FEATURE:
<223> OTHER INFORMATION: LCDR2 of C17B241

<400> SEQUENCE: 25

Glu Ala Ser Thr Arg Glu Ser
1               5

<210> SEQ ID NO 26
<211> LENGTH: 7
<212> TYPE: PRT
<213> ORGANISM: Artificial sequence
<220> FEATURE:
<223> OTHER INFORMATION: LCDR2 of C17B244

<400> SEQUENCE: 26

Thr Ala Ser Thr Arg Glu Ser
1               5

<210> SEQ ID NO 27
<211> LENGTH: 9
<212> TYPE: PRT
<213> ORGANISM: Artificial sequence
<220> FEATURE:
<223> OTHER INFORMATION: LCDR3 of C17F24

<400> SEQUENCE: 27

Gln Gln Tyr Tyr Ser Thr Pro Leu Thr
1               5

<210> SEQ ID NO 28
<211> LENGTH: 9
<212> TYPE: PRT
<213> ORGANISM: Artificial sequence
<220> FEATURE:
<223> OTHER INFORMATION: LCDR3 of C17B234
```

```
<400> SEQUENCE: 28

Gln Gln Phe Tyr Ser Val Pro Ser Thr
1               5

<210> SEQ ID NO 29
<211> LENGTH: 9
<212> TYPE: PRT
<213> ORGANISM: Artificial sequence
<220> FEATURE:
<223> OTHER INFORMATION: LCDR3 of C17B235

<400> SEQUENCE: 29

Gln Gln Phe Tyr Ala Thr Pro Phe Thr
1               5

<210> SEQ ID NO 30
<211> LENGTH: 9
<212> TYPE: PRT
<213> ORGANISM: Artificial sequence
<220> FEATURE:
<223> OTHER INFORMATION: LCDR3 of C17B236

<400> SEQUENCE: 30

Gln Gln Tyr Tyr Leu Ile Pro Ser Thr
1               5

<210> SEQ ID NO 31
<211> LENGTH: 9
<212> TYPE: PRT
<213> ORGANISM: Artificial sequence
<220> FEATURE:
<223> OTHER INFORMATION: LCDR3 of C17B237

<400> SEQUENCE: 31

Gln Gln Tyr Leu Ser Pro Pro Ser Thr
1               5

<210> SEQ ID NO 32
<211> LENGTH: 9
<212> TYPE: PRT
<213> ORGANISM: Artificial sequence
<220> FEATURE:
<223> OTHER INFORMATION: LCDR3 of C17B238

<400> SEQUENCE: 32

Gln Gln Tyr Gln Phe Ile Pro Phe Thr
1               5

<210> SEQ ID NO 33
<211> LENGTH: 9
<212> TYPE: PRT
<213> ORGANISM: Artificial sequence
<220> FEATURE:
<223> OTHER INFORMATION: LCDR3 of C17B239

<400> SEQUENCE: 33

Gln Gln Tyr Leu Ile Tyr Pro Ser Thr
1               5

<210> SEQ ID NO 34
<211> LENGTH: 9
<212> TYPE: PRT
<213> ORGANISM: Artificial sequence
<220> FEATURE:
<223> OTHER INFORMATION: LCDR3 fo C17B240

<400> SEQUENCE: 34
```

```
Gln Gln Tyr Tyr Thr Leu Pro Ala Thr
1               5

<210> SEQ ID NO 35
<211> LENGTH: 9
<212> TYPE: PRT
<213> ORGANISM: Artificial sequence
<220> FEATURE:
<223> OTHER INFORMATION: LCDR3 of C17B241

<400> SEQUENCE: 35

Gln Gln Thr Asn Ser Ile Pro Leu Thr
1               5

<210> SEQ ID NO 36
<211> LENGTH: 9
<212> TYPE: PRT
<213> ORGANISM: Artificial sequence
<220> FEATURE:
<223> OTHER INFORMATION: LCDR3 of C17B242

<400> SEQUENCE: 36

Gln Gln Tyr Tyr Ala Val Pro Gln Thr
1               5

<210> SEQ ID NO 37
<211> LENGTH: 9
<212> TYPE: PRT
<213> ORGANISM: Artificial sequence
<220> FEATURE:
<223> OTHER INFORMATION: LCDR3 of C17B243

<400> SEQUENCE: 37

Gln Gln His Trp Gln Thr Pro Leu Thr
1               5

<210> SEQ ID NO 38
<211> LENGTH: 9
<212> TYPE: PRT
<213> ORGANISM: Artificial sequence
<220> FEATURE:
<223> OTHER INFORMATION: LCDR3 of C17B244

<400> SEQUENCE: 38

Gln Gln Tyr Tyr His Asp Pro Phe Thr
1               5

<210> SEQ ID NO 39
<211> LENGTH: 7
<212> TYPE: PRT
<213> ORGANISM: Artificial sequence
<220> FEATURE:
<223> OTHER INFORMATION: LCDR2 of C17B257

<400> SEQUENCE: 39

Ala Ala Ser Thr Arg Glu Ser
1               5

<210> SEQ ID NO 40
<211> LENGTH: 7
<212> TYPE: PRT
<213> ORGANISM: Artificial sequence
<220> FEATURE:
<223> OTHER INFORMATION: LCDR2 of C17B262

<400> SEQUENCE: 40
```

Ser Ala Ser Thr Arg Glu Ser
1               5

<210> SEQ ID NO 41
<211> LENGTH: 7
<212> TYPE: PRT
<213> ORGANISM: Artificial sequence
<220> FEATURE:
<223> OTHER INFORMATION: LCDR2 fo C17B264

<400> SEQUENCE: 41

Ile Ala Ser Thr Arg Glu Ser
1               5

<210> SEQ ID NO 42
<211> LENGTH: 12
<212> TYPE: PRT
<213> ORGANISM: Artificial sequence
<220> FEATURE:
<223> OTHER INFORMATION: HCDR3 of C17B293

<400> SEQUENCE: 42

Val Gly Pro Ala Asp Val Trp Asp Ala Phe Asp Tyr
1               5                   10

<210> SEQ ID NO 43
<211> LENGTH: 12
<212> TYPE: PRT
<213> ORGANISM: Artificial sequence
<220> FEATURE:
<223> OTHER INFORMATION: HCDR3 of C17B294

<400> SEQUENCE: 43

Val Gly Pro Ala Asp Val Trp Asp Thr Phe Asp Tyr
1               5                   10

<210> SEQ ID NO 44
<211> LENGTH: 12
<212> TYPE: PRT
<213> ORGANISM: Artificial sequence
<220> FEATURE:
<223> OTHER INFORMATION: HCDR3 of C17B295

<400> SEQUENCE: 44

Val Gly Pro Ala Asp Val Trp Glu Ser Phe Asp Tyr
1               5                   10

<210> SEQ ID NO 45
<211> LENGTH: 121
<212> TYPE: PRT
<213> ORGANISM: Artificial sequence
<220> FEATURE:
<223> OTHER INFORMATION: VH of C17F24, C17B234, C17B235, C17B236,
     C17B237, C17B238, C17B239, C17B240, C17B241,
     C17B242, C17B243, C17B244, C17B257, C17B258,
     C17B260, C17B262, C17B266, C17B264

<400> SEQUENCE: 45

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Gly Pro Ala Asp Val Trp Asp Ser Phe Asp Tyr Trp Gly
            100                 105                 110

Gln Gly Thr Leu Val Thr Val Ser Ser
        115                 120
```

<210> SEQ ID NO 46
<211> LENGTH: 121
<212> TYPE: PRT
<213> ORGANISM: Artificial sequence
<220> FEATURE:
<223> OTHER INFORMATION: VH of C17M293

<400> SEQUENCE: 46

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Gly Pro Ala Asp Val Trp Asp Ala Phe Asp Tyr Trp Gly
            100                 105                 110

Gln Gly Thr Leu Val Thr Val Ser Ser
        115                 120
```

<210> SEQ ID NO 47
<211> LENGTH: 121
<212> TYPE: PRT
<213> ORGANISM: Artificial sequence
<220> FEATURE:
<223> OTHER INFORMATION: VH of C17B294

<400> SEQUENCE: 47

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Gly Pro Ala Asp Val Trp Asp Thr Phe Asp Tyr Trp Gly
            100                 105                 110

Gln Gly Thr Leu Val Thr Val Ser Ser
```

<210> SEQ ID NO 48
<211> LENGTH: 121
<212> TYPE: PRT
<213> ORGANISM: Artificial sequence
<220> FEATURE:
<223> OTHER INFORMATION: VH of C17B295

<400> SEQUENCE: 48

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Gly Pro Ala Asp Val Trp Glu Ser Phe Asp Tyr Trp Gly
            100                 105                 110

Gln Gly Thr Leu Val Thr Val Ser Ser
        115                 120

<210> SEQ ID NO 49
<211> LENGTH: 113
<212> TYPE: PRT
<213> ORGANISM: Artificial sequence
<220> FEATURE:
<223> OTHER INFORMATION: VL of C17F24

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 50
<211> LENGTH: 113
<212> TYPE: PRT
<213> ORGANISM: Artificial sequence
<220> FEATURE:
<223> OTHER INFORMATION: VL of C17B234

<400> SEQUENCE: 50

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Leu Ser
            20                  25                  30

Phe Asp Asn Ile Asn Lys Leu Ala Trp Tyr Gln Gln Lys Pro Gly Gln
        35                  40                  45

Pro Pro Lys Leu Leu Ile Tyr Asn Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Val Pro Ser Thr Phe Gly Gln Gly Thr Lys Val Glu Ile
            100                 105                 110

Lys

<210> SEQ ID NO 51
<211> LENGTH: 113
<212> TYPE: PRT
<213> ORGANISM: Artificial sequence
<220> FEATURE:
<223> OTHER INFORMATION: VL of C17B235

<400> SEQUENCE: 51

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Phe Tyr Asn Phe Asn Ala Leu Ala Trp Tyr Gln Gln Lys Pro Gly Gln
        35                  40                  45

Pro Pro Lys Leu Leu Ile Tyr His Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ala Thr Pro Phe Thr Phe Gly Gln Gly Thr Lys Val Glu Ile
            100                 105                 110

Lys

<210> SEQ ID NO 52
<211> LENGTH: 113
<212> TYPE: PRT
<213> ORGANISM: Artificial sequence
<220> FEATURE:
<223> OTHER INFORMATION: VL of C17B236

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Leu Ser
            20                  25                  30

Pro Trp Asn Ser Asn Gln Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
50                  55                  60

Pro Asp Arg Phe Ser Gly Ser Gly Ser Gly Thr Asp Phe Thr Leu Thr

```
                65                  70                  75                  80
Ile Ser Ser Leu Gln Ala Glu Asp Val Ala Val Tyr Tyr Cys Gln Gln
                    85                  90                  95

Tyr Tyr Leu Ile Pro Ser Thr Phe Gly Gln Gly Thr Lys Val Glu Ile
            100                 105                 110

Lys

<210> SEQ ID NO 53
<211> LENGTH: 113
<212> TYPE: PRT
<213> ORGANISM: Artificial sequence
<220> FEATURE:
<223> OTHER INFORMATION: VL of C17B237

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Thr Ser
            20                  25                  30

Tyr Asn Asn Ser Asn Tyr Leu Ala Trp Tyr Gln Gln Lys Pro Gly Gln
        35                  40                  45

Pro Pro Lys Leu Leu Ile Tyr Leu Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                    85                  90                  95

Tyr Leu Ser Pro Pro Ser Thr Phe Gly Gln Gly Thr Lys Val Glu Ile
            100                 105                 110

Lys

<210> SEQ ID NO 54
<211> LENGTH: 113
<212> TYPE: PRT
<213> ORGANISM: Artificial sequence
<220> FEATURE:
<223> OTHER INFORMATION: VL of C17B238

<400> SEQUENCE: 54

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ile Ser
            20                  25                  30

Ala Phe Asn Gln Asn Pro Leu Ala Trp Tyr Gln Gln Lys Pro Gly Gln
        35                  40                  45

Pro Pro Lys Leu Leu Ile Tyr Asp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                    85                  90                  95

Tyr Gln Phe Ile Pro Phe Thr Phe Gly Gln Gly Thr Lys Val Glu Ile
            100                 105                 110

Lys

<210> SEQ ID NO 55
<211> LENGTH: 113
```

```
<212> TYPE: PRT
<213> ORGANISM: Artificial sequence
<220> FEATURE:
<223> OTHER INFORMATION: VL of C17B239

<400> SEQUENCE: 55
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ser Ser
            20                  25                  30

Phe Thr Asn Thr Asn Thr Leu Ala Trp Tyr Gln Gln Lys Pro Gly Gln
        35                  40                  45

Pro Pro Lys Leu Leu Ile Tyr His Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Leu Ile Tyr Pro Ser Thr Phe Gly Gln Gly Thr Lys Val Glu Ile
            100                 105                 110

Lys

```
<210> SEQ ID NO 56
<211> LENGTH: 113
<212> TYPE: PRT
<213> ORGANISM: Artificial sequence
<220> FEATURE:
<223> OTHER INFORMATION: VL of C17B240

<400> SEQUENCE: 56
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

His Val Asn Tyr Asn Ala Leu Ala Trp Tyr Gln Gln Lys Pro Gly Gln
        35                  40                  45

Pro Pro Lys Leu Leu Ile Tyr Asn Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Leu Pro Ala Thr Phe Gly Gln Gly Thr Lys Val Glu Ile
            100                 105                 110

Lys

```
<210> SEQ ID NO 57
<211> LENGTH: 113
<212> TYPE: PRT
<213> ORGANISM: Artificial sequence
<220> FEATURE:
<223> OTHER INFORMATION: VL of C17B241

<400> SEQUENCE: 57
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

```
Phe Thr Asn Asn Ala Leu Ala Trp Tyr Gln Gln Lys Pro Gly Gln
            35                  40                  45

Pro Pro Lys Leu Leu Ile Tyr Glu Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Thr Asn Ser Ile Pro Leu Thr Phe Gly Gln Gly Thr Lys Val Glu Ile
            100                 105                 110

Lys

<210> SEQ ID NO 58
<211> LENGTH: 113
<212> TYPE: PRT
<213> ORGANISM: Artificial sequence
<220> FEATURE:
<223> OTHER INFORMATION: VL of C17B242

<400> SEQUENCE: 58

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Phe Ser
             20                  25                  30

His Asp Asn Leu Asn Thr Leu Ala Trp Tyr Gln Gln Lys Pro Gly Gln
            35                  40                  45

Pro Pro Lys Leu Leu Ile Tyr His Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ala Val Pro Gln Thr Phe Gly Gln Gly Thr Lys Val Glu Ile
            100                 105                 110

Lys

<210> SEQ ID NO 59
<211> LENGTH: 113
<212> TYPE: PRT
<213> ORGANISM: Artificial sequence
<220> FEATURE:
<223> OTHER INFORMATION: VL of C17B243

<400> SEQUENCE: 59

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Asn Ser
             20                  25                  30

Phe Asp Asn Lys Asn Asp Leu Ala Trp Tyr Gln Gln Lys Pro Gly Gln
            35                  40                  45

Pro Pro Lys Leu Leu Ile Tyr Glu Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

His Trp Gln Thr Pro Leu Thr Phe Gly Gln Gly Thr Lys Val Glu Ile
```

<210> SEQ ID NO 60
<211> LENGTH: 113
<212> TYPE: PRT
<213> ORGANISM: Artificial sequence
<220> FEATURE:
<223> OTHER INFORMATION: VL of C17B244

<400> SEQUENCE: 60

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Ser Ser
            20                  25                  30
Ile Thr Asn Val Asn Asp Leu Ala Trp Tyr Gln Lys Pro Gly Gln
        35                  40                  45
Pro Pro Lys Leu Leu Ile Tyr Thr Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr His Asp Pro Phe Thr Phe Gly Gln Gly Thr Lys Val Glu Ile
                100                 105                 110
Lys
```

<210> SEQ ID NO 61
<211> LENGTH: 113
<212> TYPE: PRT
<213> ORGANISM: Artificial sequence
<220> FEATURE:
<223> OTHER INFORMATION: VL of C17B257

<400> SEQUENCE: 61

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Leu Ser
            20                  25                  30
Phe Asp Asn Ile Asn Lys Leu Ala Trp Tyr Gln Gln Lys Pro Gly Gln
        35                  40                  45
Pro Pro Lys Leu Leu Ile Tyr Ala Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Phe Tyr Ser Val Pro Ser Thr Phe Gly Gln Gly Thr Lys Val Glu Ile
                100                 105                 110
Lys
```

<210> SEQ ID NO 62
<211> LENGTH: 113
<212> TYPE: PRT
<213> ORGANISM: Artificial sequence
<220> FEATURE:
<223> OTHER INFORMATION: VL of C17B258

<400> SEQUENCE: 62

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Leu Ser
            20                  25                  30

Phe Asp Asn Ile Asn Lys Leu Ala Trp Tyr Gln Gln Lys Pro Gly Gln
        35                  40                  45

Pro Pro Lys Leu Leu Ile Tyr Asp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Val Pro Ser Thr Phe Gly Gln Gly Thr Lys Val Glu Ile
            100                 105                 110

Lys

<210> SEQ ID NO 63
<211> LENGTH: 113
<212> TYPE: PRT
<213> ORGANISM: Artificial sequence
<220> FEATURE:
<223> OTHER INFORMATION: VL of C17B260

<400> SEQUENCE: 63

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Leu Ser
            20                  25                  30

Phe Asp Asn Ile Asn Lys Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Val Pro Ser Thr Phe Gly Gln Gly Thr Lys Val Glu Ile
            100                 105                 110

Lys

<210> SEQ ID NO 64
<211> LENGTH: 113
<212> TYPE: PRT
<213> ORGANISM: Artificial sequence
<220> FEATURE:
<223> OTHER INFORMATION: VL of C17B262

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Leu Ser
            20                  25                  30

Phe Asp Asn Ile Asn Lys Leu Ala Trp Tyr Gln Gln Lys Pro Gly Gln
        35                  40                  45

Pro Pro Lys Leu Leu Ile Tyr Ser Ala Ser Thr Arg Glu Ser Gly Val
50                  55                  60

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Phe Tyr Ser Val Pro Ser Thr Phe Gly Gln Gly Thr Lys Val Glu Ile
                100                 105                 110

Lys

<210> SEQ ID NO 65
<211> LENGTH: 113
<212> TYPE: PRT
<213> ORGANISM: Artificial sequence
<220> FEATURE:
<223> OTHER INFORMATION: VL of C17B263

<400> SEQUENCE: 65

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Leu Ser
                 20                  25                  30

Phe Asp Asn Ile Asn Lys Leu Ala Trp Tyr Gln Gln Lys Pro Gly Gln
                 35                  40                  45

Pro Pro Lys Leu Leu Ile Tyr Thr Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Phe Tyr Ser Val Pro Ser Thr Phe Gly Gln Gly Thr Lys Val Glu Ile
                100                 105                 110

Lys

<210> SEQ ID NO 66
<211> LENGTH: 113
<212> TYPE: PRT
<213> ORGANISM: Artificial sequence
<220> FEATURE:
<223> OTHER INFORMATION: VL of C17B264

<400> SEQUENCE: 66

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Leu Ser
                 20                  25                  30

Phe Asp Asn Ile Asn Lys Leu Ala Trp Tyr Gln Gln Lys Pro Gly Gln
                 35                  40                  45

Pro Pro Lys Leu Leu Ile Tyr Ile Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Phe Tyr Ser Val Pro Ser Thr Phe Gly Gln Gly Thr Lys Val Glu Ile
                100                 105                 110

Lys

<210> SEQ ID NO 67
```

<211> LENGTH: 447
<212> TYPE: PRT
<213> ORGANISM: Artificial sequence
<220> FEATURE:
<223> OTHER INFORMATION: CB302 HC

<400> SEQUENCE: 67

```
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Asp Pro Ser Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Val Gly Pro Ala Asp Val Trp Asp Ala Phe Asp Tyr Trp Gly
            100                 105                 110
Gln Gly Thr Leu Val Thr Val Ser Ala Ser Thr Lys Gly Pro Ser
        115                 120                 125
Val Phe Pro Leu Ala Pro Cys Ser Arg Ser Thr Ser Glu Ser Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Thr Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Cys Cys
    210                 215                 220
Val Glu Cys Pro Pro Cys Pro Ala Pro Ala Ala Ser Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Ala Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Phe Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 68
<211> LENGTH: 220
<212> TYPE: PRT
<213> ORGANISM: Artificial sequence
<220> FEATURE:
<223> OTHER INFORMATION: CB302 LC

<400> SEQUENCE: 68

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Leu Ser
            20                  25                  30

Phe Asp Asn Ile Asn Lys Leu Ala Trp Tyr Gln Gln Lys Pro Gly Gln
        35                  40                  45

Pro Pro Lys Leu Leu Ile Tyr Asp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Val Pro Ser Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 69
<211> LENGTH: 447
<212> TYPE: PRT
<213> ORGANISM: Artificial sequence
<220> FEATURE:
<223> OTHER INFORMATION: CB301 HC

<400> SEQUENCE: 69

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
```

-continued

```
                20                  25                  30
Trp Ile Gly Trp Val Arg Gln Met Pro Gly Lys Gly Leu Glu Trp Met
             35                  40                  45
Gly Ile Ile Asp Pro Ser Asp Ser Asp Thr Arg Tyr Ser Pro Ser Phe
         50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Val Gly Pro Ala Asp Val Trp Asp Thr Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Thr Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Cys Cys
    210                 215                 220
Val Glu Cys Pro Pro Cys Pro Ala Pro Pro Ala Ala Ala Ser Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Ala Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Phe Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445
```

```
<210> SEQ ID NO 70
<211> LENGTH: 220
<212> TYPE: PRT
<213> ORGANISM: Artificial sequence
<220> FEATURE:
<223> OTHER INFORMATION: CB301 LC

<400> SEQUENCE: 70

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Leu Ser
            20                  25                  30

Phe Asp Asn Ile Asn Lys Leu Ala Trp Tyr Gln Gln Lys Pro Gly Gln
        35                  40                  45

Pro Pro Lys Leu Leu Ile Tyr Asp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Val Pro Ser Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 71
<211> LENGTH: 12
<212> TYPE: PRT
<213> ORGANISM: Artificial sequence
<220> FEATURE:
<223> OTHER INFORMATION: HCDR3 consensus sequence
<220> FEATURE:
<221> NAME/KEY: MISC_FEATURE
<222> LOCATION: (9)..(9)
<223> OTHER INFORMATION: Xaa may be Ser, Ala or Thr

<400> SEQUENCE: 71

Val Gly Pro Ala Asp Val Trp Asp Xaa Phe Asp Tyr
1               5                   10

<210> SEQ ID NO 72
<211> LENGTH: 17
<212> TYPE: PRT
<213> ORGANISM: Artificial sequence
<220> FEATURE:
<223> OTHER INFORMATION: LCDR1 consensus sequence
<220> FEATURE:
<221> NAME/KEY: MISC_FEATURE
```

```
<222> LOCATION: (8)..(8)
<223> OTHER INFORMATION: Xaa may be Leu, Tyr, Ser or Asn
<220> FEATURE:
<221> NAME/KEY: MISC_FEATURE
<222> LOCATION: (10)..(10)
<223> OTHER INFORMATION: Xaa may be Phe, Pro, His or Ile
<220> FEATURE:
<221> NAME/KEY: MISC_FEATURE
<222> LOCATION: (11)..(11)
<223> OTHER INFORMATION: Xaa may be Asp, Tyr, Trp, Thr or Val
<220> FEATURE:
<221> NAME/KEY: MISC_FEATURE
<222> LOCATION: (13)..(13)
<223> OTHER INFORMATION: Xaa may be Ile, Phe, Ser, Thr, Tyr, Asn, Lys or
      Val
<220> FEATURE:
<221> NAME/KEY: MISC_FEATURE
<222> LOCATION: (15)..(15)
<223> OTHER INFORMATION: Xaa may be Lys, Ala, Qln, Thr or Asp

<400> SEQUENCE: 72

Lys Ser Ser Gln Ser Val Leu Xaa Ser Xaa Xaa Asn Xaa Asn Xaa Leu
1               5                   10                  15

Ala

<210> SEQ ID NO 73
<211> LENGTH: 6
<212> TYPE: PRT
<213> ORGANISM: Artificial sequence
<220> FEATURE:
<223> OTHER INFORMATION: LCDR2 consensus sequence
<220> FEATURE:
<221> NAME/KEY: MISC_FEATURE
<222> LOCATION: (1)..(1)
<223> OTHER INFORMATION: Xaa may be Asn, His, Gly, Glu, Thr or Asp

<400> SEQUENCE: 73

Xaa Ala Ser Thr Arg Glu
1               5

<210> SEQ ID NO 74
<211> LENGTH: 9
<212> TYPE: PRT
<213> ORGANISM: Artificial sequence
<220> FEATURE:
<223> OTHER INFORMATION: LCDR3 consensus sequence
<220> FEATURE:
<221> NAME/KEY: MISC_FEATURE
<222> LOCATION: (3)..(3)
<223> OTHER INFORMATION: Xaa may be Phe, Tyr, Thr or His
<220> FEATURE:
<221> NAME/KEY: MISC_FEATURE
<222> LOCATION: (4)..(4)
<223> OTHER INFORMATION: Xaa may be Tyr, Leu, Asn or Trp
<220> FEATURE:
<221> NAME/KEY: MISC_FEATURE
<222> LOCATION: (5)..(5)
<223> OTHER INFORMATION: Xaa may be Ser, Ala, Leu, Ile, Thr, Qln or His
<220> FEATURE:
<221> NAME/KEY: MISC_FEATURE
<222> LOCATION: (6)..(6)
<223> OTHER INFORMATION: Xaa may be Val, Thr, Ile, Tyr, Leu or Asp
<220> FEATURE:
<221> NAME/KEY: MISC_FEATURE
<222> LOCATION: (8)..(8)
<223> OTHER INFORMATION: Xaa may be Ser, Phe, Ala or Leu

<400> SEQUENCE: 74

Gln Gln Xaa Xaa Xaa Xaa Pro Xaa Thr
1               5

<210> SEQ ID NO 75
```

-continued

```
<211> LENGTH: 121
<212> TYPE: PRT
<213> ORGANISM: Artificial sequence
<220> FEATURE:
<223> OTHER INFORMATION: VH consensus sequence
<220> FEATURE:
<221> NAME/KEY: MISC_FEATURE
<222> LOCATION: (107)..(107)
<223> OTHER INFORMATION: Xaa may be Ser, Ala or Thr

<400> SEQUENCE: 75

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Gly Pro Ala Asp Val Trp Asp Xaa Phe Asp Tyr Trp Gly
            100                 105                 110

Gln Gly Thr Leu Val Thr Val Ser Ser
        115                 120

<210> SEQ ID NO 76
<211> LENGTH: 113
<212> TYPE: PRT
<213> ORGANISM: Artificial sequence
<220> FEATURE:
<223> OTHER INFORMATION: VL consensus sequence
<220> FEATURE:
<221> NAME/KEY: MISC_FEATURE
<222> LOCATION: (31)..(31)
<223> OTHER INFORMATION: Xaa may be Leu, Tyr, Ser or Asn
<220> FEATURE:
<221> NAME/KEY: MISC_FEATURE
<222> LOCATION: (33)..(33)
<223> OTHER INFORMATION: Xaa may be Phe,Pro, His or Ile
<220> FEATURE:
<221> NAME/KEY: MISC_FEATURE
<222> LOCATION: (34)..(34)
<223> OTHER INFORMATION: Xaa may be Asp, Tyr, Trp, Thr or Val
<220> FEATURE:
<221> NAME/KEY: MISC_FEATURE
<222> LOCATION: (36)..(36)
<223> OTHER INFORMATION: Xaa may be Ile, Phe, Ser, Thr, Tyr, Asn, Lys or
      Val
<220> FEATURE:
<221> NAME/KEY: MISC_FEATURE
<222> LOCATION: (38)..(38)
<223> OTHER INFORMATION: Xaa may be Lys, Ala, Qln, Thr or Asp
<220> FEATURE:
<221> NAME/KEY: MISC_FEATURE
<222> LOCATION: (56)..(56)
<223> OTHER INFORMATION: Xaa may be Asn, His, Gly, Glu, Thr or Asp
<220> FEATURE:
<221> NAME/KEY: MISC_FEATURE
<222> LOCATION: (97)..(97)
<223> OTHER INFORMATION: Xaa may be Phe, Tyr, Thr or His
<220> FEATURE:
<221> NAME/KEY: MISC_FEATURE
<222> LOCATION: (98)..(98)
<223> OTHER INFORMATION: Xaa may be Tyr, Leu, Asn or Trp
<220> FEATURE:
<221> NAME/KEY: MISC_FEATURE
<222> LOCATION: (99)..(99)
```

```
<223> OTHER INFORMATION: Xaa may be Ser, Ala, Leu, Ile, Thr, Qln or His
<220> FEATURE:
<221> NAME/KEY: MISC_FEATURE
<222> LOCATION: (100)..(100)
<223> OTHER INFORMATION: Xaa may be Val, Thr, Ile, Tyr, Leu or Asp
<220> FEATURE:
<221> NAME/KEY: MISC_FEATURE
<222> LOCATION: (102)..(102)
<223> OTHER INFORMATION: Xaa may be Ser, Phe, Ala or Leu

<400> SEQUENCE: 76

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Xaa Ser
            20                  25                  30

Xaa Xaa Asn Xaa Asn Xaa Leu Ala Trp Tyr Gln Gln Lys Pro Gly Gln
        35                  40                  45

Pro Pro Lys Leu Leu Ile Tyr Xaa Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Xaa Xaa Xaa Xaa Pro Xaa Thr Phe Gly Gln Gly Thr Lys Val Glu Ile
            100                 105                 110

Lys
```

ANTI-CCL17 ANTIBODIES

CROSS REFERENCE TO RELATED APPLICATIONS

This is a divisional of application Ser. No. 14/534,525, filed Nov. 6, 2014, which claims the benefit of U.S. Provisional Application No. 61/900,596, filed Nov. 6, 2013. The contents of these applications are each incorporated herein by reference in their entirety.

This application claims the benefit of U.S. Provisional Application No. 61/900,596, filed Nov. 6, 2013, the entire contents of which are incorporated herein by reference.

FIELD OF THE INVENTION

The present invention relates to antibodies specifically binding CCL17, polynucleotides encoding the antibodies or fragments, and methods of making and using the foregoing.

BACKGROUND OF THE INVENTION

The homeostatic chemokine, CCL17 (TARC, chemokine (C-C motif) ligand 17) is a potent lymphocyte chemoattractant. CCL17 is a ligand for CCR4, a GPCR believed to be important in the function of T cells and chemotaxis and the migration of immune cells to sites of inflammation. CCR4 is predominantly expressed on Th2 lymphocytes, natural killer cells and iNKT cells.

CCL17 has been associated with human diseases affecting various organs such as ulcerative colitis (UC), atopic dermatitis (AD), idiopathic pulmonary fibrosis (IPF) and asthma (Belperio et al., *J Immunol*, 173: 4692-469, 2004; Christophi et al., *Inflamm Bowel Dis*. doi: 10.1002/ibd.2295; Inoue et al., *Eur Respir J*, 24: 49-56, 2004; Kakinuma et al., *J Allergy Clin Immunol*, 107: 535-541, 2001; Saeki and Tamaki, *J Dermatol Sci*, 43: 75-84, 2006; Tamaki et al., *J Dermatol*, 33: 300-302, 2006). In mice, CCL17 has been linked to various inflammatory conditions and infections such as chronic pulmonary inflammation present in models of fibrosis and asthma, colitis and schistosomiasis, presumably by inducing Th2 responses through recruitment of CCR4+ immune cells. Neutralization of CCL17 ameliorates the impacts of disease in both the *A. fumigatus* and ovalbumin (OVA) models of asthma, and liver damage in the *P. acnes* mouse model of induced hepatic injury by blocking influx of T cells (Carpenter and Hogamoam *Infect Immun*, 73:7198-7207, 2005; Heiseke et al., *Gastroenterology*, 142: 335-345; Hogamoam et al., *Med Mycol*, 43 Suppl 1, S197-202, 2005; Ismailoglu et al., Therapeutic targeting of CCL17 via the systemic administration of a monoclonal antibody ameliorates experimental fungal asthma. Paper presented at the *Am J Respir Crit Care Med*, 2011; Jakubzick et al., *Am J Pathol*, 165:1211-122, 2004; Kawasaki et al., *J Immunol*, 166:2055-2062, 2001; Yoneyama et al., *J Clin Invest*, 102: 1933-1941, 1998).

CCL22 (MDC) is a second ligand for CCR4. CCR4 interaction with each chemokine produces distinct outcomes (Allen et al., Annu Rev Immunol 25:787-820, 2007; Imai et al., J Biol Chem 273:1764-1768, 1998), possibly contributed by the differences in binding affinities of the two ligands for CCR4. CCL22 binds CCR4 with higher affinity and induces receptor internalization more readily than CCL17 (Baatar et al., *J Immunol* 179:1996-2004, 2007; Imai et al., *J Biol Chem* 273:1764-1768, 1998; Mariani et al., *Eur J Immunol* 34:231-240, 2004), and promotes cellular adhesion more readily than CCL17 (D'Ambrosio et al., *J Immunol* 169:2303-2312, 2002) CCL22 shows more restricted expression with production limited to immune cells, whereas CCL17 is expressed and secreted by many different cell types including non-immune cells (Alferink et al., *J Exp Med* 197:585-599, 2003; Berin et al., *Am J Respir Cell Mol Biol* 24:382-389, 2001; Godiska et al., *J Exp Med* 185:1595-1604, 1997; Imai et al., *J Biol Chem* 271:21514-21521, 1996; Saeki and Tamaki, *J Bermatol Sci* 43:75-84, 2006). In the murine ceacal ligation and puncture (CLP) model of experimental sepsis, CCL22 promoted innate immunity whereas CCL17 seemed to interfere and in some circumstances contribute to organ damage (Matsukawa et al., *Rev Immunogenet* 2:339-358, 2000). In the mouse model of pulmonary invasive aspergillosis, CCL22 played a protective role in the innate anti-fungal response whereas CCL17 played the role of suppressor (Carpenter and Hogaboam, *Infect Immun* 73:7198-7207, 2005). These two chemokines can play contrasting roles in establishing localized inflammation due to differential effects on Treg homeostasis in that Treg recruitment is favored by CCL22 but not CCL17 (Heiseke et al., *Gastroenterology* 142:335-345, 2011; Montane et al., *J Clin Invest*, 121:3024-30, 2011; Weber et al., *J Clin Invest* 121:2898-2910, 2011).

In animal model of contact hypersensitivity, CCL17 is a major factor in initiating the inflammatory response driving contact hypersensitivity (CBS) to challenge with either FITC or DNFB, and CCL17 knockout in these mice enhanced survival of cardiac allografts compared to heterozygous mice having one functional CCL17 allele (Alferink et al., *J Exp Med* 197:585-599, 2003).

CCR4 antagonists may be non-selective and inhibit both CCL17 and CCL22 functions. Therefore, there is a need for anti-CCL17 antibodies for the potential treatment of a variety of CCL17-mediated diseases including asthma.

SUMMARY OF THE INVENTION

One embodiment of the invention is an isolated antibody specifically binding human CCL17 comprising a heavy chain variable region (VH) and a light chain variable region (VL), wherein the antibody competes for binding to human CCL17 with an antibody comprising the VH of SEQ ID NO:45 and the VL of SEQ ID NO: 52.

Another embodiment of the invention is an isolated antibody specifically binding human CCL17 having the sequence of SEQ ID NO: 1, wherein the antibody binds human CCL17 at least within CCL17 amino acid residues 21-23, 44-45 and 60-68.

Another embodiment of the invention is an isolated antibody specifically binding human CCL17, wherein the antibody binds human CCL17 with an affinity constant ($K_D$) of about $1\times10^{-10}$ M or less, when the $K_D$ is measured using solution equilibrium affinity in tris-based saline buffer containing 0.05% Tween-20 after co-incubation of the antibody and human CCL17 for 48 hours at 4° C.

Another embodiment of the invention is an isolated antibody specifically binding human CCL17 comprising certain HCDR1, HCDR2, HCDR3, LCDR1, LCDR2 and LCDR3 sequences.

Another embodiment of the invention is an isolated antibody specifically binding human CCL17 comprising certain VH and VL sequences.

Another embodiment of the invention is an isolated antibody specifically binding human CCL17, wherein the antibody comprises the VH comprising the amino acid sequence at least 90%, 91%, 92%, 93%, 94%, 95%, 96%, 97%, 98% or 99% identical to the VH of SEQ ID NO: 46 and the VL comprising the amino acid sequence at least 90%, 91%, 92%, 93%, 94%, 95%, 96%, 97%, 98% or 99% identical to the VL of SEQ ID NO: 62.

Another embodiment of the invention is a pharmaceutical composition comprising the antibody of the invention and a pharmaceutically accepted carrier.

Another embodiment of the invention is an isolated polynucleotide encoding the VH or the VL of the invention.

Another embodiment of the invention is a vector comprising the polynucleotide of the invention.

Another embodiment of the invention is a host cell comprising the vector of the invention.

Another embodiment of the invention is a method of producing an antibody of the invention, comprising culturing the host cell of the invention in conditions that the antibody is produced.

Another embodiment of the invention is a method of treating a CCL17-mediated disease, comprising administering to a subject in need thereof the antibody of the invention for a time sufficient to treat the CCL17-mediated disease.

Another embodiment of the invention is a method of treating asthma or airway hyper-reactivity, comprising administering to a subject the antibody of the invention for a time sufficient to treat asthma.

BRIEF DESCRIPTION OF THE DRAWINGS

FIG. 3 shows the VH sequences of the anti-CCL17 antibodies binding to human CCL17 with a $K_D$ of 100 nM or lower. C17B234VH: SEQ ID NO: 45; C17B235VH: SEQ ID NO: 45; C17B236VH: SEQ ID NO: 45; C7B239VH: SEQ ID NO: 45; C7B240VH: SEQ ID NO: 45; C17B241V: SEQ ID NO: 45; C17B243VH: SEQ ID NO: 45; C17B244VH: SEQ ID NO: 45; C17B293VH: SEQ ID NO: 46; C17B294VH: SEQ ID NO: 47.

FIG. 4 shows the consensus VH and HCDR sequences of the anti-CCL17 antibodies shown in FIG. 3 that bind to human CCL17 with a KD of 100 nM or lower.

FIG. 5 shows the VL sequences of the anti-CCL17 antibodies binding to human CCL17 with a $K_D$ of 100 nM or lower. C17B234VL: SEQ ID NO: 50; C17B235VL: SEQ ID NO: 51; C17B236VL: SEQ ID NO: 52; C17B239VL: SEQ ID NO: 55; C17B240VL: SEQ ID NO: 56; C17B241VL: SEQ ID NO: 57; C17B243VL: SEQ ID NO: 59; C17B244VL: SEQ ID NO: 60; C17B293VL: SEQ ID NO: 62; C17B294VL: SEQ ID NO: 62.

FIG. 6A shows the consensus VL sequence of the anti-CCL17 antibodies shown in FIG. 5 that bind to human CCL17 with a $K_D$ of 100 nM or lower.

FIG. 6B shows the consensus LCDR sequences of the anti-CCL17 antibodies shown in FIG. 5 that bind to human CCL17 with a $K_D$ of 100 nM or lower.

DETAILED DESCRIPTION OF THE INVENTION

Figure 1A:
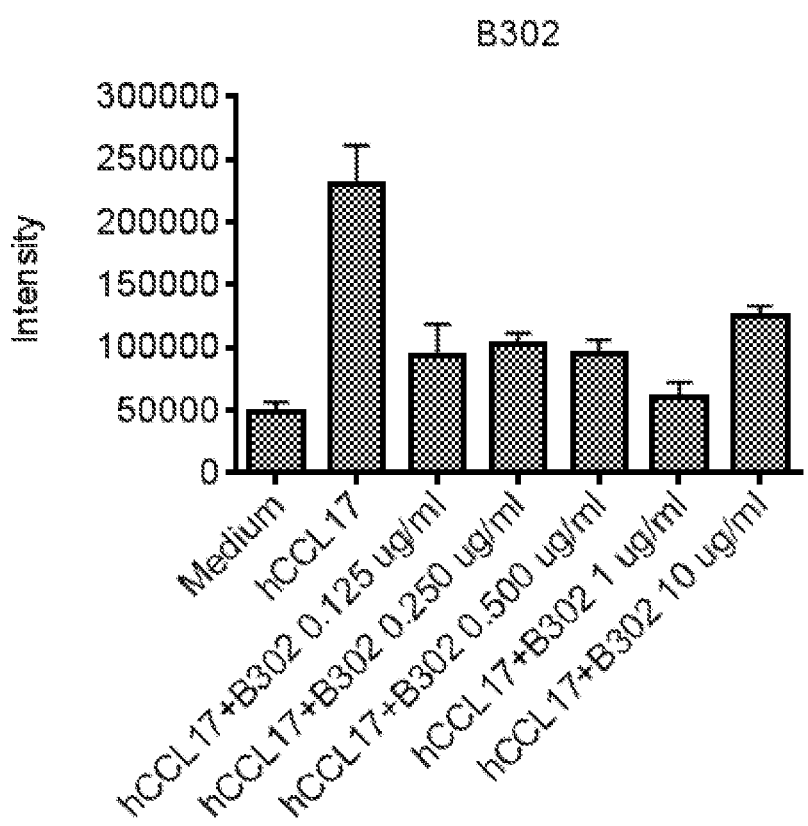
FIG. 1A shows inhibition of chemotaxis with anti-CCL17 antibody 8302 induced by 1 nM human CCL17 in CCRF-CEM cells. 8302 is C178302.
Figure 1B:
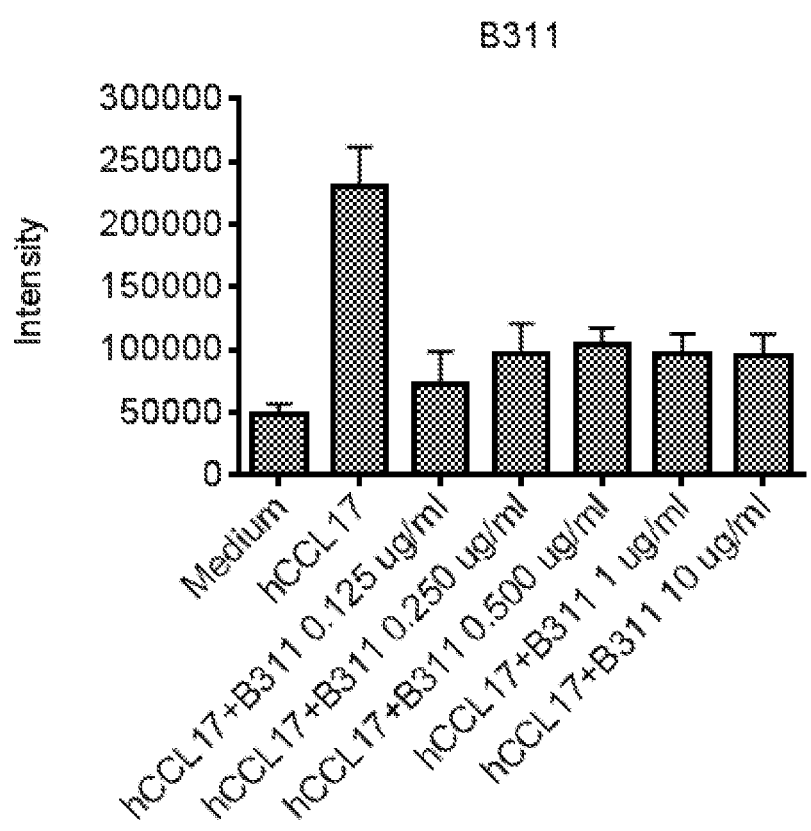
FIG. 1B shows inhibition of chemotaxis with anti-CCL17 antibody 8311 induced by 1 nM human CCL17 in CCRF-CEM cells. 8311 is C178311.
Figure 1C:
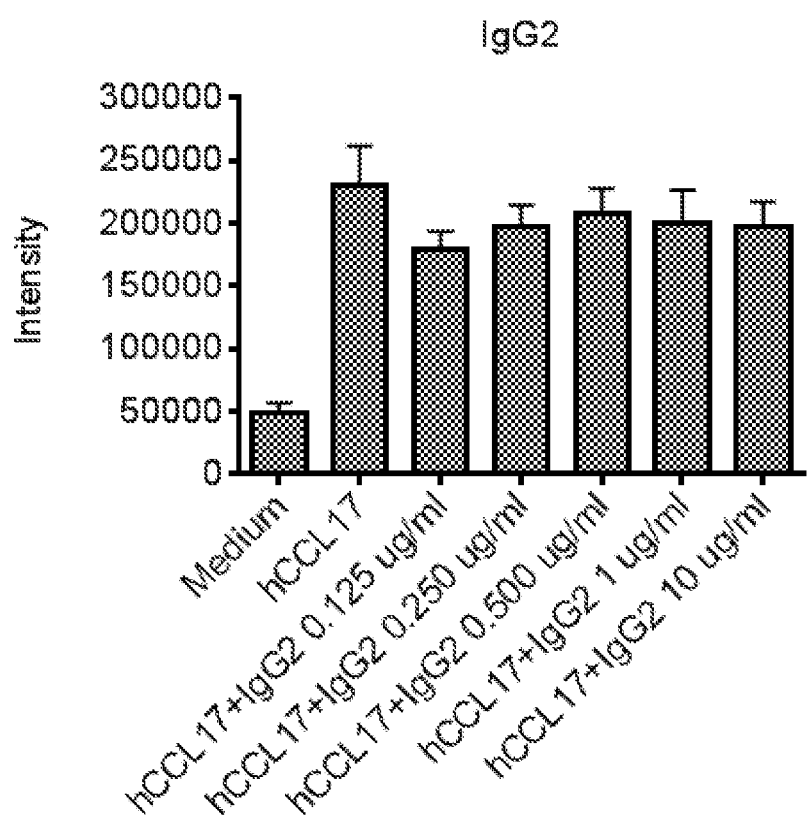
FIG. 1C shows effect of IgG2 isotype control on chemotaxis induced by 1 nM human CCL17 in CCRF-CEM cells.
Figure 1D:
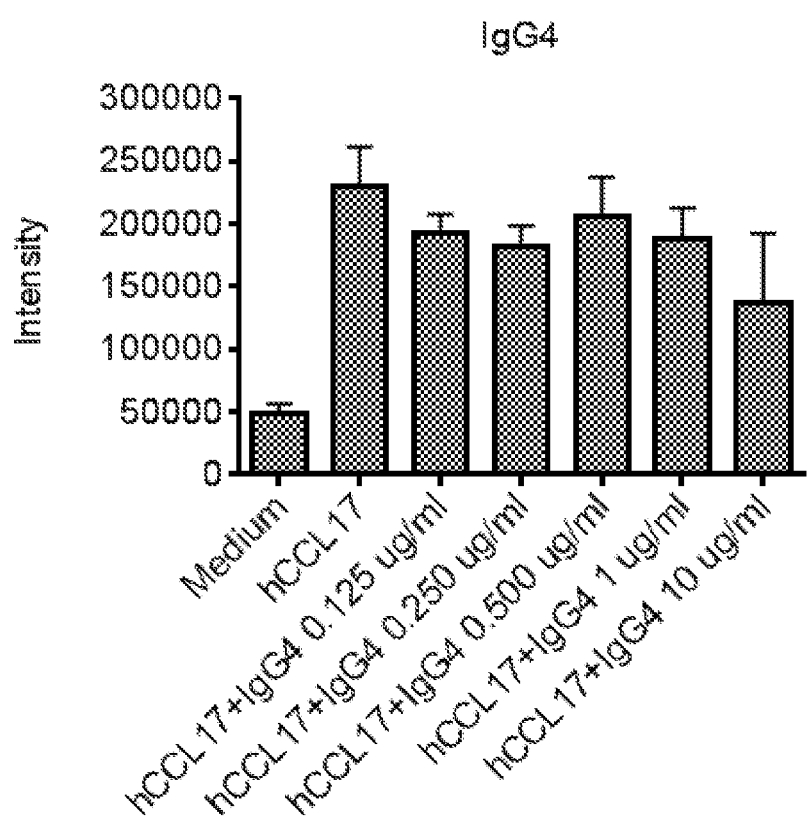
FIG. 1D shows effect of IgG4 isotype control on chemotaxis induced by 1 nM human CCL17 in CCRF-CEM cells.
Figure 2A:
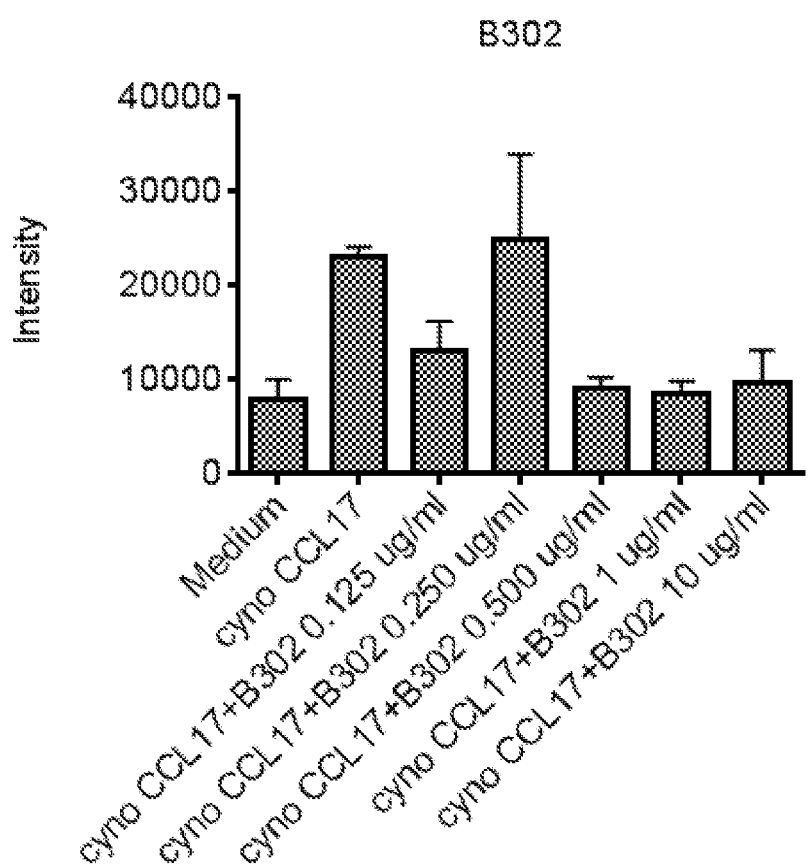
FIG. 2A shows inhibition of chemotaxis with anti-CCL17 antibody 8302 induced by 1 nM cyno CCL17 in HSC-F cells. 8302 is C178302.
Figure 2B:
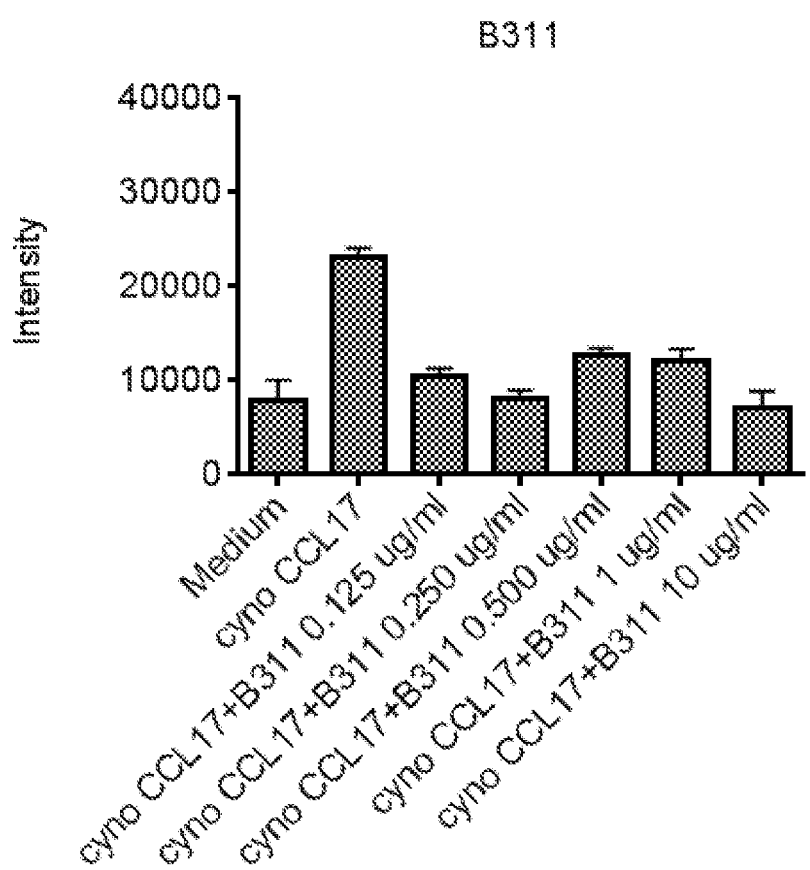
FIG. 2B shows inhibition of chemotaxis with anti-CCL17 antibody 8311 induced by 1 nM cyno CCL17 in HSC-F cells. 8311 is C178311.
Figure 2C:
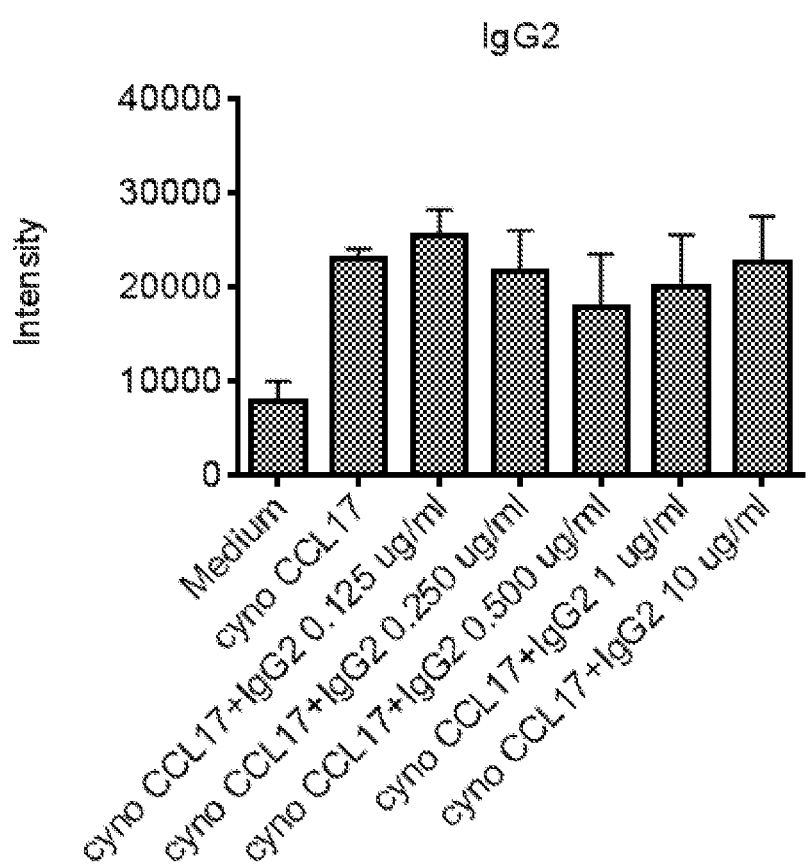
FIG. 2C shows effect of IgG2 isotype control on chemotaxis induced by 1 nM cyno CCL17 in HSC-F cells.
Figure 2D:
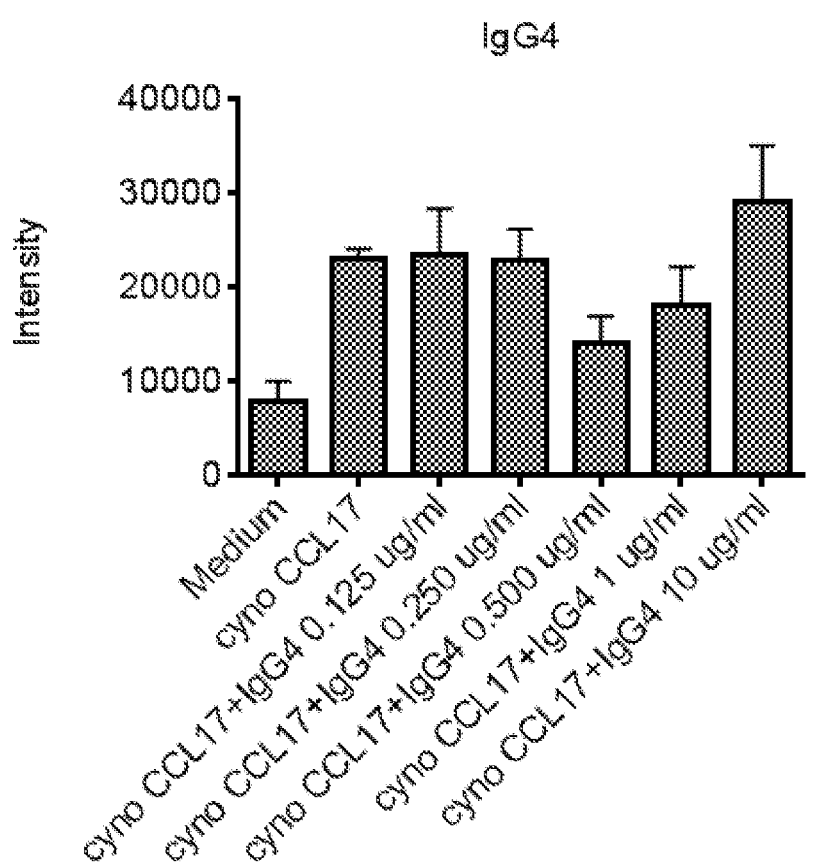
FIG. 2D shows effect of IgG4 isotype control on chemotaxis induced by 1 nM cyno CCL17 in HSC-F cells.

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein can be used in the practice for testing of the present invention, exemplary materials and methods are described herein. In describing and claiming the present invention, the following terminology will be used.

"Specific binding" or "specifically binds" or "binds" as used herein refers to antibody binding to a predetermined antigen with greater affinity than for other antigens. Typically, the antibody binds to a predetermined antigen with a dissociation constant ($K_D$) of about $1 \times 10^{-7}$ M or less, for example about $1 \times 10^{-8}$ M or less, about $1 \times 10^{-9}$ M or less, about $1 \times 10^{-10}$ M or less, about $1 \times 10^{-11}$ M or less, about $1 \times 10^{-12}$ M or less, about $1 \times 10^{-13}$ M or less or about $1 \times 10^{-14}$ M or less, typically with a $K_D$ that is at least ten fold less than its $K_D$ for binding to a non-specific antigen or epitope (e.g., BSA, casein). The dissociation constant can be measured using standard procedures. Antibodies that specifically bind to a predetermined antigen may, however, have cross-reactivity to other related antigens, for example to the same predetermined antigen from other species (homologs), such as human or monkey, for example *Macaca fascicularis* (cynomolgus, cyno) or Pan troglodytes (chimpanzee, chimp).

"Monoclonal antibody that specifically binds human CCL17" refers to antibodies that specifically bind human mature CCL17 having the sequence shown in SEQ ID NO: 1.

"Neutralizing" or "neutralizes" or "neutralizing antibody" or "antibody antagonist" as used herein refers to an antibody or antibody fragment that partially or completely inhibits, by any mechanism, CCL17 biological activity. Neutralizing antibodies can be identified using assays for CCL17 biological activity as described below. CCL7 neutralizing antibody may inhibit measured CCL17 biological activity by 20%, 30%, 40%, 50%, 60%, 70%, 75%, 80%, 85%, 90%, 95%, 96%, 97%, 98%, 99% or 100%.

"Human CCL17" or "huCCL17" as used interchangeably herein refers to the human CCL17 protein having the amino acid sequence shown in SEQ ID NO: 1. The sequence of the full length CCL17 including the signal sequence is available at Genbank; Accession Number NP_002978.

"Cyno CCL17" or "cCCL17" as used interchangeably herein refers to the *Macaca fascicularis* (cyno) CCL17 protein having the amino acid sequence shown in SEQ ID NO: 2.

"Antibodies" as used herein is meant in a broad sense and includes immunoglobin molecules including monoclonal antibodies including murine, human, humanized and chimeric antibodies, antibody fragments, bispecific or multispecific antibodies formed from at least two intact antibodies or antibody fragments, dimeric, tetrameric or multimeric antibodies, single chain antibodies, and any other modified configuration of the immunoglobulin molecule that comprises an antigen recognition site of the required specificity.

Immunoglobulins can be assigned to five major classes, namely IgA, IgD, IgE, IgG and IgM, depending on the heavy chain constant domain amino acid sequence. IgA and IgG are further sub-classified to $IgA_1$, $IgA_2$, $IgG_1$, $IgG_2$, $IgG_3$ and $IgG_4$ isotypes. Antibody light chains of any vertebrate species can be assigned to one of two clearly distinct types, namely kappa (κ) and lambda (λ), based on the amino acid sequences of their constant domains.

The term "antibody fragments" refers to a portion of an immunoglobulin molecule that retains the heavy chain ad/or the light chain antigen binding site, such as a heavy chain complementarity determining regions (HCDR) 1, 2 and 3, a light chain complementarity determining regions (LCDR) 1, 2 and 3, a heavy chain variable region (VH), or a light chain variable region (VL). Antibody fragments include a Fab fragment, a monovalent fragment consisting of the VL or the VH; a $F(ab)_2$ fragment, a bivalent fragment comprising two Fab fragments linked by a disulfide bridge at the hinge region; a Fd fragment consisting of the VH and CHI domains; a Fv fragment consisting of the VL and VH domains of a single arm of an antibody; a dAb fragment (Ward et al., *Nature* 341:544-546, 1989), which consists of a VH domain. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047. These antibody fragments are obtained using well known techniques and the fragments are characterized in the same manner as are intact antibodies.

The phrase "isolated antibody" refers to an antibody that is substantially free of other antibodies having different antigenic specificities (e.g., an isolated antibody specifically binding human CCL17 is substantially free of antibodies that specifically bind antigens other than human CCL17). An isolated antibody specifically binding human CCL17 may, however, have cross-reactivity to other antigens, such as orthologs of human CCL17, such as *Macaca fascicularis* (cynomolgus) CCL17. Moreover, an isolated antibody may be substantially free of other cellular material and/or chemicals.

An antibody variable region consists of a "framework" region interrupted by three "antigen binding sites". The antigen binding sites are defined using various terms: (i) Complementarity Determining Regions (CDRs), three in the V: (HCDR1, HCDR2, HCDR3) and three in the VL (LCDR1, LCDR2, LCDR3) are based on sequence variability (Wu and Kabat, *J Exp Med* 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk *Mol Biol* 196:901-17, 1987) Other terms include "IMGT-CDRs" (Lefranc et al., *Dev Comparat Immunol* 27:55-77, 2003) and "Specificity Determining Residue Usage" (SDRU) (Almagro *Mol Recognit*, 17:132-43, 2004). The International ImMunoGeneTics (IMGT) database provides a standardized numbering and definition of antigen-binding sites. The correspondence between CDRs, HVs and IMGT delineations is described in Lefranc et al., *Dev Comparat Immunol* 27:55-77, 2003.

"Chothia residues" as used herein are the antibody VL and VH residues numbered according to Al-Lazikani (Al-Lazikani et al., *J Mol Biol* 273:927-48, 1997).

"Framework" or "framework sequences" are the remaining sequences of a variable region other than those sequences defined to be antigen binding site. Because the antigen binding site can be defined by various terms as described above, the exact amino acid sequence of a framework depends on how the antigen-binding site was defined.

"Humanized antibody" refers to an antibody in which the antigen binding site is derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human antibody" refers to an antibody having heavy and light chain variable regions in which both the framework and the antigen binding site regions are derived from sequences of human origin. If the antibody contains a constant region, the constant region also is derived from sequences of human origin.

Human antibody comprises heavy or light chain variable regions that are "derived from" sequences of human origin if the variable regions of the antibody are obtained from a system that uses human germline immunoglobulin or rearranged immunoglobulin genes. Such systems include human immunoglobulin gene libraries, for example libraries displayed on phage, and transgenic non-human animals such as mice carrying human immunoglobulin loci as described herein. "Human antibody" may contain amino acid differences when compared to the human germline or rearranged immunoglobulin sequences due to for example naturally occurring somatic mutations or intentional introduction or substitutions. Typically, "human antibody" is at least about 80%, 85%, 901, 95%, 96%, 97%, 98%, 99% or 100% identical in amino acid sequence to an amino acid sequence encoded by a human germline or rearranged immunoglobulin gene. In some cases, "human antibody" may contain consensus framework sequences derived from human framework sequence analyses, for example as described in Knappik et al., *J Mol Biol* 296:57-66, 2000), or synthetic HCDR3 incorporated into human immunoglobulin gene libraries displayed on phage, for example as described in Shi et al., *J Mol Biol* 397:365-96, 2010 and Int. Pat. Publ. No. WO2009/08546).

Isolated humanized antibodies may be synthetic. Human antibodies, while derived from human immunoglobulin sequences, can be generated using systems such as phage display incorporating synthetic CDRs and/or synthetic frameworks, or can be subjected to in vitro mutagenesis to improve antibody properties, resulting m antibodies that do not naturally exist within the human antibody germline repertoire in vivo.

Human antibodies may include substitutions in the framework or in the antigen binding site so that they may not be exact copies of expressed human immunoglobulin or germline gene sequences. However, antibodies in which antigen binding sites are derived from a non-human species are not included in the definition of "human antibody".

The term "recombinant antibody" as used herein, includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom (described further below), antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences.

The term "monoclonal antibody" as used herein refers to a preparation of antibody molecules of single molecular composition.

The term "substantially identical" as used herein means that the two antibody variable region amino acid sequences being compared are identical or have "insubstantial differences". Insubstantial differences are substitutions of 1, 2, 3, 4, 5, 6, 7, 8, 9, 1.0, 1.1, 1.2, 1.3, 14, or 15 amino acids in an antibody variable region sequence that do not adversely affect antibody properties. Amino acid sequences substantially identical to the variable region sequences disclosed herein are within the scope of the invention. In some embodiments, the sequence identity can be about 907, 91%, 927, 937, 947, 95%, 967, 977, 987, 997 or higher. Percent identity can be determined for example by pairwise alignment using the default settings of the AlignX module of Vector NTI v.9.0.0 (Invitrogen, Carlsbad, Calif.). The protein sequences of the present invention can be used as a query sequence to perform a search against public or patent-databases to, for example, identify related sequences. Exemplary programs used to perform such searches are the XBLAST or BLASTP programs, or the GenomeQuest™ (GenomeQuest, Westborough, Mass.) suite using the default settings.

The term "epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Bispecific" as used herein refers to an antibody or molecule that binds two distinct antigens or two distinct epitopes within an antigen.

"Monospecific" as used herein refers to an antibody that binds one antigen or one epitope.

The term "in combination with" as used herein means that the described agents can be administered to an animal together in a mixture, concurrently as single agents or sequentially as single agents in any order.

The term "vector" means a non-natural polynucleotide capable of being duplicated within a biological system or that can be moved between such systems. Vector polynucleotides typically contain a cDNA encoding a protein of interest and additional elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DMA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

"Complementary DNA" or "cDNA" refers to a well known synthetic polynucleotide that shares the arrangement of sequence elements round in native mature mRNA species with contiguous exons, with the intervening introns present in genomic DNA are removed. The codons encoding the initiator methionine may or may not be present in cDNA. cDNA may be synthesized for example by reverse transcription or synthetic gene assembly.

"Synthetic" or "non-natural" as used herein refers to a polynucleotide or a polypeptide molecule not present in nature.

The term "polypeptide" or "protein" means a molecule that comprises at least two amino acid residues linked by a peptide bond to form a polypeptide. Small polypeptides of less than 50 amino acids may be referred to as "peptides".

Conventional one and three-letter amino acid codes are used herein as shown in Table 1.

TABLE 1

| Amino Acid | Three-letter code | One-letter code |
| --- | --- | --- |
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | p |
| Serine | Ser | s |
| Threonine | Thr | T |
| Tryptophan | Trp | w |
| Tyrosine | Tyr | y |
| Valine | Val | V |

Compositions of Matter

The present invention provides monoclonal antibodies specifically binding human CCL17. The antibodies of the invention inhibit CCL17 biological activity in the cell, and may optionally cross-react with cyno CCL17. The present invention provides synthetic polynucleotides encoding the antibodies and fragments thereof, vectors and host cells, and methods of making and using the antibodies of the invention.

One embodiment of the invention is an isolated antibody specifically binding human CCL17.

Another embodiment of the invention is an isolated antibody specifically binding human CCL17 comprising a heavy chain variable region (VH) and a light chain variable region (VL), wherein the antibody competes for binding to human CCL17 with an antibody comprising the VH of SEQ ID NO:45 and the VL of SEQ ID NO: 52. The antibody comprising the VH of SEQ ID NO: 46 and the VL of SEQ ID NO: 62 is expected to compete for binding to human CCL17 with the antibody comprising the VH of SEQ ID NO: 45 and the VL of SEQ ID NO: 52.

Competition between specific binding to human CCL17 with antibodies of the invention comprising certain VH and VL amino acid sequences can be assayed in vitro using well known methods. For example, binding of MSD Sulfa-Tag™ NBS-ester-labeled antibody to human CCL17 in the presence of an unlabeled antibody can be assessed by ELISA, or Biacore analyses or flow cytometry may be used to demonstrate competition with the antibodies of the current invention. The ability of a test antibody to inhibit the binding of the antibody comprising the VH of SEQ ID NO: 45 and the VL of SEQ ID NO: 52 to human CCL17 demonstrates that the test antibody can compete with these antibodies for binding to human CCL17.

Another embodiment of the invention is an isolated antibody specifically binding human CCL17 having the sequence of SEQ ID NO: 1, wherein the antibody binds human CCL17 at least within CCL17 amino acid residues 21-23, 44-45 and 60-68. "At least within human CCL17 amino acid residues 21-23, 44-45 and 60-68" means that the anti-CCL17 antibody binds at least one residue residing within the amino acid stretch of residues 21-23 of SEQ ID NO: 1, and at least one residue residing within the amino acid stretch of residues 44-45 of SEQ ID NO: 1, and at least one residue residing within the amino acid stretch of residues 60-68 of SEQ ID NO: 1. The antibody may bind more than one residue within the residues 21-23, 44-45 and 60-68, and additional residues outside of residues 21-23, 44-45 and 60-68 of SEQ ID NO: 1.

In some embodiments, the antibody binds human CCL17 at least at residues R22 and K23 of SEQ ID NO: 1.

In some embodiments, the antibody binds human CCL17 at least at residues L21, R22, K23, V44, Q45, N60, Y64, S67 and L68 of SEQ ID NO: 1.

An exemplary antibody that binds human CCL17 within CCL17 amino acid residues 21-23, 44-45 and 60-68 of SEQ ID NO: 1 is C17B236 having VH of SEQ ID NO: 45 and VL of SEQ ID NO: 52. Based on crystal structure analyses, the main epitope residues bound by C17B236 are R22 and K23 of CCL17 of SEQ ID NO: 1, based on the number of contacts between these residues and the antibody VH residues.

Other exemplary antibodies that bind human CCL17 within CCL17 amino acid residues 21-23, 44-45 and 60-68 are variants of C17B236, which are derived from an affinity-maturation campaign of the same parental antibody. The VH and the VL sequences of the exemplary antibodies are shown in FIG. 3 and FIG. 5. The antibody comprising the VH of SEQ ID NO: 46 and the VL of SEQ ID NO: 62 is expected to bind to human CCL17 within CCL17 amino acid residues 21-23, 44-45 and 60-68.

Affinity maturation of antibodies typically involves amino acid substitutions in the CDRs or in the Vernier zone (framework regions that underline the CDRs). The matured variants are selected by panning the combinatorial libraries, which may contain up to $10^8$ mutants. The cap on the size of the library limits the number of variable positions to 6-7 if all 20 amino acids are allowed in each position. The majority of the paratope residues are preserved in each combinatorial library, which ensures that the binding epitope is also preserved. Several crystallographic studies of the parent and matured antibodies have shown that the epitope is always preserved during affinity maturation (e.g. Fransson et al., J. Mol. Biol. 2010, 398:214-231; Gustchina et al., PLoS Pathog. 2010, 6:e1001182; La Porte et al., MAbs 2014; 6:1059-1068).

Anti-CCL17 antibodies that bind human CCL17 within CCL17 amino acid residues 21-23, 44-45 and 60-68 bind human CCL17 with high affinity, typically with the $K_D$ less than about $1 \times 10^{-10}$ M.

Antibodies that bind human CCL17 within CCL17 amino acid residues 21-23, 44-45 and 60-68 may be made for example by immunizing mice with CCL17 chimeric protein that has human CCL17 sequences at residue positions 21-23, 44-45 and 60-68, or panning phage display libraries with wild type human CCL17, and cross-screening the resulting hits with CCL17 variants that have substitutions at each or several residue positions within the residues 21-23, 44-45 and 60-68 of human CCL17 using methods described herein.

In some embodiments of the invention, the antibody specifically binding human CCL17 blocks CCL17/CCR4 interaction.

Antibodies can be tested for their ability to block CCL17/CCR4 interaction by standard flow cytometry. For example, cells expressing CCR4 are incubated with fluorescently labeled human CCL17 and the test antibody, after which the binding of the fluorescently labeled human CCL17 onto CCR4-expressing cells is assessed using standard methods. Antibodies that "block CCL17/CCR4 interaction" or "inhibit CCL17/CCR4 interaction" may inhibit binding of CCL17 to CCR4-expressing cells by 30%, 40%, 50%, 60%, 70%, 75%, 80%, 85%, 90%, 95%, 96%, 97%, 98%, 99% or 100% when compared to binding of CCL17 in the absence of the antibody.

Another embodiment of the invention is an isolated antibody specifically binding human CCL17, wherein the antibody binds human CCL17 with an affinity constant ($K_D$) of about $1 \times 10^{-7}$ M or less, of about $1 \times 10^{-8}$ M or less, about $1 \times 10^{-9}$ M or less, about $1 \times 10^{-10}$ M or less, about $1 \times 10^{-11}$ M or less, about $1 \times 10^{-12}$ M or less, about $1 \times 10^{-13}$ M or less, or about $1 \times 10^{-14}$ M or less, when the $K_D$ is measured using solution equilibrium affinity in tris-based saline buffer containing 0.05% Tween-20 after co-incubation of the antibody and human CCL17 for 48 hours at 4° C.

In some embodiments, the antibody binds human CCL17 with an affinity constant ($K_D$) of about $1 \times 10^{-10}$ M or less, when the $K_D$ is measured using solution equilibrium affinity in tris-based saline buffer containing 0.05% Tween-20 after co-incubation of the antibody and human CCL17 for 48 hours at 4° C.

In some embodiments, the antibody binds human CCL17 with the $K_D$ of about $5 \times 10^{-12}$ M or less.

In another embodiment, the antibody of the invention specifically binding human CCL17 binds *Macaca fascicularis* (cyno) CCL17 with an affinity constant ($K_D$) of about $1 \times 10^{-6}$ M or less, about $1 \times 10^{-7}$ M or less, about $1 \times 10^{-8}$ M or less, about $1 \times 10^{-9}$ M or less, about $1 \times 10^{-10}$ M or less, about $1\times10^{-11}$ M or less or about $1\times10^{-12}$ M or less, when the $K_D$ is measured using solution equilibrium affinity in tris-based saline buffer containing 0.05% Tween-20 after co-incubation of the antibody and cyno CCL17 for 48 hours at 4° C.

In some embodiments, the antibody of the invention binds *Macaca fascicularis* (cyno) CCL17 with the $K_D$ of about $1\times10^{-9}$ M or less, when the $K_D$ IS measured using solution equilibrium affinity in tris-based saline buffer containing 0.05?; Tween-20 after co-incubation of the antibody and cyno CCL17 for 48 hours at 4° C. The affinity of an antibody to human CCL17 having the sequence of SEQ ID NO: 1 or cyno CCL17 having the sequence of SEQ ID NO: 2 can be measured experimentally using any suitable method. Such methods may utilize Froteon, Biacore or KinExA instrumentation, such as ProteOn XPR36 or Biacore 3000, solution equilibrium affinity (SEA), ELISA or competitive binding assays known to those skilled in the art. Exemplary methods are those described in Example 3. The measured affinity of a particular antibody/CCL17 interaction can vary if measured under different conditions (e.g., osmolarity, pH, buffer, detergent concentration). Thus, measurements of affinity and other binding parameters (e.g., $K_D$, $K_{on}$, $K_{off}$) are preferably made with standardized conditions and a standardized buffer, such as the buffer described herein. Skilled in the art will appreciate that the internal error for affinity measurements for example using solution equilibrium affinity, Biacore 3000 or ProteOn (measured as standard deviation, 3D) can typically be within 5-33% for measurements within the typical limits of detection. Therefore the term "about" reflects the typical standard deviation in the assay. For example, the typical SD for a $K_D$ of $1\times10^{-9}$ M is up to $\pm0.33\times10^{-9}$M.

Another embodiment of the invention is an isolated antibody specifically binding human CCL17, wherein the antibody inhibits CCL17 biological activity.

"CCL17 biological activity" as used herein refers to any activity occurring as a result of CCL17 binding to its receptor CCR4. An exemplary CCL17 biological activity results in intracellular calcium mobilization or chemotaxis of cells, for example CCRF-CEM cells (T lymophblastoid cell line from patient with acute leukemia). The antibodies of the invention can be tested for their ability to inhibit CCL17 biological activity using standard methods and those described herein. For example, ability of the antibodies of the invention to inhibit CCL17-dependent intracellular calcium mobilization can be assayed by measuring effect of the antibodies on CCL17-induced calcium mobilization using fluorescent dyes such as Flue-3 NW, Fluo-4 AM or Fluo-3 AM. Ability of the antibodies of the invention to inhibit CCL17-induced chemotaxis can be measured by measuring migration of CCRF-CEM cells through a semipermeable 5 µM filter in a two-chamber culture system, and measuring viability of cells migrated through the filter, The antibodies of the invention may inhibit CCL17 biological activity by about 207, 30%, 40%, 50%, 60%, 70%, 75%, 80%, 35%, 90%, 91%, 92%, 93%, 94%, 95%, 96%, 97%, 98%, 99% or 100%.

Another embodiment of the invention is an antibody specifically binding CCL17, wherein the antibody inhibits 10 ng/ml human CCL11-induced calcium mobilization in CCRF-CEM cells measured using Fluo-8 NW with an $IC_{50}$ value of about: $1\times10^{-7}$ M of less, about $1\times10^{-8}$M or less, or about $1\times10^{-9}$ M or less.

Another embodiment of the invention is an antibody specifically binding CCL17, wherein the antibody comprises heavy chain complementarity determining regions (HCDR) 1 (HCDR1), 2 (HCDR2) and 3 (HCDR3) and light chain complementarity determining regions (LCDR) 1 (LCDR1), 2 (LCDR2) and 3 (LCDR3), wherein the HCDR1, the HCDR2, the HCDR3, the LCDR1, the LCDR2 and the LCDR3 comprise the amino acid sequences of SEQ ID NOs: 4, 5, 71, 72, 73 and 74, respectively.

Antibodies comprising the HCDR and the LCDR sequences of SEQ ID NOs: 4, 5, 71, 72, 73 and 74 bind human CCL17 with a $K_D$ of $1\times10^{-10}$ or less.

```
HCDR1:
                                           (SEQ ID NO: 4)
SYWIG

HCDR2:
                                           (SEQ ID NO: 5)
IIDPSDSDTRYSPSFQG

HCDR3 consensus sequence
                                           (SEQ ID NO: 71)
VGPADVWDX1FDY,
wherein
X1 is s, A or T X2 is F, P, H or I;

X3 is D, Y, W, T or V;

X4 is I, F, S, T, Y, N, K or V;

and

X5 is K, A, Q, T or D.

LCDR2 consensus sequence:
                                           (SEQ ID NO: 73)
X1ASTRE,
wherein
X1 is N, H, G, E, T or D.

LCDR3 consensus sequence
                                           (SEQ ID NO: 74)
QQX1X2X3X4PXsT;

wherein

X1 is F, Y, T or H;

X2 is Y, L, N or W;

X3 is S, A, L, I, T, Q or H;

X4 is V, T, I, Y, L or D;
and

X5 is S, F, A or L.
```

In some embodiment, the HCDR1 comprises the sequence of SEQ ID NO: 4, the HCDR2 comprises the sequence of SEQ ID NO: 5 and the HCDR3 comprises the sequence of SEQ ID NOs: 6, 42, 43 or 44 in the antibody of the invention specifically binding CCL17.

In some embodiments, the HCDR1 comprises the amino acid sequence of SEQ ID NO: 4, the HCDR2 comprises the amino acid sequence of SEQ ID NO: 5 and the HCDR3 comprises the amino acid sequence of SEQ ID NOs: 6, 42 or 43.

In some embodiments, the LCDR1 comprises the sequence of SEQ ID NOs: 7, 8, 9, 10, 11, 12, 13, 14, 15, 16, 17 or 18; the LCDR2 comprises the sequence of SEQ ID NOs: 19, 20, 21, 22, 23, 24, 25, 26, 39, 40 or 41; and the LCDR3 comprises the sequence of SEQ ID NOs: 27, 26, 29, 30, 31, 32, 33, 34, 35, 36, 37 or 38 in the antibody of the invention specifically binding CCL17.

In some embodiments, the LCDR1 comprises the amino acid sequence of SEQ ID NOs: 8, 9, 10, 13, 14, 15, 17 or 18, the LCDR2 comprises the amino acid sequence of SEQ ID NOs: 20, 21, 22, 24, 25 and 26 and the LCDR3 comprises the amino acid sequence of SEQ ID NOs: 28, 29, 30, 33, 34, 35, 37 or 38.

In some embodiments, the antibody specifically binding CCL17 comprises the VH of SEQ ID NO: 75 and the VL of SEQ ID NO: 76.

```
VH consensus sequence
                                              (SEQ ID NO: 75)
EVQLVQSGAEVKKPGESLKISCKGSGYSFTSYWIGWVRQMPGKGLEWMGI

IDPSDSDTRYSPSFQGQVTISADKSISTAYLQWSSLKASDTAMYYCARVG

PADVWDX1FDYWGQGTLVTVSS wherein

X₁ is S, A or T.

VL consensus sequence (SEQ ID NO: 76):
DIVMTQSPDSLAVSLGERATINCKSSQSVLX1SX2X3NX4NX5LAWYQQKP

GQPPKLLIYX6ASTRESGVPDRFSGSGSGTDFTLTISSLQAEDVAVYYC

QQX7X8X9X10PX11TFGQGTKVEIK;

wherein

X₁ is L, Y, S or N;

X₂ is F, P, H or I;

X₃ is D, Y, W, T or V;

X₄ is I, F, S, T, Y, N, K or V;

X₅ is K, A, Q, T or D;

X₆ is N, H, G, E, T or D;

X₇ is F, Y, T or H;

X₈ is Y, L, N or W;

X₉ is S, A, L, I, T, Q or H;

X₁₀ is V, T, I, Y, L or D;
and

X₁₁ is S, F, A or L.
```

In some embodiments, the antibody specifically binding CCL17 comprises the VH of SEQ ID NOs: 45, 46, 47 or 48.

In some embodiments, the antibody specifically binding CCL17 comprises the VL of SEQ ID NOs: 49, 50, 51, 52, 53, 54, 55, 56, 57, 58, 59, 60, 61, 62, 63, 64, 65 or 66.

In some embodiments, the antibody specifically binding CCL17 comprises the VH comprises the amino acid sequence of SEQ ID NOs: 45, 46 or 47.

In some embodiments, the antibody specifically binding CCL17 comprises the VL comprises the amino acid sequence of SEQ ID NOs: 50, 51, 52, 55, 56, 57, 59, 60 or 62.

Another embodiment of the invention is an isolated antibody specifically binding CCL17, wherein the antibody comprises the HCDR1, HCDR2, HCDR3, LCDR1, LCDR2 and LCDR3 sequences of SEQ ID NOs: A, 5, 6, 7, 19 and 27, respectively;
SEQ ID NOs: A, 5, 6, 8, 20 and 28, respectively;
SEQ ID NOs: 4, 5, 6, 9, 21 and 29, respectively;
SEQ ID NOs: 4, 5, 6, 10, 22 and 30, respectively;
SEQ ID NOs: 4, 5, 6, 11, 23 and 31, respectively;
SEQ ID NOs: 4, 5, 6, 12, 24 and 32, respectively;
SEQ ID NOs: 4, 5, 6, 13, 21 and 33, respectively;
SEQ ID NOs: 4, 5, 6, 14, 20 and 34, respectively;
SEQ ID NOs: 4, 5, 6, 15, 25 and 35, respectively;
SEQ ID NOs: 4, 5, 6, 16, 21 and 36, respectively;
SEQ ID NOs: 4, 5, 6, 17, 25 and 37, respectively;
SEQ ID NOs: 4, 5, 6, 18, 26 and 38, respectively;
SEQ ID NOs: 4, 5, 6, 8, 39 and 28, respectively;
SEQ ID NOs: 4, 5, 6, 8, 24 and 28, respectively;
SEQ ID NOs: 4, 5, 6, 8, 22 and 28, respectively;
SEQ ID NOs: 4, 5, 6, 8, 40 and 28, respectively;
SEQ ID NOs: 4, 5, 6, 8, 26 and 28, respectively;
SEQ ID NOs: 4, 5, 6, 8, 41 and 28, respectively;
SEQ ID NOs: 4, 5, 42, 8, 24 and 28, respectively;
SEQ ID NOs: 4, 5, 43, 8, 24 and 28, respectively; or
SEQ ID NOs: 4, 5, 44, 6, 24 and 28, respectively.

Another embodiment of the invention is an isolated antibody specifically binding CCL17, wherein the antibody comprises the VH of SEQ ID NO: 45 and the VL of SEQ ID NOs: 49, 50, 51, 52, 53, 54, 55, 56, 57, 58, 58, 59, 60, 61, 62, 63, 64, 65 or 66;

the VH and the VL of SEQ ID NOs: 46 and 62, respectively;

the VH and the VL of SEQ ID NOs: 47 and 62, respectively; or the VH and the VL of SEQ ID NOs: 48 and 62, respectively.

Another embodiment of the invention is an isolated antibody specifically binding CCL17, wherein the antibody comprises
- the VH of SEQ ID NO: 45 and the VL of SEQ ID NOs: 50, 51, 52, 55, 56, 57, 59 or 60;
- the VH and the VL of SEQ ID NOs: 46 and 62, respectively; or
- the VH and the VL of SEQ ID NOs: 47 and 62, respectively.

Another embodiment of the invention is an isolated antibody specifically binding CCL17, wherein the antibody comprises the VH comprising the amino acid sequence at least 90%, 91%, 92%, 93%, 94%, 95%, 96%, 97%, 98% or 99% identical to the VH of SEQ ID NO: 46 and the VL comprising the amino acid sequence at least 90%, 91%, 92%, 93%, 94%, 95%, 96%, 97%, 98% or 99% identical to the VL of SEQ ID NO: 62.

Such exemplary antibodies are antibodies shown m Table 9.

Antibodies whose heavy chain CDR, light chain CDR, VH or VL amino acid sequences differ insubstantially from those shown in Tables 3, 4, 6, 7 and 9 are encompassed within the scope of the invention. Typically, this involves one or more conservative amino acid substitutions with an amino acid having similar charge, hydrophobic, or stereo chemical characteristics in the antigen-binding site or in the framework without adversely altering the properties of the antibody. Conservative substitutions may also be made to improve antibody properties, for example stability or affinity. 1, 2, 3, 4, 5, 6, 7, 8, 9, 10, 11, 12, 13, 14, or 15 amino acid substitutions can be made to the VH or VL sequence. For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for alanine scanning mutagenesis (MacLennan et al (1998) *Act Physiol. Scand. Suppl.* 643:55-67; Sasaki et al (1998) *Adv. Biopsy's.* 35:1-24). Desired amino acid substitutions can be determined by those skilled in the art at the time such substitutions are desired. For example, amino acid substitutions can be used to identify important residues of the molecule sequence, or to increase or decrease the affinity of the molecules described herein. The following eight groups contain amino acids that are conservative amino acid substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (Si, Threonine (T); and 8) Cysteine (C), Methionine (M) (see, e.g., Creighton, Proteins (1984)).

Amino acid substitutions can be done for example by PCR mutagenesis (U.S. Pat. No. 4,683,195). Libraries of variants can be generated using well known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties.

Although the embodiments illustrated in the Examples comprise pairs of variable regions, one from a heavy chain and one from a light chain, a skilled artisan will recognize that alternative embodiments may comprise single heavy or light chain variable regions. The single variable region can be used to screen for variable domains capable of forming a two-domain specific antigen-binding fragment capable of, for example, binding to human CCL17 having the sequence of SEQ ID NO: 1. The screening may be accomplished by phage display screening methods using for example hierarchical dual combinatorial approach disclosed in Int. Pat. Publ. No. WO1992/01047. In this approach, an individual colony containing either a H or L chain clone is used to infect a complete library of clones encoding the other chain (L or H), and the resulting two-chain specific antigen-binding domain is selected in accordance with phage display techniques as described. Therefore, the individual VH and VL polypeptide chains are useful in identifying additional antibodies specifically binding human CCL17 having the sequence of SEQ ID NO: 1 using the methods disclosed in Int. Pat. Publ. No. WO1992/01047.

Antibodies of the invention may be made using a variety of technologies for generating monoclonal antibodies. For example, the hybridoma method of Kohler and Milstein, Nature 256:495, 1975 can be used. In the hybridoma method, a mouse or other host animal, such as a hamster, rat or monkey, is immunized with human CCL17 and/or cyno CCL17 protein or fragments of these proteins, such as an extracellular portion of human CCL17, followed by fusion of spleen cells from immunized animals with myeloma cells using standard methods to form hybridoma cells (Gooding, Monoclonal Antibodies: Principles and Practice, pp. 59-103 (Academic Press, 1986)). Colonies arising from single immortalized hybridoma cells are screened for production of antibodies with desired properties, such as specificity of binding, cross-reactivity or lack thereof, and affinity for the antigen.

Various host animals can be used to produce antibodies against human CCL17. For example, Balb/c mice may be used to generate mouse anti-human CCL17 antibodies. The antibodies made in Blab/c mice and other non-human animals can be humanized using various technologies to generate more human-like sequences. Exemplary humanization techniques including selection of human acceptor frameworks are known to skilled m the art and include CDR grafting (U.S. Pat. No. 5,225,539), SDR grafting (U.S. Pat. No. 6,818,749), Resurfacing (Palin, *Mol Immunol* 28: 489-499, 1991), Specificity Determining Residues Resurfacing (U.S. Pat. Publ. No. 2010/0261620), human-adaptation (or human framework adaptation) (U.S. Pat. Publ. No. US2009/0118127), Super humanization (U.S. Pat. No. 7,709,226) and guided selection (Osborn et al., *Methods* 36:61-68, 2005; U.S. Pat. No. 5,565,332).

Humanized antibodies can be further optimized to improve their selectivity or affinity to a desired antigen by incorporating altered framework support residues to preserve binding affinity (back mutations) by techniques such as those disclosed as described in Int. Pat. Publ. No. WO1990/007861 and in Int. Pat. Publ. No. WO1992/22653.

Transgenic mice carrying human immunoglobulin loci m their genome can be used to generate human antibodies against a target protein, and are described in for example int. Pat. Publ. No. WO1990/04036, U.S. Pat. No. 6,150,584, Int. Pat. Publ. No. WO1999/45962, Int. Pat. Publ. No. WO2002/066630, Int. Pat. Publ. No. WO2002/43478, Loner et al., *Nature* 368:856-9, 1994; Green et al., *Nature Genet.* 7:13-21, 1994; Green & Jakobovits *Exp Med* 188:483-95, 1998; Lonberg and Huszar *Int Rev Immunol* 13:65-93, 1995; Bruggemann et al., *Eur J Immunol* 21:1323-1326, 1991; Fishwild et al., *Nat Biotechnol* 14:845-851, 1996; Mendez et al., *Nat Genet* 15: 146-156, 1997; Green, *J Immunol Methods* 231:11-23, 1999; Yang et al., *Cancer Res* 59:1236-1243, 1999; Brüggemann and Taussig *Curr Opin Biotechnol* 8:455-458, 1997; Int. Pat. Publ. No. WO2002/043476). The endogenous immunoglobulin loci in such mice may be disrupted or deleted, and at least one complete or partial human immunoglobulin locus may be inserted into the mouse genome using homologous or non-homologous recombination, using transchromosomes, or using minigenes. Companies such as Regeneron, Harbour Antibodies, Open Monoclonal Technology, Inc. (OMT), KyMab, Trianni and Ablexis can be engaged to provide human antibodies directed against a selected antigen using technology as described above.

Human antibodies can be selected from a phage display library, where the phage is engineered to express human immunoglobulins or portions thereof such as Fans, single chain antibodies (scFv), or unpaired or paired antibody variable regions (Knappik et al., *J Mol Biol* 296:57-86, 2000; Krebs et al., *J Immunol Meth* 254:67-84, 2001; Vaughan et al., *Nature Biotechnology* 14:309-314, 1996; Sheets et al., *PITAS* (USA) 95:6157-6162, 1998; Hoogenboom and Winter, *J Mol Biol* 227:381, 1991; Marks et al., *J Mol Biol* 222:581, 1991). The antibodies of the invention may be isolated for example from phage display library expressing antibody heavy and light, chain variable regions as fusion proteins with bacteriophage pIX coat protein as described in Shi et al., *J Mol Biol* 397:385-96, 2010 and Int. Pat. Publ. No. WO2009/085462). The antibody libraries are screened for binding to human CCL17 extracellular domain and the obtained positive clones are further characterized, the Fabs isolated from the clone lysates, and expressed as full length IgGs. Such phage display methods for isolating human antibodies are established in the art. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885, 793; 6,521,404; 6,544,731; 6,555,313; 6,582,915 and 6,593, 081 to Griffiths et al.

Preparation of immunogenic antigens and monoclonal antibody production can be performed using any suitable technique, such as recombinant protein production. The immunogenic antigens can be administered to an animal in the form of purified protein, or protein mixtures including whole cells or cell or tissue extracts, or the antigen can be formed de novo in the animal's body from nucleic acids encoding said antigen or a portion thereof.

The antibodies of the invention may be human or humanized.

The antibodies of the invention may be synthetic or recombinant.

The antibodies of the invention may be of IgA, IgD, IgE, IgG or IgM type. The antibodies of the invention may be of IgG1, IgG2, IgG3, IgG4 isotype.

Immune effector properties of the antibodies of the invention may be enhanced or silenced through Fc modifications by techniques known to those skilled in the art. For example, Fc effector functions such as C1q binding, complement dependent cytotoxicity (CDC), antibody-dependent: cell-mediated cytotoxicity (ADCC), phagocytosis, down regulation of cell surface receptors (e.g., B cell receptor; BCR), etc. can be modulated by modifying residues in the Fc responsible for these activities. Pharmacokinetic properties may also be enhanced by mutating residues in the Fc domain that extend antibody half-life. Exemplary Fc modifications are IgG4 S223P/L234A/L23SA, IgG2 M252Y/S254T/T256E (Dall'Acqua et al., *J Biol Chem* 261:23514-24, 2006; or IgG2 V234A/G237A/P238S, V234A/G237A/H268Q, H268A/V309L/A330 S/P331 or V234A/G237A/P233S/H268A/V309L/A330S/P331S on IgG2 (Intl. Pat. Publ. No. WO2011/066501), or those described in U.S. Pat. No. 6,737,056 (numbering according to the EU numbering).

In some embodiments, the antibody specifically binding human CCL17 comprises a substitution in an Fc region.

In some embodiments, the substitution comprises V234A, G237A, P236S, H268A, V309L, A330S or P331S substitution on IgG2, or S228P, L234A or L235A substitution on IgG4, wherein residue numbering is according to the EU Index.

Additionally, antibodies of the invention can be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function (Knight et al., *Plateles* 15:409-418, 2004; Leong et al., *Cytokine* 16:106-119, 2001; Yang et: al., *Protein Eng* 16:761-770, 2003).

Antibodies or fragments thereof of the invention modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn and Pluckthun, J Mol Biol 305:939-1010, 2001). Potential structure destabilising residues may be identified based upon the crystal structure of the antibody or by molecular modeling in certain cases, and the effect of the residues on antibody stability can be tested by generating and evaluating variants harboring mutations m the identified residues. One of the ways to increase antibody stability is to raise the thermal transition midpoint ($T_m$) as measured by differential scanning calorimetry (DSC). In general, the protein $T_m$ is correlated with its stability and inversely correlated with its susceptibility to unfolding and denaturation in solution and the degradation processes that depend on the tendency of the protein to unfold (Remmele et al., *Pharm Res* 15:200-208, 1997). A number of studies have found correlation between the ranking of the physical stability of formulations measured as thermal stability by DSC and physical stability measured by other methods (Bedu-Addo et al., *Pharm Res* 21:1353-1361, 2004; Gupta and Kaisheva, *AAPS PharSci*, 5E6, 2003; Maa and Hsu, *Int J Pharm* 140:155-168, 1996; Remmele et al., *Pharm Res* 15:200-208, 1997; Zhang et al., *J Pharm Sci* 93:3076-3089, 2004). Formulation studies suggest that a Fab Tm has implication for long-term physical stability of a corresponding mAb. Differences in amino acids in either framework or within the CDRs could have significant effects on the thermal stability of the Fab domain (Yasui et al., *FEBS Lett* 353:143-146, 1994).

CCL17 antibodies of the invention can be engineered into bispecific antibodies which are also encompassed within the scope of the invention. The VL and/or the VH regions of the antibodies of the invention can be engineered using published methods into single chain bispecific antibodies as structures such as Tan-dAbs designs (Int. Pat. Publ. No. WO1999/57150; U.S. Pat. Publ. No. US2011/0206672) or into bispecific scFVs as structures such as those disclosed in U.S. Pat. No. 5,869,620; Int. Pat. Publ. No. WO1995/15368, int. Pat. Publ. No. WO1997/14719 or Int. Pat. Publ. No WO2011/036460.

The VL and/or the VH regions of the antibodies of the invention can be engineered into bispecific full length antibodies, where each antibody arm binds a distinct antigen or epitope. Such bispecific antibodies are typically made by modulating the CH3 interactions between the two antibodies heavy chains to form bispecific antibodies using technologies such as those described m U.S. Pat. No. 7,695,936; Int. Pat. Publ. No. WO2004/111233; U.S. Pat. Publ. No. US2010/0015133; U.S. Pat. Publ. No. US2007/0287170; int. Pat. Publ. No. WO2003/119353; U.S. Pat. Publ. No. US2009/0182127; U.S. Pat. Publ. No. US2010/0286374; U.S. Pat. Publ. No. US2011/0123532; Int. Pat. Publ. No. WO2011/131746; Int. Pat. Publ. No. WO2011/143545; or U.S. Pat. Publ. No. US2012/0149876. Additional bispecific structures into which the VL and/or the VH regions of the antibodies of the invention can be incorporated are for example Dual Variable Domain Immunoglobulins (Int. Pat. Publ. No. WO2009/134776), or structures that include various dimerization domains to connect the two antibody arms with different specificity, such as leucine zipper or collagen dimerization domains (Int. Pat. Publ. No. WO2012/022311, U.S. Pat. Nos. 5,932,448; 6,833,441).

Another embodiment of the invention is an isolated polynucleotide encoding any of the antibody heavy chain variable regions or the antibody light chain variable regions of the invention. Certain exemplary polynucleotides are disclosed herein, however, other polynucleotides which, given the degeneracy of the genetic code or codon preferences in a given expression system, encode the antibodies of the invention are also within the scope of the invention. The polynucleotide sequences encoding a VH or a VL or a fragment thereof of the antibody of the invention can be operably linked to one or more regulatory elements, such as a promoter and enhancer, that allow expression of the nucleotide sequence in the intended host cell. The polynucleotide may be a cDNA.

Another embodiment of the invention is a vector comprising the polynucleotide of the invention. Such vectors may be plasmid vectors, viral vectors, vectors for baculovirus expression, transposon based vectors or any other vector suitable for introduction of the polynucleotide of the invention into a given organism or genetic background by any means. For example, polynucleotides encoding light and heavy chain variable regions of the antibodies of the invention, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include signal sequences, promoters (e.g. naturally associated or heterologous promoters), enhancer elements, and transcription termination sequences, and are chosen to be compatible with the host cell chosen to express the antibody. Once the vector has been incorporated into the appropriate host, the host is maintained under conditions suitable for high level expression of the proteins encoded by the incorporated polynucleotides.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences.

Suitable promoter and enhancer elements are known in the art. For expression in a bacterial cell, exemplary promoters include lad, lacZ, T3, T7, gpt, lambda P and trc. For expression in a eukaryotic cell, exemplary promoters include light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. For expression in a yeast cell, an exemplary promoter is constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1. (e.g., for use in *Pichia*). Selection of the appropriate vector and promoter is well within the level of ordinary skill in the art.

Large numbers of suitable vectors and promoters are known to those of skill in the art; many are commercially available for generating a subject recombinant: constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Another embodiment of the invention is a host cell comprising the vector of the invention. The term "host, cell" refers to a cell into which a vector has been introduced. It is understood that the term host cell is intended to refer not only to the particular subject cell but to the progeny of such a cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic ceLls, plant cells or archeal cells.

*Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (e.g., *S. cerevisiae*) and *Pichia* are examples of suitable yeast host cells. Exemplary eukaryotic cells may be of mammalian, insect, avian or other animal origins. Mammalian eukaryotic cells include immortalised cell lines such as hybridomas or myeloma cell lines such as SP2/0 (American Type Culture Collection (ATCC), Manassas, Va., CRL-1561), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonea Biologies, Walkersville, Md.), CHO-K1 (ATCC CRL-61) or DG44.

Another embodiment of the invention is a method of producing an antibody of the invention comprising culturing the host cell of the invention and recovering the antibody produced by the host cell. Methods of making antibodies and purifying them are well known in the art. Once synthesized (either chemically or recombinantly), the whole antibodies, their dimers, individual, light and heavy chains, or other antibody fragments such as VH or VL, can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or at least about 98% to 99%, or more, pure, e.g., free from contaminants such as cell debris, macromolecules other than a subject antibody, etc.

The polynucleotides encoding certain VH or VL sequences of the invention are incorporated into vectors using standard molecular biology methods. Host cell transformation, culture, antibody expression and purification are done using well known methods.

Methods of Treatment

Antibodies specifically binding human CCL17 may be suitable for treating or preventing a spectrum of CCL17-mediated conditions.

The term "CCL17-mediated condition" as used herein encompasses all diseases and medical conditions in which CCL17 plays a role, whether directly or indirectly, in the disease or medical condition, including the causation, development, progress, persistence or pathology of the disease or condition.

The term "CCL17-mediated inflammatory condition" as used herein refers to an inflammatory condition resulting at least partially from CCL17 biological activity. Exemplary CCL17-mediated inflammatory conditions are asthma and allergies.

The methods of the invention may be used to treat an animal patient belonging to any classification. Examples of such animals include mammals such as humans, rodents, dogs, cats and farm animals. For example, the antibodies of the invention are useful in the prophylaxis and treatment of CCL17-mediated conditions, such as asthma and respiratory allergic diseases such as allergic asthma, allergic rhinitis, chronic obstructive pulmonary disease (COPD), idiopathic pulmonary fibrosis (IPF), hypersensitivity lung diseases and the like, allergic diseases such as systemic anaphylaxis or hypersensitivity responses, drug allergies, allergic bronchopulmonary aspergillosis (ABPA), insect sting allergies and food allergies, inflammatory bowel diseases such as Crohn's disease, ulcerative colitis, ileitis and enteritis, vaginitis, psoriasis and inflammatory dermatoses such as dermatitis, eczema, atopic dermatitis, allergic contact dermatitis, urticaria and pruritus, vasculitis, spondyloarthropathies, scleroderma, autoimmune diseases, such as arthritis (including rheumatoid and psoriatic), multiple sclerosis, systemic lupus erythematosus, type 1 diabetes, glomerulonephritis, and the like, graft: rejection (including allograft rejection and graft-v-host disease), and other diseases in which undesired inflammatory responses are to be inhibited, such as atherosclerosis, myositis, T-cell mediated neurodegenerative diseases, multiple sclerosis, encephalitis, meningitis, hepatitis, nephritis, sepsis, sarcoidosis, allergic conjunctivitis, otitis, Castleman's disease, sinusitis, LPS-induced endotoxic shock, Behcet's syndrome and gout, The antibodies of the invention and are also useful in the preparation of a medicament for such treatment, wherein the medicament is prepared for administration m dosages defined herein.

The methods and uses of the present may be intended for use in animals and patients that have, or are at risk for developing any disease or condition associated with CCL17 expression or biological activity or in which CCL17 plays a biological role.

By not wishing to be bound by any theory, the antibodies of the invention may provide their efficacious effect in various inflammatory diseases by direct inhibition of Th2 cell recruitment and therefore simultaneous inhibition of multiple Th2 cytokines. The antibodies of the invention may provide an improved safety profile in comparison to anti-CCR4 antibodies by selectively blocking CCL17 only. The antibodies will not interact with platelets, which express CCR4. In addition, the antibodies will not block the beneficial innate immune effects of CCL22 on CCR4 (Matsukawa et al., *I. Immunol* 164:5332-8, 2000).

"Inflammatory condition" as used herein refers to acute or chronic localized or systemic responses to harmful stimuli, such as pathogens, damaged cells, physical injury or irritants, that are mediated in part by the activity of cytokines, chemokines, or inflammatory cells (e.g., neutrophils, monocytes, lymphocytes, macrophages, mast cells, dendritic cells, neutrophils) and is characterized in most instances by pain, redness, swelling, and impairment of tissue function.

Inflammatory pulmonary condition is an example of a CCL17-mediated inflammatory condition. Exemplary inflammatory pulmonary conditions include infection-induced pulmonary conditions including those associated with viral, bacterial, fungal, parasite or prion infections; allergen-induced pulmonary conditions; pollutant-induced pulmonary conditions such as asbestosis, silicosis, or berylliosis; gastric aspiration-induced pulmonary conditions, immune dysregulation, inflammatory conditions with genetic predisposition such as cystic fibrosis, and physical trauma-induced pulmonary conditions, such as ventilator injury. These inflammatory conditions also include asthma, emphysema, bronchitis, chronic obstructive pulmonary disease (COPD), sarcoidosis, histiocytosis, lymphangiomyomatosis, acute lung injury, acute respiratory distress syndrome, chronic lung disease, bronchopulmonary dysplasia, community-acquired pneumonia, nosocomial pneumonia, ventilator-associated pneumonia, sepsis, viral pneumonia, influenza infection, parainfluenza infection, rotavirus infection, human metapneumovirus infection, respiratory syncitial virus infection and *Aspergillus* or other fungal infections. Exemplary infection-associated inflammatory diseases may include viral or bacterial pneumonia, including severe pneumonia, cystic fibrosis, bronchitis, airway exacerbations and acute respiratory distress syndrome (ARDS). Such infection-associated conditions may involve multiple infections such as a primary viral infection and a secondary bacterial infection.

Asthma is an inflammatory disease of the lung that is characterized by airway hyperresponsiveness ("AHR"), bronchoconstriction, wheezing, eosinophilic or neutrophilic inflammation, mucus hypersecretion, subepithelial fibrosis, and elevated IgE levels. Patients with asthma experience "exacerbations", a worsening of symptoms, most commonly due to microbial infections of the respiratory tract (e.g. rhinovirus, influenza virus, *Haemophilus* influenza, etc.). Asthmatic attacks can be triggered by environmental factors (e.g. ascarids, insects, animals (e.g., cats, dogs, rabbits, mice, rats, hamsters, guinea pigs and birds), fungi, air pollutants (e.g., tobacco smoke), irritant gases, fumes, vapors, aerosols, chemicals, pollen, exercise, or cold air. Apart from asthma, several chronic inflammatory diseases affecting the lung are characterized by neutrophil infiltration to the airways, for example chronic obstructive pulmonary disease (COPD), bacterial pneumonia and cystic fibrosis (Linden et al., *Eur Respir J* 15:973-7, 2000; Rahman et al., *Clin Immunol* 115:268-76, 2005), and diseases such as COPD, allergic rhinitis, and cystic fibrosis are characterized by airway hyperresponsiveness (Fahy and O'Byrne *Am J Respir Crit Care Med* 163:822-3, 2001).

In allergic asthma, the presence of high levels of allergen-specific IgE is a reflection of an aberrant Th2 cell immune response to commonly inhaled environmental allergens. Allergens are presented to T cells by dendritic cells (DCs) that continuously sample incoming foreign antigens. Upon proper activation by DCs, allergen-specific lymphocytes that are present in diseased airways produce Th2 cytokines interleukin (IL)-4, IL-5 and IL-13 that furthermore control leukocyte extravasation, goblet cell hyperplasia and bronchial hyper-reactivity (BHR). CCL17 produced by DCs induce the selective migration of Th2 cells but not Th1 cells through triggering CCR4. In murine models of asthma, that treatment with anti-CCL17 antibodies reduced the number of CD4+ T cells and eosinophils in bronchoalveolar lavage (BAL) fluid, the production of Th2 cytokines and airway hyper-responsiveness after allergen challenge, suggesting that CCL17 neutralization is a feasible strategy for inhibiting allergic inflammation in humans.

Commonly used animal models for asthma and airway inflammation include the ovalbumin challenge model, methacholine sensitization models and sensitization with *Aspergillus* fumigates (Hessel et al., *Eur J Pharmacol* 293: 401-12, 1995). Inhibition of cytokine and chemokine production from cultured human bronchial epithelial cells, bronchial fibroblasts or airway smooth muscle cells can also be used as in vitro models. The administration of antibodies of the invention to any of these models can be used to evaluate the efficacy to ameliorate symptoms and alter the course of asthma, airway inflammation, COPD and the like.

Atopic dermatitis is an example of a CCL17-mediated inflammatory condition.

One aspect of the invention is a method of treating a CCL17-mediated disease, comprising administering to a subject in need thereof the antibody of the invention for a time sufficient to treat the CCL17-mediated disease.

In some embodiments, the CCL17-mediated disease is an inflammatory disease.

In some embodiments, the inflammatory disease is asthma, ulcerative colitis (UC), atopic dermatitis (AD) or idiopathic pulmonary fibrosis (IPF).

One embodiment of the invention is a method of treating asthma, comprising administering to a subject an antibody of the invention for a time sufficient to treat asthma.

Administration/Pharmaceutical Compositions

The invention provides for pharmaceutical compositions comprising the antibodies specifically binding CCL17 of the invention of the invention and a pharmaceutically acceptable carrier. For therapeutic use, the antibodies specifically binding CCL17 of the invention may be prepared as pharmaceutical compositions containing an effective amount of the domain, molecule or antibody as an active ingredient in a pharmaceutically acceptable carrier. The term "carrier" refers to a diluent, adjuvant, excipient, or vehicle with which the active compound is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or antibodies of the invention in such pharmaceutical formulation may vary widely, i.e., from less than about 0.5%, usually at or at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lippincott Williams and Wilkins, Philadelphia, Pa. 2006, Part 5, Pharmaceutical Manufacturing pp 691-1092, See especially pp. 958-989.

The mode of administration for therapeutic use of the antibodies specifically binding CCL17 of the invention may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, powder, gel, particle; and contained m a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Thus, a pharmaceutical composition of the invention for intramuscular injection may be prepared to contain 1 ml sterile buffered water, and between about 1 ng to about 100 mg/kg, e.g. about 50 ng to about 30 mg/kg or more preferably, about 5 mg to about 25 mg/kg, of the antibodies specifically binding CCL17 of the invention.

The dose given to a patient having a CCL17-mediated condition is sufficient to alleviate symptoms or treat the CCL17-mediated condition ("therapeutically effective amount") and is sometimes 0.1 to 10 mg/kg body weight, for example 1, 2, 3, 4, 5, 6, 7, 8, 9 or 10 mg/kg, but may even higher, for example 15, 20, 30, 40, 50, 60, 70, 80, 90 or 100 mg/kg. A fixed unit dose may also be given, for example, 50, 100, 200, 500 or 1000 mg, or the dose may be based on the patient's surface area, e.g., 400, 300, 250, 200, or 10 mg/m$^2$. Usually between 1 and 8 doses, (e.g., 1, 2, 3, 4, 5, 6, 7 or 8) are administered, but 10, 12, 20 or more doses may be given. Administration of the antibodies specifically binding CCL17 of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

The dosage of the CCL17 antibodies of the invention that will be effective in the treatment of inflammatory diseases such as asthma can be determined by administering the CCL17 antibodies to relevant animal models well known in the art and as described herein.

In vitro assays can optionally be employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems. The antibodies of the invention may be tested for their efficacy and effective dosage using any of the models described herein.

For example, a pharmaceutical composition comprising the antibodies specifically binding CCL17 of the invention for intravenous infusion may be made up to contain about 200 ml of sterile Ringer's solution, and about 3 mg to about 2400 mg, about 400 mg to about 1600 mg, or about 400 mg to about 600 mg or the antibodies specifically binding CCL17 of the invention for administration to a 80 kg patient. Methods for preparing parenterally administrable compositions are well known and are described in more detail in, for example, "Remington's Pharmaceutical Science", 15th ed., Mack Publishing Company, Easton, Pa.

The antibodies specifically binding CCL17 of the invention may be lyophilized for storage and reconstituted in a suitable carrier prior to use. This technique has been shown to be effective with conventional protein preparations and art-known lyophilization and reconstitution techniques can be employed.

The antibodies specifically binding CCL17 of the invention may be administered in combination with a second therapeutic agent simultaneously, sequentially or separately.

The present invention will now be described with reference to the following specific, non-limiting examples.

Example 1. Generation of CCL17 Neutralizing Antibodies

Human CCL17 binding Fabs were selected from de novo pIX phage display libraries described in Shi et al., J. Mol. Biol. 397:385-396, 2010; Int. Pat. Publ. No. WO2009/0S5462; U.S. Pat. Publ. No. US2010/0021477; U.S. Pat. Publ. No. US2012/0108795. Briefly, the libraries were generated by diversifying human scaffolds where germline VH genes IGHV1-69*01, IGHV3-23*01, and IGHV5-51*01 were recombined with the human IGHJ-4 minigene via the H3 loop, and human germline VL kappa genes 012 (IGKV1-39*01), L6 (IGKV3-11*01), A27 (IGKV3-20*01), and B3 (IGKV4-1*01) were recombined with the IGKJ-1 minigene to assemble complete VH and VL domains. The positions in the heavy and light chain variable regions around H1, H2, L1, L2 and L3 loops corresponding to positions identified to be frequently in contact with protein and peptide antigens were chosen for diversification. Sequence diversity at selected positions was limited to residues occurring at each position in the IGHV or IGLV germline gene families of the respective IGHV or IGLV genes. Diversify at the H3 loop was generated by utilizing short to mid-sized synthetic loops of lengths 7-14 amino acids. The amino acid distribution at H3 was designed to mimic the observed variation of amino acids in human antibodies. Library design is detailed in Shi et. al., J Mol Biol 397:385-96, 2010. The scaffolds utilized to generate libraries were named according to their human VH and VL germline gene origin. The three heavy chain libraries were combined with the four germline light chains or germline light chain libraries to generate 24 unique VH:VL combinations for screening. All 24 VH:VL library combinations were utilized in phage panning experiments against human CCL17.

The libraries were panned using human CCL17 of SEQ ID NO: 1. Briefly, human CCL17 was biotinylated using standard methods and the biotinylated human CCL17 (Bt-huCCL17) was captured on streptavidin-coated magnetic beads (Dynal, M280), and the Fab-pIX phage libraries were added to the beads. Bt-huCCL17 concentrations used were 100 nM for rounds 1 and 2 and 10 mM for rounds 3 and 4). Screening was done by ELISA for Fab binding to human CCL17 protein. For panning, the bt-huCCL17 coated magnetic beads were washed and blocked with PBST-M (BPS with 0.057 Tween-20 and 3% non-fat dry milk). Blocked phage from the libraries were added to the beads and rotated at room temperature for round 1. Beads were washed and then incubated in a culture of log phase E. coli, (MC1061F') cells and the infected E. coli were grown on LB agar plates overnight at 37°c. The next morning cultures were scraped from the plates in 2 mL 2×YT (20% glycerol) per plate, 50 µL of bacterial suspension was added to 50 mL 2×YT (Carb) and grown at 37° C. shaking for up to 2 hours. Helper phage was added to mid-log phase cultures and the cultures were incubated at 37° C. for 30 minutes. Kanamycin and IPTG were added to each culture to final concentrations of 35 µg/mL and 1 mM, respectively, and grown overnight at 30° C. shaking. The amplified phage from the bacterial media was precipitated using PEG/NaCl and re-suspended in 1 mL PBS. 200 µL was used for the next round of panning.

After three rounds of panning, phagemid DMA was isolated from the infected MC1061F' cells and digested with restriction enzymes to remove the sequence encoding pIX, and the linearized plasmid DMA was excised and purified from agarose gels. This DMA was then self-ligated with T4 DNA ligase. The ligated DNA was electroporated into MC1061F' cells and plated onto LB (Carb/Glucose) agar plates. Colonies from this electroporation were picked for the ELISA screen and assessment of Fab expression. The Fabs contain an in-frame His tag at the C-terminus of the heavy chain. From the initial screen, 24 Fabs were partially purified via the C-terminal His tag using standard methods and characterized further.

The Fabs were characterized for their binding to human CCL17 (SEQ ID NO: 1), cyno CCL17 (SEQ ID NO: 2) and cyno CCL22 (SEQ ID NO: 3) in an ELISA assay. Briefly, Maxisorp 96 well plates were coated with 1 µg/ml Goat anti-human Kappa (Southern Biotech). Semi-purified Fab was added to each plate. Biotinylated huCCL17, cCCL17 or cCCL22 was added to each Fab-captured well. Proteins bound to the captured Fabs were detected using Streptavidin:HRP. Five Fabs (F21, F24, F34, F43 and F44) that bound to both human and cyno CCL17 but not cyno CCL22 were selected for affinity maturation.

Example 2 Affinity Maturation of Anti-CCL17 Antibodies

Five Fabs were selected for affinity maturation based on their initial characterization profile. The Fabs were affinity-matured by diversifying the light chains using the in-line maturation technology described in Shi et al. (Shi et al., *J Mol Biol* 397:385-396, 2010) and keeping the heavy chain invariant. The heavy chain in the Fabs was either VH3-23 or VH5-51. F24 affinity maturation libraries produced improved CCL17 binders.

Briefly, F24 was affinity-matured using the B3 light chain library. The B3 library diversification scheme is shown in Table 2. The positions are indicated as Kabat numbering.

TABLE 2

| Residue position (Kabat) | Germline residue | Library compositions |
|---|---|---|
| 27d | Y | SYHFA |
| 30 | K | KTNE |
| 32 | Y | YFHNWDAS |
| 50 | W | YWSRDYA |
| 91 | Y | YSHA |
| 92 | Y | YNDSHIFK |
| 93 | S | SNTDGHR |
| 94 | T | TYLVFAS |
| 96 | L | WYFLIR |

The VH regions of the Fabs were cloned into the LC library phagemid resulting in a complete re-diversification of the LC for each Fab. VH regions were isolated by restriction digestion of DNA minipreps using NcoI and ApaI. The VH regions were gel isolated and ligated into similarly digested LC library DNA. Ligations were purified and transformed into MC1061F' cells. Cells were grown in 2×YT (Carb) until log phase growth ($OD_{600\,nm} \approx 0.6$) was achieved. Helper phage was added and the cultures were incubated at 37° C. for 30 minutes. Kanamycin and IPTG were added to each culture to final concentrations of 35 ug/mL and 1 mM, respectively, and grown overnight at 30° C. shaking. The phage from the bacterial media was precipitated using PEG/NaCl and re-suspended in PBS.

For affinity maturation panning, Bt-CCL17 was captured on 50 µl of SA-coated magnetic beads. Antigen concentrations were 100 nM for round 1, 10 nM for round 2, and 10 nM for round 3. Beads were subjected to 6 washes with PBST and one wash with PBS, followed by *E. coli* infection as described above. Isolation of Fab expression plasmids and expression of Fabs was done as described.

Affinity-matured Fabs were screened in an ELISA assay for binding to huCCL17 (SEQ ID NO: 1), cCCL17 (SEQ ID NO: 2) and cCCL22 (SEQ ID NO: 3) as described above for binding to huCCL17. Identified clones were sequenced, converted to full IgG1 antibodies and their binding to huCCL17, cCCL17 and cCCL22 was confirmed using MSD-SEA.

CDR sequences of the parent and affinity-matured antibodies are shown m Table 3 and Table 4 for heavy chain and light chain CDRs, respectively.

TABLE 3

| mAb ID | HCDR1 sequence | SEQ ID NO: | HCDR2 sequence | SEQ ID NO: | HCDR3 sequence | SEQ ID NO: |
|---|---|---|---|---|---|---|
| C17F24 (parent) | SYWIG | 4 | IIDPSDSDTRYSPSFQG | 5 | VGPADVWDSFDY | 6 |
| C17B234 | SYWIG | 4 | IIDPSDSDTRYSPSFQG | 5 | VGPADVWDSFDY | 6 |
| C17B235 | SYWIG | 4 | IIDPSDSDTRYSPSFQG | 5 | VGPADVWDSFDY | 6 |
| C17B236 | SYWIG | 4 | IIDPSDSDTRYSPSFQG | 5 | VGPADVWDSFDY | 6 |
| C17B237 | SYWIG | 4 | IIDPSDSDTRYSPSFQG | 5 | VGPADVWDSFDY | 6 |
| C17B238 | SYWIG | 4 | IIDPSDSDTRYSPSFQG | 5 | VGPADVWDSFDY | 6 |
| C17B239 | SYWIG | 4 | IIDPSDSDTRYSPSFQG | 5 | VGPADVWDSFDY | 6 |
| C17B240 | SYWIG | 4 | IIDPSDSDTRYSPSFQG | 5 | VGPADVWDSFDY | 6 |
| C17B241 | SYWIG | 4 | IIDPSDSDTRYSPSFQG | 5 | VGPADVWDSFDY | 6 |
| C17B242 | SYWIG | 4 | IIDPSDSDTRYSPSFQG | 5 | VGPADVWDSFDY | 6 |
| C17B243 | SYWIG | 4 | IIDPSDSDTRYSPSFQG | 5 | VGPADVWDSFDY | 6 |
| C17B244 | SYWIG | 4 | IIDPSDSDTRYSPSFQG | 5 | VGPADVWDSFDY | 6 |

TABLE 4

| mAb ID | LCDR1 sequence | SEQ ID NO: | LCDR2 sequence | SEQ ID NO: | LCDR3 sequence | SEQ ID NO: |
|---|---|---|---|---|---|---|
| C17F24 (parent) | KSSQSVLYSSNNKNYLA | 7 | WASTRES | 19 | QQYYSTPLT | 27 |

TABLE 4-continued

| mAb ID | LCDR1 sequence | SEQ ID NO: | LCDR2 sequence | SEQ ID NO: | LCDR3 sequence | SEQ ID NO: |
|---|---|---|---|---|---|---|
| C17B234 | KSSQSVLLSFDNINKLA | 8 | NASTRES | 20 | QQFYSVPST | 28 |
| C17B235 | KSSQSVLYSFYNFNALA | 9 | HASTRES | 21 | QQFYATPFT | 29 |
| C17B236 | KSSQSVLLSPWNSNQLA | 10 | GASTRES | 22 | QQYYLIPST | 30 |
| C17B237 | KSSQSVLTSYNNSNYLA | 11 | LASTRES | 23 | QQYLSPPST | 31 |
| C17B238 | KSSQSVLISAFNQNPLA | 12 | DASTRES | 24 | QQYQFIPFT | 32 |
| C17B239 | KSSQSVLSSFTNTNTLA | 13 | HASTRES | 21 | QQYLIYPST | 33 |
| C17B240 | KSSQSVLYSHVNYNALA | 14 | NASTRES | 20 | QQYYTLPAT | 34 |
| C17B241 | KSSQSVLNSFTNNNALA | 15 | EASTRES | 25 | QQTNSIPLT | 35 |
| C17B242 | KSSQSVLFSHDNLNTLA | 16 | HASTRES | 21 | QQYYAVPQT | 36 |
| C17B243 | KSSQSVLNSFDNKNDLA | 17 | EASTRES | 25 | QQHWQTPLT | 37 |
| C17B244 | KSSQSVLSSITNVNDLA | 18 | TASTRES | 26 | QQYYHDPFT | 38 |

Example 3 Binding of Affinity-Matured Anti-CCL17 Antibodies to Human and Cyno CCL17

Antibodies were assessed for their binding to human CCL17 and cyno CCL17 using solution equilibrium affinity (SEA). The procedure for these experiments was similar to that used by Haenel et al (Haenel et al., *Anal Biochem* 339:182-184, 2005). To prepare the antigen-antibody complexes, human CCL17 or cyno CCL17 was serially diluted in Tris-Based Saline buffer containing 0.05% Tween-20, TEST, (Thermo Scientific) at a 1:6 ratio starting at a concentration of 2,000,000 pM in 96-deep well polypropylene plates. Equal volumes of the anti-hCCL17 mAbs at 40 pM or 200 pM were added to each chemokine dilution to obtain mixtures containing the serial dilution of chemokines starting at a final concentration of 1 pM and a constant concentration (20 pM or 100 pM) of anti-CCL17 antibody. The mixtures were prepared in duplicate and incubated at 4° C. for 48 hours to reach equilibrium. The free antibody was detected using a SECTOR Imager 6000 (Meso Scale Discovery) instrument. The resulting binding curves were fitted to obtain the dissociation equilibrium constant ($K_D$) using the GraphPad Prism software (v 5.01) using a 1:1 binding model to perform nonlinear least-square regression analysis of the data. Table 5 shows affinities of the antibodies to human and cyno CCL17. The affinities ranged from about 2 pM to about 700 pM for human CCL17 and from about 200 pM to about 9500 pM to cyno CCL17. The generated antibodies bound human CCL17 with about 2- to about 150 fold higher affinities when compared to binding to cyno CCL17.

TABLE 5

| mAb ID | Affinity (pM) | | Fold binding |
|---|---|---|---|
| | human CCL17 | cyno CCL17 | human/cyno CCL17 |
| C17F24 (parent) | 1000 | ND* | |

TABLE 5-continued

| mAb ID | Affinity (pM) | | Fold binding |
|---|---|---|---|
| | human CCL17 | cyno CCL17 | human/cyno CCL17 |
| C17B234 | 2 | 230 | 115.0 |
| C17B235 | 72 | 9497 | 131.9 |
| C17B236 | 39 | 297 | 7.6 |
| C17B237 | 657 | 3066 | 4.7 |
| C17B238 | 115 | 1456 | 12.7 |
| C17B239 | 92 | 630 | 6.8 |
| C17B240 | 83 | 4596 | 55.4 |
| C17B241 | 50 | 583 | 11.7 |
| C17B242 | 167 | 384 | 2.3 |
| C17B243 | 28 | 677 | 24.2 |
| C17B244 | 33 | 565 | 17.1 |

*Not determined

Example 4 Optimization of CCL17 Antibodies

C17B234 and C17B240 anti-CCL17 antibodies contained a potential N-linked glycosylation site at the beginning of the LCDR2 ("NAS"). The asparagine residue (N) at residue position 50 (Kabat numbering) of C17B234 was mutated to six different amino acids (A, D, G, S, T and I).

A potential aspartic acid isomerization motif, "DS" was identified in the HCDR3 in the parent C17F24 and all its affinity matured variants. To test the effect of substitutions at this position, the serine residue at position 100c. (Kabat numbering) was mutated to A, T or S or the D at position 100b was mutated to E in the heavy chain of mAb C17B234. The resulting heavy chains were paired with the light chain of mAb C17B258.

The antibodies were expressed as IgG1 and their affinity to human and cyno CCL17 was measured. Table 6 and Table 7 shows the heavy and light chain CDR sequences or the optimised antibodies. Table 8 shows the affinity of the antibodies for human and cyno CCL17. Mutagenesis of N50 in the light chain resulted in improved binding of 2- to 100-fold.

TABLE 6

| mAb ID | HCDR1 sequence | SEQ ID NO: | HCDR2 sequence | SEQ ID NO: | HCDR3 sequence | SEQ ID NO: |
|---|---|---|---|---|---|---|
| C17B257 | SYWIG | 4 | IIDPSDSDTRYSPSFQG | 5 | VGPADVWDSFDY | 6 |
| C17B258 | SYWIG | 4 | IIDPSDSDTRYSPSFQG | 5 | VGPADVWDSFDY | 6 |
| C17B260 | SYWIG | 4 | IIDPSDSDTRYSPSFQG | 5 | VGPADVWDSFDY | 6 |
| C17B262 | SYWIG | 4 | IIDPSDSDTRYSPSFQG | 5 | VGPADVWDSFDY | 6 |
| C17B263 | SYWIG | 4 | IIDPSDSDTRYSPSFQG | 5 | VGPADVWDSFDY | 6 |
| C17B264 | SYWIG | 4 | IIDPSDSDTRYSPSFQG | 5 | VGPADVWDSFDY | 6 |
| C17B293 | SYWIG | 4 | IIDPSDSDTRYSPSFQG | 5 | VGPADVWDAFDY | 42 |
| C17B294 | SYWIG | 4 | IIDPSDSDTRYSPSFQG | 5 | VGPADVWDTFDY | 43 |
| C17B295 | SYWIG | 4 | IIDPSDSDTRYSPSFQG | 5 | VGPADVWESFDY | 44 |

TABLE 7

| mAb ID | LCDR1 sequence | SEQ ID NO: | LCDR2 sequence | SEQ ID NO: | LCDR3 sequence | SEQ ID NO: |
|---|---|---|---|---|---|---|
| C17B257 | KSSQSVLLSFDNINKLA | 8 | AASTRES | 39 | QQFYSVPST | 28 |
| C17B258 | KSSQSVLLSFDNINKLA | 8 | DASTRES | 24 | QQFYSVPST | 28 |
| C17B260 | KSSQSVLLSFDNINKLA | 8 | GASTRES | 22 | QQFYSVPST | 28 |
| C17B262 | KSSQSVLLSFDNINKLA | 8 | SASTRES | 40 | QQFYSVPST | 28 |
| C17B263 | KSSQSVLLSFDNINKLA | 8 | TASTRES | 26 | QQFYSVPST | 28 |
| C17B264 | KSSQSVLLSFDNINKLA | 8 | IASTRES | 41 | QQFYSVPST | 28 |
| C17B293 | KSSQSVLLSFDNINKLA | 8 | DASTRES | 24 | QQFYSVPST | 28 |
| C17B294 | KSSQSVLLSFDNINKLA | 8 | DASTRES | 24 | QQFYSVPST | 28 |
| C17B295 | KSSQSVLLSFDNINKLA | 8 | DASTRES | 24 | QQFYSVPST | 28 |

TABLE 8

| mAb ID | Affinity (pM) Human CCL17 | Affinity (pM) Cyno CCL17 | Fold binding human/cyno CCL17 |
|---|---|---|---|
| c17B257 | 0.1 | 65.6 | 656.0 |
| C17B258 | 0.1 | 41.6 | 416.0 |
| C17B260 | 0.5 | 36.4 | 72.8 |
| C17B262 | 0.3 | 55.5 | 185.0 |
| C17B263 | 0.1 | 75.59 | 755.9 |
| C17B264 | 0.4 | 71.83 | 179.6 |
| C17B293 | <0.1 | 39 | |
| C17B294 | 1 | 22 | 22.0 |
| C17B295 | 175 | 29892 | 170.8 |

A Tryptophan residue in HCDR3 at position 100a (Kabat numbering) in mAb of C17B236 was identified as a putative site for undesired post translational oxidation. This residue was mutated to 17 other amino acids (all except C and M) in the Fab parent of C17B236, C17F319 which mAb is this. Kunkel's mutagenesis was performed with "NNK" or defined codon oligonucleotides to produce this panel. These Fabs were then screened using a ranking ELISA for binding to both bt-human and bt-cyno CCL17. Five variants (W→R, Y, F, T, I) showed some binding in a Fab binding ELISA (Table 5). The best three were converted to mAb (M17B288, C17B289, C17B290) for expression and MSD-SEA (Table 6). Most variants displayed reduced affinity to the human and cyno CCL17. VH and VL sequences of the antibodies are shown m Table 9.

TABLE 9

| mAb | VH SEQ ID NO: | VL SEQ ID NO: |
|---|---|---|
| C17F24 (parent) | 45 | 49 |
| C17B234 | 45 | 50 |
| C17B235 | 45 | 51 |
| C17B236 | 45 | 52 |
| C17B237 | 45 | 53 |
| C17B238 | 45 | 54 |
| C17B239 | 45 | 55 |

TABLE 9-continued

| mAb | VH SEQ ID NO: | VL SEQ ID NO: |
|---|---|---|
| C17B240 | 45 | 56 |
| C17B241 | 45 | 57 |
| C17B242 | 45 | 58 |
| C17B243 | 45 | 59 |
| C17B244 | 45 | 60 |
| C17B257 | 45 | 61 |
| C17B258 | 45 | 62 |
| C17B260 | 45 | 63 |
| C17B262 | 45 | 64 |
| C17B263 | 45 | 65 |
| C17B264 | 45 | 66 |
| C17B293 | 46 | 62 |
| C17B294 | 47 | 62 |
| C17B295 | 48 | 62 |

Example 5 Selection of Constant Regions

Select antibodies were cloned as IgG2 or IgG4 with following substitutions: IgG4 S228P/L234A/L235A or IgG2 V234A/G237A/P238S/H268A/V309L/A330S/P331S using standard methods. Table 10 shows the resulting antibodies

TABLE 10

| mAb name | isotype | Variable regions from mAb |
|---|---|---|
| C17B302 | IgG2 V234A/G237A/P238S/H268A/V309L/A330S/P331S | C17B293 |
| C17B311 | IgG4 S228P/L234A/L235A | C17B293 |
| C17B301 | IgG2 V234A/G237A/P238S/H268A/V309L/A330S/P331S | C17B294 |
| C17B312 | IgG4 S228P/L234A/L235A | C17B294 |

Heavy and light chains of certain antibodies are shown below:

CB302 HC
(SEQ ID NO: 67)
EVQLVQSGAEVKKPGESLKISCKGSGYSFTSYWIGWVRQMPGKGLEWMGI

IDPSDSDTRYSPSFQGQVTISADKSISTAYLQWSSLKASDTAMYYCARVG

PADVWDAFDYWGQGTLVTVSSASTKGPSVFPLAPCSRSTSESTAALGCLV

KDYFPEPVTVSWNSGALTSGVHTFPAVLQSSGLYSLSSVVTVTSSNFGTQ

TYTCNVDHKPSNTKVDKTVERKCCVECPPCPAPPAAASSVFLFPPKPKDT

LMISRTPEVTCVVVDVSAEDPEVQFNWYVDGVEVHNAKTKPREEQFNSTF

RVVSVLTVLHQDWLNGKEYKCKVSNKGLPSSIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK

CB302 LC
(SEQ ID NO: 68)
DIVMTQSPDSLAVSLGERATINCKSSQSVLLSFDNINKLAWYQQKPGQPP

KLLIYDASTRESGVPDRFSGSGSGTDFTLTISSLQAEDVAVYYCQQFYSV

PSTFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC

CB301 HC
(SEQ ID NO: 69)
EVQLVQSGAEVKKPGESLKISCKGSGYSFTSYWIGWVRQMPGKGLEWMGI

IDPSDSDTRYSPSFQGQVTISADKSISTAYLQWSSLKASDTAMYYCARVG

PADVWDTFDYWGQGTLVTVSSASTKGPSVFPLAPCSRSTSESTAALGCLV

KDYFPEPVTVSWNSGALTSGVHTFPAVLQSSGLYSLSSVVTVTSSNFGTQ

TYTCNVDHKPSNTKVDKTVERKCCVECPPCPAPPAAASSVFLFPPKPKDT

LMISRTPEVTCVVVDVSAEDPEVQFNWYVDGVEVHNAKTKPREEQFNSTF

RVVSVLTVLHQDWLNGKEYKCKVSNKGLPSSIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK

CB301 LC
(SEQ ID NO: 70)
DIVMTQSPDSLAVSLGERATINCKSSQSVLLSFDNINKLAWYQQKPGQPP

KLLIYDASTRESGVPDRFSGSGSGTDFTLTISSLQAEDVAVYYCQQFYSV

PSTFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC

Example 6 Characterization of Anti-CCL17 Antibodies

Select anti-CCL17 antibodies were characterized in calcium flux, β-arrestin reporter assays and in chemotaxis assay to assess their ability to inhibit CCL17 biological activities.

Calcium Flux Assay.

Calcium mobilization assay was used to test for ability of hybridoma mAbs to neutralize CCL17 signaling. CCRF-CEM cells (ATCC® CCL-119™) were cultured in RPMI with GlutaMAX; 10% FBS; 10 mM Hepes, 1 mM Sodium Pyruvate, 4500 mg/L glucose, and 1500 mg/ml Sodium bicarbonate at 37° C. incubator with 5/$CO_2$ saturation. Cells were labeled with dye using the Fluo-8 NW No Wash Calcium Assay Kit (#36315) from ABD Bioquest, Inc. Test antibodies and 10 ng/mL human CCL17 or 5 ng/mL cyno CCL17 were pre-incubated with the test antibodies and the mixture was added to the cells. Fluorescent signal was detected using FDSS 6000 (Hamamatsu, Bridgewater, N.J.) to using 490 nm excitation and 525 ran emission.

β-Arrestin Reporter Assay.

β-arrestin assay was used to assess the ability of the anti-CCL17 antibodies to neutralise CCL17 function. Assay was performed using the PathHunter express β-arrestin assay (DiscoveRx). Briefly, ability of anti-CCL17 antibodies to inhibit CCL17-induced β-arresting recruitment was assessed in Hek293 cells co-expressing CCR4 fused in frame with the small enzyme fragment ProLink™ and a fusion protein of δ-Arrestin and the N-terminal deletion mutant of β-gal (called enzyme acceptor or EA). Anti-CCL17 antibodies at various concentrations (0.15 nM-1 pM) were combined with 20 nM CCL17 and the mixture was incubated at 37° C. for 20-30 minutes prior to adding the antibody-CCL17 complex to the cells. The mixture was then applied to the cells and incubated at 37° C. (95?: 02/5% $CO_2$) for 90 minutes. 55 µl of detection reagent was added per well and incubated for 60 min at room temperature. Samples were read on a standard luminescence plate reader, and $IC_{50}$ values were calculated.

Chemotaxis Assay:

Chemotaxis assay was used to demonstrate that the anti-CCL17 antibodies inhibit CCL17 function. The migration of the HSC-F cells (HSC-F cells were obtained through the N1H Nonhuman Primate Reagent Resource) or CCRF-CEM cells (ATCC® CCL-119™) was assessed using a 96-well chemotaxis chamber using a 5 urn polycarbonate filter according to protocol described in Imai et al. 1997; Imai et al. 1999. Briefly, the lower chambers were filled with 320 μl RPMI/BSA 0.1% and 1 nM of the human or cyno CCL17 without or with different concentrations of the antibodies (0.125, 0.25, 0.51 and 10 μg/ml) and then were carefully overlaid with the polycarbonate membrane. Cells were washed with PBS and suspended in RPMI/BSA 0.1% at $0.5 \times 10^6$ cells/ml, and the cell suspension was added to the upper chambers. The chambers were incubated for 60 min in a 5% $CO_2$-humidified incubator at 37° C., and cells migrating across the membrane into the lower chamber were determined using The Cell Titer-Glo Luminescence Cell Viability.

Table 11 shows the IC50 values for the calcium flux assay. The data is an average of three independent experiments. Each mAb completely neutralized the calcium flux induced by human or cyno CCL17 using either 10 ng/ml (1.25 nM) human CCL17 or 5 ng/ml (0.625 nM) cyno CCL17 and as shown in Table 11, $IC_{50}$ values were roughly equivalent for each of the antibodies against both human and cyno protein.

TABLE 11

| mAb | $IC_{50}$ (nM) | |
|---|---|---|
| | Human CCL17 | Cyno CCL17 |
| C17B302 | 0.593 | 0.238 |
| C17B311 | 0.553 | 0.239 |
| C17B318 | 0.275 | 0.237 |
| C17B319 | 0.753 | 0.289 |
| C17B234 | 0.421 | 0.369 |
| C17B235 | 0.558 | 0.919 |
| C17B236 | 0.385 | 0.349 |
| C17B237 | 0.882 | 0.549 |
| C17B238 | 0.387 | 0.348 |
| C17B239 | 0.427 | 0.430 |
| C17B240 | 0.405 | 0.308 |
| C17B241 | 0.456 | 0.339 |
| C17B242 | 0.483 | 0.340 |
| C17B243 | 0.231 | 0.310 |
| C17B244 | | 0.311 |

Table 12 shows the $IC_{50}$ values for β-arrestin assay. The data is an average of three independent experiments. All of the mAbs were able to completely inhibit human or cyno CCL17-induced β-arrestin recruitment at 20 nM and dose-dependently inhibit β-arrestin recruitment induced by human or cyno CCL17 with equivalent potency.

TABLE 12

| | Human CCL17 | | Cyno CCL17 | |
|---|---|---|---|---|
| | $IC_{50}$ (nM) | STD | $IC_{50}$ (nM) | STD |
| C17B302 | 13.94 | 9.56 | 13.412 | 6.403 |
| C17B311 | 10.65 | 2.89 | 10.324 | 2.569 |
| C17B318 | 11.006 | 2.886 | 12.141 | 2.294 |
| C17B319 | 14.225 | 4.133 | 17.51 | 6.605 |
| C17B234 | 8.42 | 5.525 | 5.3915 | 0.043 |
| C17B236 | 6.98 | 3.33 | 9.502 | 0.073 |

FIG. 1 and FIG. 2 show the inhibition of chemotaxis with select antibodies in human and cyno cells, respectively. All antibodies tested inhibited both human CCL17-induced CCRF-CEM cell chemotaxis at a level of inhibition of about 50% at an antibody concentration of 0.5 pg/ml. C17B302 and C17B311 inhibited cyno HSC-F cell chemotaxis induced by cyno CCL17 at a level of inhibition of about 50% at antibody concentration of 0.5 μg/ml.

Example 7. Epitope Mapping of Anti-CCL17 Antibody C17B236

The binding epitope of antibody C17B236 (VH: SEQ ID NO: 45; VL: SEQ ID NO: 52) was determined by X-ray crystallography.

Human CCL17 was expressed in *E. coli*, isolated from inclusion bodies and refolded. The Fab fragment of mAb C17B236 was expressed in HEK293F cells. The CCL17: C17B236 complex was prepared by mixing at a molar ratio of 1.6:1 with an excess of CCL17. The complex was then purified by size exclusion chromatography. The complex was crystallized by the vapor-diffusion method from solution containing 20% PEG 3350 and 0.2 M K/Na tartrate. The X-ray diffraction data were collected to 1.9 Å resolution. The structure was determined by molecular replacement and refined to an R-factor of 18.0%.

Figure 7:
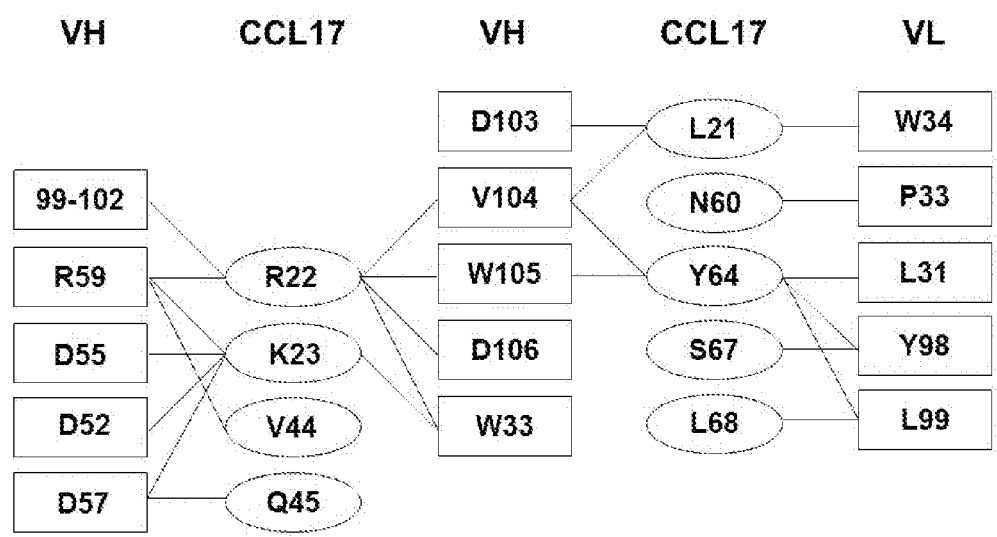
FIG. 7 shows the epitope and paratope residues of antibody C17B236. VH and VL paratope residues are boxed, and CCL17 epitope residues are circled. Residue numbering is according to SEQ ID NO: 45 VH), SEQ ID NO: 52 (VL), SEQ ID NO: 1 (CCL17).

C17B236 epitope is conformational and spans 3 segments of the CCL17 molecule, namely two loops (residues 21-23 and 44-45) and the C-terminal helix (residues 60-68). The key interactions involve basic residues Arg22 and Lys23 of CCL17 and a cluster of acidic residues in HCDR2 including Asp52, Asp55 and Asp57. In addition to these electrostatic interactions, van-der-Waals contacts in the center of the epitope occur between Trp33 and Trp105 of VH and Arg22 of CCL17. Given the number of contacts, the key residue of the epitope is Arg22, which stacks against Trp33 of VH and makes numerous contacts to HCDR3. The paratope and the epitope residues are shown in FIG. 7.

The paratope (antibody residues involved in binding CCL17) includes 18 residues that belong to 5 out of 6 CDRs (all except LCDR2).

The C17B236 epitope is on the opposite side of the CCL17 monomer from its dimerization surface. C17B236 thus does not block dimerization of CCL17. The neutralization effect of C17B236 results from the competition with CCR4 for the overlapping epitopes.

Sequence Listing:

| SEQ ID NO | Type | Species | Description | Sequence |
|---|---|---|---|---|
| 1 | PRT | Homo sapiens | CCL17 | argtnvgreccleyfkgai plrklktwyqtsedcsrda ivfvtvqgraicsdpnnkr vknavkylqslers |

-continued

| SEQ ID NO | Type | Species | Description | Sequence |
|---|---|---|---|---|
| 2 | PRT | Cyno | CCL17 | margtnvgrecclkyfkga iplrklktwyqtsedcsrd aivfvtvqnkaicsdpndk kvkkalkylqslers |
| 3 | PRT | cyno | CCL22 | gpyganmedsvccrdyvry rmplrvvkhfywtsdscpr pgvvlltsrdkeicadpry pwvkmilnklsq |
| 4 | PRT | Artificial sequence | HCDR1 fo C17F24 | SYWIG |
| 5 | PRT | Artificial sequence | HCDR2 of C17F24 | IIDPSDSDTRYSPSFQG |
| 6 | PRT | Artificial sequence | HCDR3 of C17F24 | VGPADVWDSFDY |
| 7 | PRT | Artificial sequence | LCDR1 of C17F24 (parent) | KSSQSVLYSSNNKNYLA |
| 8 | PRT | Artificial sequence | LCDR1 of C17B234 | KSSQSVLLSFDNINKLA |
| 9 | PRT | Artificial sequence | LCDR1 fo C17B235 | KSSQSVLYSFYNFNALA |
| 10 | PRT | Artificial sequence | LCDR1 of C17B236 | KSSQSVLLSPWNSNQLA |
| 11 | PRT | Artificial sequence | LCDR1 of C17B237 | KSSQSVLTSYNNSNYLA |
| 12 | PRT | Artificial sequence | LCDR1 of C17B238 | KSSQSVLISAFNQNPLA |
| 13 | PRT | Artificial sequence | LCDR1 of C17B239 | KSSQSVLSSFTNTNTLA |
| 14 | PRT | Artificial sequence | LCDR1 of C17B240 | KSSQSVLYSHVNYNALA |
| 15 | PRT | Artificial sequence | LCDR1 of C17B241 | KSSQSVLNSFTNNNALA |
| 16 | PRT | Artificial sequence | LCDR1 of C17B242 | KSSQSVLFSHDNLNTLA |
| 17 | PRT | Artificial sequence | LCDR1 of C17B243 | KSSQSVLNSFDNKNDLA |
| 18 | PRT | Artificial sequence | LCDR1 of C17B244 | KSSQSVLSSITNVNDLA |
| 19 | PRT | Artificial sequence | LCDR2 fo C17F24 (parent) | WASTRES |

-continued

| SEQ ID NO | Type | Species | Description | Sequence |
|---|---|---|---|---|
| 20 | PRT | Artificial sequence | LCDR2 of C17B234 | NASTRES |
| 21 | PRT | Artificial sequence | LCDR2 fo C17B235 | HASTRES |
| 22 | PRT | Artificial sequence | LCDR2 of C17B236 | GASTRES |
| 23 | PRT | Artificial sequence | LCDR2 fo C17B237 | LASTRES |
| 24 | PRT | Artificial sequence | LCDR2 of C17B238 | DASTRES |
| 25 | PRT | Artificial sequence | LCDR2 of C17B241 | EASTRES |
| 26 | PRT | Artificial sequence | LCDR2 of C17B244 | TASTRES |
| 27 | PRT | Artificial sequence | LCDR3 of C17F24 (parent) | QQYYSTPLT |
| 28 | PRT | Artificial sequence | LCDR3 of C17B234 | QQFYSVPST |
| 29 | PRT | Artificial sequence | LCDR3 of C17B235 | QQFYATPFT |
| 30 | PRT | Artificial sequence | LCDR3 of C17B236 | QQYYLIPST |
| 31 | PRT | Artificial sequence | LCDR3 of C17B237 | QQYLSPPST |
| 32 | PRT | Artificial sequence | LCDR3 of C17B238 | QQYQFIPFT |
| 33 | PRT | Artificial sequence | LCDR3 of C17B239 | QQYLIYPST |
| 34 | PRT | Artificial sequence | LCDR3 fo C17B240 | QQYYTLPAT |
| 35 | PRT | Artificial sequence | LCDR3 of C17B241 | QQTNSIPLT |
| 36 | PRT | Artificial sequence | LCDR3 of C17B242 | QQYYAVPQT |
| 37 | PRT | Artificial sequence | LCDR3 of C17B243 | QQHWQTPLT |

-continued

Sequence Listing:

| SEQ ID NO | Type | Species | Description | Sequence |
|---|---|---|---|---|
| 38 | PRT | Artificial sequence | LCDR3 of C17B244 | QQYYHDPFT |
| 39 | PRT | | LCDR2 of C17B257 | AASTRES |
| 40 | PRT | | LCDR2 of C17B262 | SASTRES |
| 41 | PRT | | LCDR2 fo C17B264 | IASTRES |
| 42 | PRT | | HCDR3 of C17B293 | VGPADVWDAFDY |
| 43 | PRT | | HCDR3 of C17B294 | VGPADVWDTFDY |
| 44 | PRT | | HCDR3 of C17B295 | VGPADVWESFDY |
| 45 | PRT | Homo sapiens | VH of C17F24, C17B234, C17B235, C17B236, C17B237, C17B238, C17B239, C17B240, C17B241, C17B242, C17B243, C17B244, C17B257, C17B258, C17B260, C17B262, C17B266, C17B264 | EVQLVQSGAEVKKPGESLK ISCKGSGYSFTSYWIGWVR QMPGKGLEWMGIIDPSDSD TRYSPSFQGQVTISADKSI STAYLQWSSLKASDTAMYY CARVGPADVWDSFDYWGQG TLVTVSS |
| 46 | PRT | HOMO sapiens | VH of C17M293 | EVQLVQSGAEVKKPGESLKISC KGSGYSFTSYWIGWVRQMPG KGLEWMGIIDPSDSDTRYSPSF QGQVTISADKSISTAYLQWSSL KASDTAMYYCARVGPADVW DAFDYWGQGTLVTVSS |
| 47 | PRT | Homo sapiens | VH of C17B294 | EVQLVQSGAEVKKPGESLKISC KGSGYSFTSYWIGWVRQMPG KGLEWMGIIDPSDSDTRYSPSF QGQVTISADKSISTAYLQWSSL KASDTAMYYCARVGPADVW DTFDYWGQGTLVTVSS |
| 48 | PRT | Homo sapiens | VH of C17B295 | EVQLVQSGAEVKKPGESLKISC KGSGYSFTSYWIGWVRQMPG KGLEWMGIIDPSDSDTRYSPSF QGQVTISADKSISTAYLQWSSL KASDTAMYYCARVGPADVWE SFDYWGQGTLVTVSS |
| 49 | PRT | Homo sapiens | VL of C17F24 (parent) | DIVMTQSPDSLAVSLGERATINC KSSQSVLYSSNNKNYLAWYQQKP GQPPKLLIYWASTRESGVPDRFS GSGSGIDFILTISSLQAEDVAVY YCQQYYSTPLTFGQGTKVEIK |

|SEQ ID NO|Type|Species|Description|Sequence|
|---|---|---|---|---|
|50|PRT|Homo sapiens|VL of C17B234|DIVMTQSPDSLAVSLGERATIN CKSSQSVLLSFDNINKLAWYQ QKPGQPPKLLIYNASTRESGVP DRFSGSGSGTDFTLTISSLQAE DVAVYYCQQFYSVPSTFGQGT KVEIK|
|51|PRT|Homo sapiens|VL of C17B235|DIVMTQSPDSLAVSLGERATIN CKSSQSVLYSFYNFNALAWYQ QKPGQPPKLLIYHASTRESGVP DRFSGSGSGTDFTLTISSLQAE DVAVYYCQQFYATPFTFGQGT KVEIK|
|52|PRT|Homo sapiens|VL of C17B236|DIVMTQSPDSLAVSLGERATIN CKSSQSVLLSPWNSNQLAWY QQKPGQPPKLLIYGASTRESGV PDRFSGSGSGTDFTLTISSLQAE DVAVYYCQQYYLIPSTFGQGTK VEIK|
|53|PRT|Homo sapiens|VL of C17B237|DIVMTQSPDSLAVSLGERATIN CKSSQSVLTSYNNSNYLAWYQ QKPGQPPKLLIYLASTRESGVP DRFSGSGSGTDFTLTISSLQAE DVAVYYCQQYLSPPSTFGQGT KVEIK|
|54|PRT|Homo sapiens|VL of C17B238|DIVMTQSPDSLAVSLGERATIN CKSSQSVLISAFNQNPLAWYQ QKPGQPPKLLIYDASTRESGVP DRFSGSGSGTDFTLTISSLQAE DVAVYYCQQYQFIPFTFGQGT KVEIK|
|55|PRT|Homo sapiens|VL of C17B239|DIVMTQSPDSLAVSLGERATIN CKSSQSVLSSFTNTNTLAWYQ QKPGQPPKLLIYHASTRESGVP DRFSGSGSGTDFTLTISSLQAE DVAVYYCQQYLIYPSTFGQGTK VEIK|
|56|PRT|Homo sapiens|VL of C17B240|DIVMTQSPDSLAVSLGERATIN CKSSQSVLYSHVNYNALAWYQ QKPGQPPKLLIYNASTRESGVP DRFSGSGSGTDFTLTISSLQAE DVAVYYCQQYYTLPATFGQGT KVEIK|
|57|PRT|Homo sapiens|VL of C17B241|DIVMTQSPDSLAVSLGERATIN CKSSQSVLNSFTNNNALAWY QQKPGQPPKLLIYEASTRESGV PDRFSGSGSGTDFTLTISSLQAE DVAVYYCQQTNSIPLTFGQGT KVEIK|
|58|PRT|Homo sapiens|VL of C17B242|DIVMTQSPDSLAVSLGERATIN CKSSQSVLFSHDNLNTLAWYQ QKPGQPPKLLIYHASTRESGVP DRFSGSGSGTDFTLTISSLQAE DVAVYYCQQYYAVPQTFGQG TKVEIK|
|59|PRT|Homo sapiens|VL of C17B243|DIVMTQSPDSLAVSLGERATIN CKSSQSVLNSFDNKNDLAWY QQKPGQPPKLLIYEASTRESGV PDRFSGSGSGTDFTLTISSLQAE DVAVYYCQQHWQTPLTFGQG TKVEIK|
|60|PRT|Homo sapiens|VL of C17B244|DIVMTQSPDSLAVSLGERATINC KSSQSVLSSITNVNDLAWYQQKP GQPPKLLIYTASTRESGVPDRFS|

-continued

Sequence Listing:

| SEQ ID NO | Type | Species | Description | Sequence |
|---|---|---|---|---|
| | | | | GSGSGTDFTLTISSLQAEDVAVY YCQQYYHDPFTFGQGTKVEIK |
| 61 | PRT | Homo sapiens | VL of C17B257 | DIVMTQSPDSLAVSLGERATIN CKSSQSVLLSFDNINKLAWYQ QKPGQPPKLLIYAASTRESGVP DRFSGSGSGTDFTLTISSLQAE DVAVYYCQQFYSVPSTFGQGT KVEIK |
| 62 | PRT | Homo sapiens | VL of C17B258 | DIVMTQSPDSLAVSLGERATIN CKSSQSVLLSFDNINKLAWYQ QKPGQPPKLLIYDASTRESGVP DRFSGSGSGTDFTLTISSLQAE DVAVYYCQQFYSVPSTFGQGT KVEIK |
| 63 | PRT | Homo sapiens | VL of C17B260 | DIVMTQSPDSLAVSLGERATIN CKSSQSVLLSFDNINKLAWYQ QKPGQPPKLLIYGASTRESGVP DRFSGSGSGTDFTLTISSLQAE DVAVYYCQQFYSVPSTFGQGT KVEIK |
| 64 | PRT | Homo sapiens | VL of C17B262 | DIVMTQSPDSLAVSLGERATIN CKSSQSVLLSFDNINKLAWYQ QKPGQPPKLLIYSASTRESGVP DRFSGSGSGTDFTLTISSLQAE DVAVYYCQQFYSVPSTFGQGT KVEIK |
| 65 | PRT | Homo sapiens | VL of C17B263 | DIVMTQSPDSLAVSLGERATIN CKSSQSVLLSFDNINKLAWYQ QKPGQPPKLLIYTASTRESGVP DRFSGSGSGTDFTLTISSLQAE DVAVYYCQQFYSVPSTFGQGT KVEIK |
| 66 | PRT | Homo sapiens | VL of C17B264 | DIVMTQSPDSLAVSLGERATIN CKSSQSVLLSFDNINKLAWYQ QKPGQPPKLUYIASTRESGVP DRFSGSGSGTDFTLTISSLQAE DVAVYYCQQFYSVPSTFGQGT KVEIK |
| 67 | PRT | Homo sapiens | CB302 HC | EVQLVQSGAEVKKPGESLK ISCKGSGYSFTSYWIGWVR QMPGKGLEWMGIIDPSDSD TRYSPSFQGQVTISADKSI STAYLQWSSLKASDTAMYY CARVGPADVWDAFDYWGQG TLVTVSSASTKGPSVFPLA PCSRSTSESTAALGCLVKD YFPEPVTVSWNSGALTSGV HTFPAVLQSSGLYSLSSVV TVTSSNFGTQTYTCNVDHK PSNTKVDKTVERKCCVECP PCPAPPAAASSVFLFPPKP KDTLMISRTPEVTCVVVDV SAEDPEVQFNWYVDGVEVH NAKTKPREEQFNSTFRVVS VLTVLHQDWLNGKEYKCKV SNKGLPSSIEKTISKTKGQ PREPQVYTLPPSREEMTKN QVSLTCLVKGFYPSDIAVE WESNGQPENNYKTTPPMLD SDGSFFLYSKLTVDKSRWQ QGNVFSCSVMHEALHNHYT QKSLSLSPGK |
| 68 | PRT | Homo sapiens | CB302 LC | DIVMTQSPDSLAVSLGERA TINCKSSQSVLLSFDNINK LAWYQQKPGQPPKLLIYDA STRESGVPDRFSGSGSGTD |

Sequence Listing:

| SEQ ID NO | Type | Species | Description | Sequence |
|---|---|---|---|---|
| | | | | FTLTISSLQAEDVAVYYCQ QFYSVPSTFGQGTKVEIKR TVAAPSVFIFPPSDEQLKS GTASVVCLLNNFYPREAKV QWKVDNALQSGNSQESVTE QDSKDSTYSLSSTLTLSKA DYEKHKVYACEVTHQGLSS PVTKSFNRGEC |
| 69 | PRT | Homo sapiens | CB301 HC | EVQLVQSGAEVKKPGESLK ISCKGSGYSFTSYWIGWVR QMPGKGLEWMGIIDPSDSD TRYSPSFQGQVTISADKSI STAYLQWSSLKASDTAMYY CARVGPADVWDTFDYWGQG TLVTVSSASTKGPSVFPLA PCSRSTSESTAALGCLVKD YFPEPVTVSWNSGALTSGV HTFPAVLQSSGLYSLSSVV TVTSSNFGTQTYTCNVDHK PSNTKVDKTVERKCCVECP PCPAPPAAASSVFLFPPKP KDTLMISRTPEVTCVVVDV SAEDPEVQFNWYVDGVEVH NAKTKPREEQFNSTFRVVS VLTVLHQDWLNGKEYKCKV SNKGLPSSIEKTISKTKGQ PREPQVYTLPPSREEMTKN QVSLTCLVKGFYPSDIAVE WESNGQPENNYKTTPPMLD SDGSFFLYSKLTVDKSRWQ QGNVFSCSVMHEALHNHYT QKSLSLSPGK |
| 70 | PRT | Homo sapiens | CB301 LC | DIVMTQSPDSLAVSLGERA TINCKSSQSVLLSFDNINK LAWYQQKPGQPPKLLIYDA STRESGVPDRFSGSGSGTD FTLTISSLQAEDVAVYYCQ QFYSVPSTFGQGTKVEIKR TVAAPSVFIFPPSDEQLKS GTASVVCLLNNFYPREAKV QWKVDNALQSGNSQESVTE QDSKDSTYSLSSTLTLSKA DYEKHKVYACEVTHQGLSS PVTKSFNRGEC |

We claim:

1. A method of treating asthma or a respiratory allergic disease in a subject in need thereof, comprising administering to the subject, for a time sufficient to treat the asthma or respiratory allergic disease, an effective amount of an isolated antibody that specifically binds human CCL17, wherein the antibody comprises a heavy chain complementarity determining region (HCDR) 1, a HCDR2, and a HCDR3, and a light chain complementarity determining region (LCDR) 1, a LCDR2, and a LCDR3 of SEQ ID NOs: 4, 5, 42, 8, 24, and 28, respectively.

2. The method of claim 1, wherein the antibody comprises the heavy chain variable region (VH) of SEQ ID NO: 46 and the light chain variable region (VL) of SEQ ID NO: 62.

3. The method of claim 1, wherein the antibody is human or humanized.

4. The method of claim 1, wherein the antibody is of IgG1, IgG2, IgG3, or IgG4 isotype.

5. The method of claim 1, wherein the antibody comprises a substitution in an Fc region.

6. The method of claim 5, wherein the substitution comprises V234A, G237A, P238S, H268A, V309L, A330S or P331S substitution on IgG2, or S228P, L234A or L235A substitution on IgG4, wherein residue numbering is according to the EU Index.

7. The method of claim 6, wherein the substitution comprises V234A/G237A/P238S/H268A/V309L/A330S/P331S substitution on IgG2 or S228P/L234A/L235A substitution on IgG4, wherein residue numbering is according to the EU Index.

* * * * *

UNITED STATES PATENT AND TRADEMARK OFFICE
CERTIFICATE OF CORRECTION

PATENT NO. : 10,829,549 B2  Page 1 of 1
APPLICATION NO. : 15/835529
DATED : November 10, 2020
INVENTOR(S) : Ken Boakye et al.

It is certified that error appears in the above-identified patent and that said Letters Patent is hereby corrected as shown below:

On the Title Page

Item (73) Assignee: "Jannsen Biotech, Inc." should read --Janssen Biotech, Inc.--

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*